(12) United States Patent
Kwong et al.

(10) Patent No.: US 9,911,930 B2
(45) Date of Patent: *Mar. 6, 2018

(54) ORGANIC ELECTROLUMINESCENT MATERIALS AND DEVICES

(71) Applicant: Universal Display Corporation, Ewing, NJ (US)

(72) Inventors: Raymond Kwong, Plainsboro, NJ (US); Bin Ma, Plainsboro, NJ (US); Chuanjun Xia, Lawrenceville, NJ (US); Bert Alleyne, Ewing, FL (US); Jason Brooks, Philadelphia, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,538

(22) Filed: Jan. 6, 2017

(65) Prior Publication Data

US 2017/0117492 A1    Apr. 27, 2017

Related U.S. Application Data

(63) Continuation of application No. 14/826,762, filed on Aug. 14, 2015, now Pat. No. 9,577,201, which is a continuation of application No. 13/849,028, filed on Mar. 22, 2013, now Pat. No. 9,142,786, which is a (Continued)

(51) Int. Cl.
*H01L 51/54* (2006.01)
*C09K 11/06* (2006.01)
*H01L 51/00* (2006.01)
*C07F 15/00* (2006.01)

(Continued)

(52) U.S. Cl.
CPC ...... *H01L 51/0085* (2013.01); *C07F 15/0033* (2013.01); *C09K 11/06* (2013.01); *H01L 51/0081* (2013.01); *H01L 51/0092* (2013.01); *H05B 33/14* (2013.01); *C09K 2211/1007* (2013.01); *C09K 2211/1029* (2013.01); *C09K 2211/1037* (2013.01); *C09K 2211/185* (2013.01); *C09K 2211/188* (2013.01); *H01L 51/5016* (2013.01); *H01L 51/5056* (2013.01);

(Continued)

(58) Field of Classification Search
CPC .. C07F 15/00; C07F 15/0006; C07F 15/0013; C07F 15/002; C07F 15/0026; C07F 15/0033; C07F 15/0046; C07F 15/006; C07F 15/0073; C07F 15/0086; C09K 11/06; C09K 2211/00; C09K 2211/10; C09K 2211/1018; C09K 2211/1025; C09K 2211/1029; C09K 2211/18; C09K 2211/185; C09K 2211/1007; C09K 2211/1037; C09K 2211/188; H05B 33/14; H01L 51/0032; H01L 51/005; H01L 51/0084; H01L 51/0085; H01L 51/0092; H01L 51/50; H01L 51/5012; H01L 51/5016

USPC ...... 428/690, 917, 336, 411.4; 313/502–509; 257/40, 88–104, E51.001–E51.052; 252/301.16–301.35; 546/4

See application file for complete search history.

(56) References Cited

U.S. PATENT DOCUMENTS

| 4,769,292 | A | 9/1988 | Tang et al. |
| 5,061,569 | A | 10/1991 | VanSlyke et al. |
| 5,247,190 | A | 9/1993 | Friend et al. |

(Continued)

FOREIGN PATENT DOCUMENTS

| CN | 1589307 | 3/2005 |
| EP | 0650955 | 5/1995 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Andrew K Bohaty
(74) *Attorney, Agent, or Firm* — Duane Morris LLP

(57) ABSTRACT

A compound including a ligand having the formula:

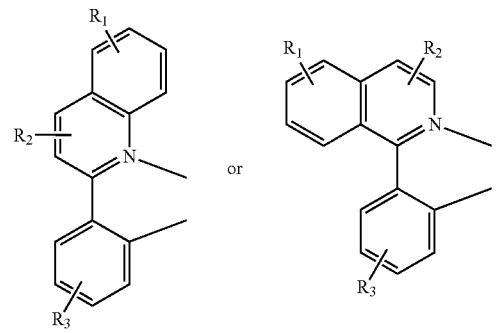

is disclosed. In these formulas, each $R_1$, $R_2$, and $R_3$ is independently selected from hydrogen, alkyl, and aryl; at least one of $R_1$ and $R_2$ is a branched alkyl containing at least 4 carbon atoms, where the branching occurs at a position further than the benzylic position; where $R_1$ and $R_3$ are mono-, di-, tri-, tetra-, or no substitutions; and $R_2$ is mono-, di-, or no substitutions. Heteroleptic iridium complexes including such compounds, and devices including such compounds are also disclosed.

12 Claims, 3 Drawing Sheets

Related U.S. Application Data continuation of application No. 12/044,234, filed on Mar. 7, 2008, now Pat. No. 8,431,243.

(60) Provisional application No. 60/905,758, filed on Mar. 8, 2007.

(51) Int. Cl.
*H05B 33/14* (2006.01)
*H01L 51/50* (2006.01)

(52) U.S. Cl.
CPC ...... *H01L 51/5072* (2013.01); *H01L 51/5092* (2013.01)

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 9,034,483 B2 * | 5/2015 | Alleyne ............. H01L 51/0085 428/690 |
| 9,142,786 B2 * | 9/2015 | Kwong ............... C07F 15/0033 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0068526 A1 | 4/2003 | Kamatani et al. |
| 2003/0072964 A1 | 4/2003 | Kwong et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0100189 A1 | 5/2004 | Adachi et al. |
| 2004/0127710 A1 | 7/2004 | Park et al. |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0204785 A1 | 9/2006 | Kim et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0004918 A1 | 1/2007 | Jeong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 1348711 | 10/2003 |
| EP | 1725079 | 11/2006 |
| EP | 2034538 | 3/2009 |
| JP | H09-279136 | 10/1997 |
| JP | 2003073387 | 3/2003 |
| JP | 2005011610 | 1/2005 |
| JP | 2007123392 | 5/2007 |
| JP | 2007254297 | 10/2007 |
| JP | 2008074939 | 4/2008 |
| KR | 100662379 | 1/2007 |
| WO | 01/39234 | 5/2001 |
| WO | 02/02714 | 1/2002 |
| WO | 0215654 | 2/2002 |
| WO | 03033617 | 4/2003 |
| WO | 03040256 | 5/2003 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2005124889 | 12/2005 |
| WO | 2006009024 | 1/2006 |
| WO | 2006014599 | 2/2006 |
| WO | 2006005997 | 4/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |

(56) References Cited

FOREIGN PATENT DOCUMENTS

| WO | 2009066779 | 5/2009 |
|---|---|---|
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6,(1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based On Silole Derivatives And Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N N^C^N-C N^C^N- N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes Of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

(56) References Cited

OTHER PUBLICATIONS

Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Notice of Reasons for Rejection issued Aug. 28, 2017 for corresponding Japanese Patent Application No. 2016-216333.

\* cited by examiner

ORGANIC ELECTROLUMINESCENT MATERIALS AND DEVICES

CROSS-REFERENCES TO RELATED APPLICATIONS

This application is a continuation U.S. patent application Ser. No. 14/826,762, filed Aug. 14, 2015, which is a continuation application of U.S. patent application Ser. No. 13/849,028, filed Mar. 22, 2013, now U.S. Pat. No. 9,142,786, which is a continuation of U.S. patent application Ser. No. 12/044,234, filed Mar. 7, 2008, now U.S. Pat. No. 8,431,243, which claims priority to U.S. Provisional Application 60/905,758, filed Mar. 8, 2007, the entireties of which are incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

BACKGROUND OF THE INVENTION

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

Electronic display currently is a primary means for rapid delivery of information. Television sets, computer monitors, instrument display panels, calculators, printers, wireless phones, handheld computers, etc. aptly illustrate the speed, versatility, and interactivity that is characteristic of this medium. Of the known electronic display technologies, organic light emitting devices (OLEDs) are of considerable interest for their potential role in the development of full color, flat-panel display systems that may render obsolete the bulky cathode ray tubes still currently used in many television sets and computer monitors.

Generally, OLEDs are comprised of several organic layers in which at least one of the layers can be made to electroluminesce by applying a voltage across the device (see, e.g., Tang, et al., Appl. Phys. Lett. 1987, 51, 913 and Burroughes, et al., Nature, 1990, 347, 359). When a voltage is applied across a device, the cathode effectively reduces the adjacent organic layers (i.e., injects electrons), and the anode effectively oxidizes the adjacent organic layers (i.e., injects holes). Holes and electrons migrate across the device toward their respective oppositely charged electrodes. When a hole and electron meet on the same molecule, recombination is said to occur, and an exciton is formed. Recombination of the hole and electron in luminescent compounds is accompanied by radiative emission, thereby producing electroluminescence.

Depending on the spin states of the hole and electron, the exciton resulting from hole and electron recombination can have either a triplet or singlet spin state. Luminescence from a singlet exciton results in fluorescence, whereas luminescence from a triplet exciton results in phosphorescence. Statistically, for organic materials typically used in OLEDs, one quarter of the excitons are singlets, and the remaining three-quarters are triplets (see, e.g., Baldo, et al., Phys. Rev. B, 1999, 60, 14422). Until the discovery that there were certain phosphorescent materials that could be used to fabricate practical electro-phosphorescent OLEDs (U.S. Pat. No. 6,303,238) and, subsequently, demonstration that such electro-phosphorescent OLEDs could have a theoretical quantum efficiency of up to 100% (i.e., harvesting all of both triplets and singlets), the most efficient OLEDs were typically based on materials that fluoresced. Fluorescent materials luminesce with a maximum theoretical quantum efficiency of only 25% (where quantum efficiency of an OLED refers to the efficiency with which holes and electrons recombine to produce luminescence), since the triplet to ground state transition of phosphorescent emission is formally a spin forbidden process. Electro-phosphorescent OLEDs have now been shown to have superior overall device efficiencies as compared with electro-fluorescent OLEDs (see, e.g., Baldo, et al., Nature, 1998, 395, 151 and Baldo, et al., Appl. Phys. Lett. 1999, 75(3), 4).

Due to strong spin-orbit coupling that leads to singlet-triplet state mixing, heavy metal complexes often display efficient phosphorescent emission from such triplets at room temperature. Accordingly, OLEDs comprising such complexes have been shown to have internal quantum efficiencies of more than 75% (Adachi, et al., Appl. Phys. Lett., 2000, 77, 904). Certain organometallic iridium complexes have been reported as having intense phosphorescence (Lamansky, et al., Inorganic Chemistry, 2001, 40, 1704), and efficient OLEDs emitting in the green to red spectrum have been prepared with these complexes (Lamansky, et al., J. Am. Chem. Soc., 2001, 123, 4304). Red-emitting devices containing iridium complexes have been prepared according to U.S. Pat. No. 6,821,645. Phosphorescent heavy metal organometallic complexes and their respective devices have also been the subject of International Patent Application Publications WO 00/57676, WO 00/70655, and WO 01/41512; U.S. Publications 2006/0202194 and 2006/0204785; and U.S. Pat. Nos. 7,001,536; 6,911,271; 6,939,624; and 6,835,469.

Despite the recent discoveries of efficient heavy metal phosphors and the resulting advancements in OLED technology, there remains a need for even greater efficiency in devices. Fabrication of brighter devices that use less power and have longer lifetimes will contribute to the development of new display technologies and help realize the current goals toward full color electronic display on flat surfaces. The phosphorescent organometallic compounds, and the devices comprising them, described herein, help fulfill these and other needs.

SUMMARY OF THE INVENTION

In one embodiment, an iridium compound has a formula:

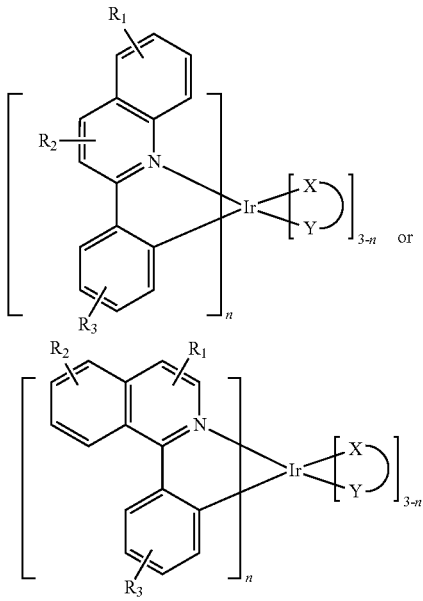

wherein n is 1, 2 or 3; each of $R_1$, $R_2$, and $R_3$ is independently a hydrogen, or a mono-, di-, tri-, tetra-, or penta-substitution of alkyl or aryl; at least one of $R_1$, $R_2$, and $R_3$ is a branched alkyl containing at least 4 carbon atoms, and wherein the branching occurs at a position further than the benzylic position; and X—Y is an ancillary ligand. The branched alkyl can be an isobutyl group. The X—Y ligand can be acac. Specific exemplary compounds are also provided.

In another embodiment, a compound includes a ligand having the formula:

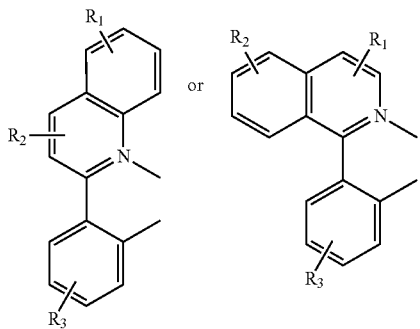

each of $R_1$, $R_2$, and $R_3$ is independently a hydrogen, or a mono-, di-, tri-, tetra-, or penta-substitution of alkyl or aryl; at least one of $R_1$, $R_2$, and $R_3$ is a branched alkyl containing at least 4 carbon atoms, and wherein the branching occurs at a position further than the benzylic position. The ligand can be coordinated to a metal having an atomic number greater than 40, e.g., Ir.

In yet another embodiment, specific compounds are provided, e.g., Compounds 1-24.

In yet another embodiment, an organic light emitting device comprises an anode, a cathode, and an emissive organic layer disposed between the anode and the cathode. The organic emissive layer comprises one or more of the compounds provided. The organic emissive layer can further comprise, e.g., Compound C or BAlq.

DETAILED DESCRIPTION OF THE INVENTION

Figure 1:
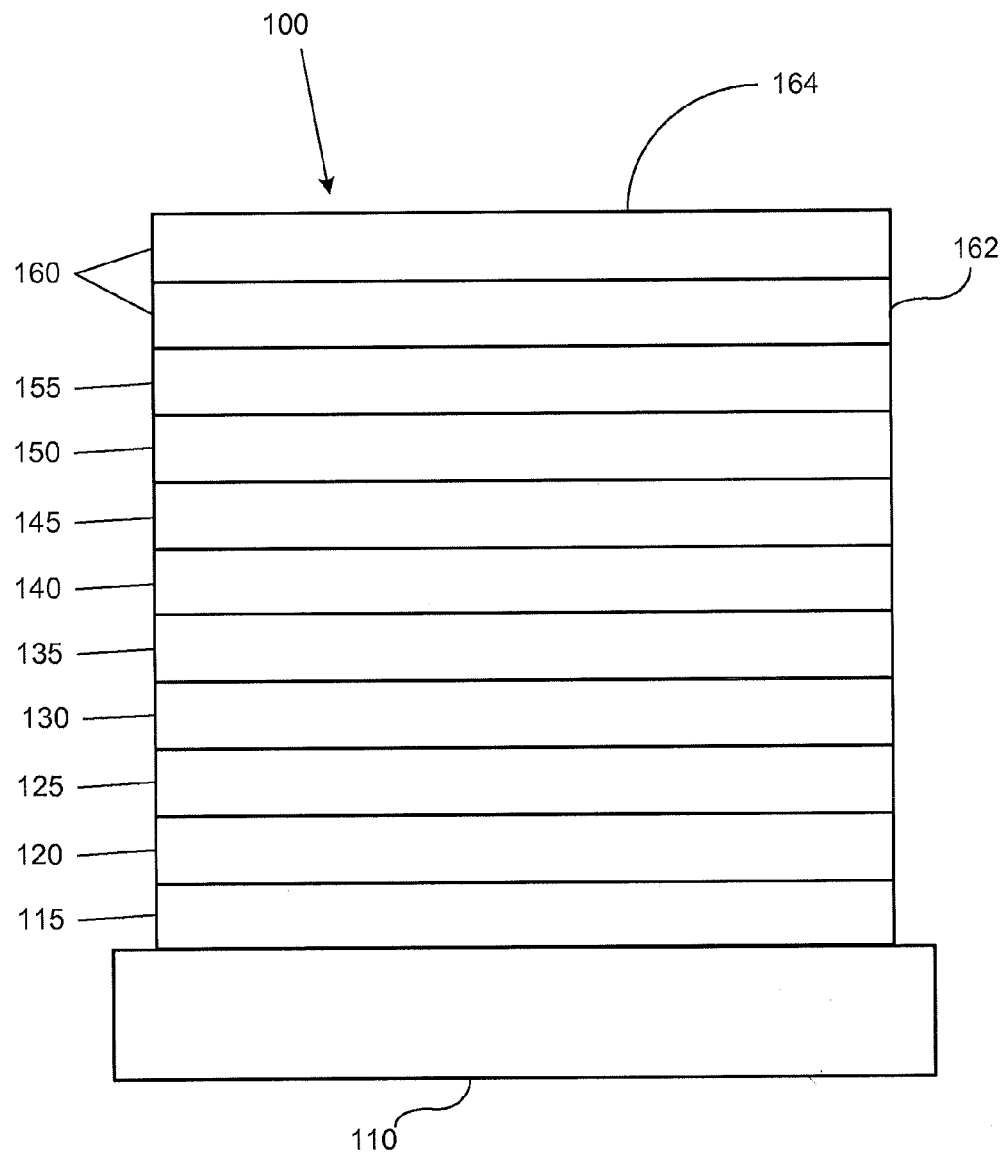
FIG. 1 shows an organic light emitting device having separate electron transport, hole transport, and emissive layers, as well as other layers.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

Figure 2:
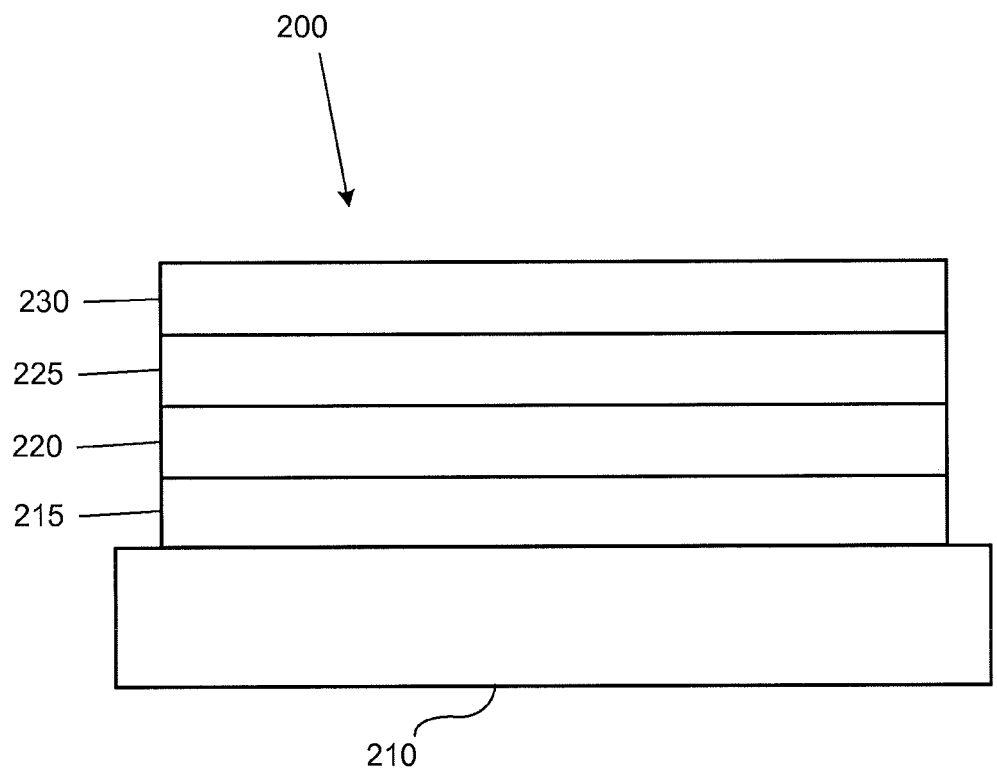
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Numerous Ir(2-phenylquinoline) and Ir(1-phenylisoquinoline) type phosphorescent materials have been synthesized, and OLEDs incorporating them as the dopant emitters have been fabricated. The devices may advantageously exhibit high current efficiency, high stability, narrow emission, high processability (such as high solubility and low evaporation temperature), high luminous efficiency, and/or high luminous efficiency: quantum efficiency ratio (LE: EQE).

Using the base structure of Ir(3-Meppy)$_3$, different alkyl and fluoro substitution patters were studied to establish a structure-property relationship with respect to material processability (evaporation temperature, evaporation stability, solubility, etc.) and device characteristics of Ir(2-phenylquinoline) and Ir(1-phenylisoquinoline) type phosphorescent materials and their PHOLEDs. Alkyl and fluoro substitutions are particular important because they offer a wide range of tenability in terms of evaporation temperature, solubility, energy levels, device efficiency, etc. Moreover, they are stable as functional groups chemically and in device operation when applied appropriately.

Figure 3:
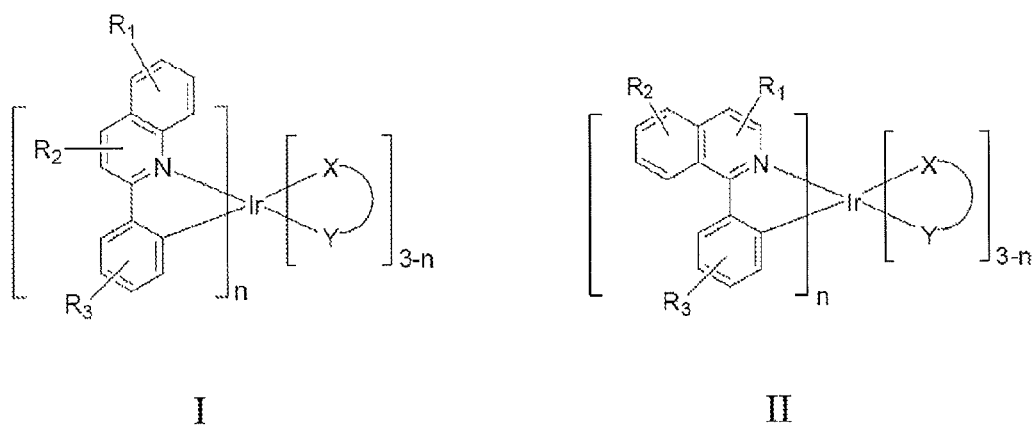
FIG. 3 shows examples of iridium compounds.

In one embodiment, an iridium compound has the formula (also illustrated in FIG. 3):

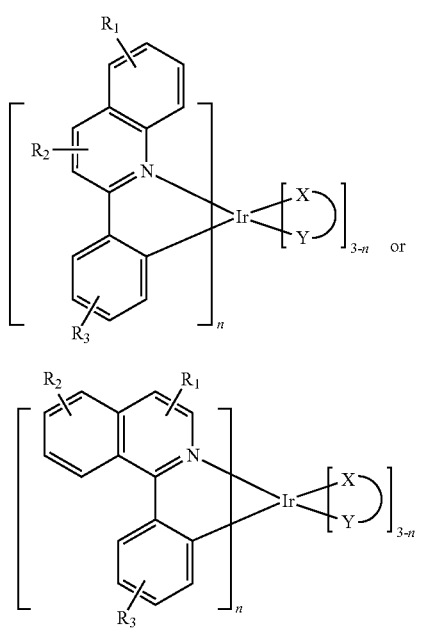

wherein n is 1, 2 or 3;
each of $R_1$, $R_2$, and $R_3$ is independently a hydrogen, or a mono-, di-, tri-, tetra-, or penta-substitution of alkyl or aryl;
at least one of $R_1$, $R_2$, and $R_3$ is a branched alkyl containing at least 4 carbon atoms, and wherein the branching occurs at a position further than the benzylic position; and
X—Y is an ancillary ligand.

Together, X and Y represent a bidentate ligand. Numerous bidentate ligands are known to those skilled in the art and many suitable examples are provided in Cotton and Wilkinson, Advanced Inorganic Chemistry, Fourth Ed., John Wiley & Sons, New York, 1980. In some embodiments, bidentate ligands are monoanionic. Suitable bidentate ligands include, but are not limited to, acetylacetonate (acac), picolinate (pic), hexafluoroacetylacetonate, salicylidene, 8-hydroxyquinolinate; amino acids, salicylaldehydes, and iminoacetonates. In one embodiment, X—Y is acac. Bidentate ligands also include biaryl compounds. In some embodiments, the biaryl compounds coordinate to the metal atom through a carbon atom and a nitrogen atom. As used herein, the term "biaryl" refers to compounds comprising two aryl groups covalently joined by a single bond. The aryl groups of a biaryl compound can be aryl or heteroaryl, including both monocyclic or poly-cyclic aryl and heteroaryl groups. Exemplary biaryl groups include, but are not limited to, biphenyl, bipyridyl, phenylpyridyl, and derivatives thereof. Biaryl compounds can serve as bidentate ligands in metal coordination complexes, for instance, by coordinating though one atom in each of the two aryl groups. The coordinating atoms can be carbon or a heteroatom. Further suitable bidentate ligands include, but are not limited to, 2-(1-naphthyl)benzoxazole, 2-phenylbenzoxazole, 2-phenylbenzothiazole, coumarin, thienylpyridine, phenylpyridine, benzothienylpyridine, 3-methoxy-2-phenylpyridine, thienylpyridine, tolylpyridine, phenylimines, vinylpyridines, arylquinolines, pyridylnaphthalenes, pyridylpyrroles, pyridylimidazoles, phenylindoles, and derivatives thereof. Suitable bidentate ligands also include those provided by U.S. Pat. Nos. 7,001,536; 6,911,271; 6,939,624; and 6,835,469.

In another embodiment, X and Y can each be a monodentate ligand, that is, any ligand capable of coordinating to a metal atom through one atom. Numerous monodentate ligands are well known in the art, and many suitable examples are provided in Cotton and Wilkinson, supra. In some embodiments, monodentate ligands can include F, Cl, Br, I, CO, CN, CN($R^4$), $SR^4$, SCN, OCN, $P(R^4)_3$, $P(OR^4)_3$, $N(R^4)_3$, NO, $N_3$, or a nitrogen-containing heterocycle optionally substituted by one or more substituents X. Each $R^4$ is independently H, $C_1$-$C_{20}$ alkyl, $C_2$-$C_{20}$ alkenyl, $C_2$-$C_{20}$ alkynyl, $C_1$-$C_{20}$ heteroalkyl, $C_3$-$C_{40}$ aryl, $C_3$-$C_{40}$ heteroaryl. $R^4$ is optionally substituted by one or more substituents X, wherein each X is independently H, F, Cl, Br, I, $R^5$, $OR^5$, $N(R^5)_2$, $P(R^5)_2$, $P(OR^5)_2$, $POR^5$, $PO_2R^5$, $PO_3R^5$, $SR^5$, $Si(R^5)_3$, $B(R^5)_2$, $B(OR^5)_2 C(O)R^5$, $C(O)OR^5$, $C(O)N(R^5)_2$, CN, $NO_2$, $SO_2$, $SOR^5$, $SO_2R^5$, or $SO_3R^5$. Each $R^5$ is independently H, $C_1$-$C_{20}$ alkyl, $C_1$-$C_{20}$ perhaloalkyl, $C_2$-$C_{20}$ alkenyl, $C_2$-$C_{20}$ alkynyl, $C_1$-$C_{20}$ heteroalkyl, $C_3$-$C_{40}$ aryl, or $C_3$-$C_{40}$ heteroaryl. The phrase "nitrogen-containing heterocycle" as used herein refers to any heterocyclic group containing at least one nitrogen atom. Nitrogen-containing heterocycles can be saturated or unsaturated and include, but are not limited to, pyridine, imidazole, pyrrolidine, piperidine, morpholine, pyrimidine, pyrazine, pyridazine, pyrrole, 1,3,4-triazole, tetrazole, oxazole, thiazole, and derivatives thereof. In further embodiments, one of X and Y is a neutral monodentate ligand, and the other of X and Y is monoanionic, i.e., X and Y have a combined charge of (−1). For example, X can be chloro, and Y can be pyridyl.

Some of the compounds provided comprise at least one bidentate phenylquinolinato (pq) ligand. The term phenylquinolinato, or pq, as used herein refers to both substituted and non-substituted ligands, and the number (n) of coordinated pq ligands can be 1, 2, or 3. In some embodiments, compounds comprise m–1 pq ligands (wherein m is the formal charge of the metal) or, in some embodiments, two pq ligands. Phenylquinolinato ligands can be substituted with substituents $R_1$, $R_2$, and $R_3$ as defined above. Any combination of substituents is suitable. Adjacently-positioned substituents can, together, comprise a 4- to 7-member cyclic group that is fused to the ligand. For example, the pairs $R_1$ and $R_2$ or $R_2$ and $R_3$ can comprise a fused cyclic group. The phrase "fused cyclic group" refers to a cyclic group that shares one or more bonds with a further cyclic group. The pq ligands can have any number of fused cyclic group substituents. Any feasible combination of fused cyclic groups and the remaining of $R_1$, $R_2$, and $R_3$ not involved in a fused cyclic group is contemplated.

As used herein, the term "alkyl" includes linear, branched, and cyclic alkyl groups. In some embodiments, alkyl groups are $C_1$-$C_{20}$ alkyl groups. Exemplary alkyl groups include, but are not limited to, methyl, ethyl, n-propyl, isopropyl, n-butyl, isobutyl, cyclohexyl, and norbornyl. In one embodiment, the compound includes a branched aryl, wherein the branching occurs at a position further than the benzylic position. The benzylic position is the carbon attached directly to the aryl ring. Thus, in this embodiment, the alkyl chain projects linearly from the aryl ring for at least two carbons until branching begins. The branched alkyl can be, e.g., an isobutyl group.

As used herein, the term "heteroalkyl" refers to alkyl groups including one or more heteroatoms such as O, S, or N. Heteroalkyl groups can also comprise unsaturations. Exemplary heteroalkyl groups include, but are not limited to, pyrrolidinyl, piperidinyl, and morpholinyl. The term "perhaloalkyl" refers to alkyl groups substituted by halogen. Exemplary perhaloalkyl group include, but are not limited to, trifluoromethyl, trichloromethyl, and pentafluoroethyl. "Alkenyl" groups refer to alkyl groups having one or more double bonds, and "alkynyl" groups refer to alkyl groups having one or more triple bonds. "Aryl" groups can be any mono- or polycyclic aromatic group, and "heteroaryl" refers to an aryl group including one or more heteroatoms such as O, S, or N. Aryl groups can have about 3 to about 40 carbon atoms and include, but are not limited to, phenyl, 4-methylphenyl, naphthyl, anthracenyl, and phenanthryl. Heteroaryl groups include, but are not limited to, pyridyl, indolyl, benzothiophene, and quinolinyl. "Amino" groups as used herein include amino, alkylamino, dialkylamino, arylamino, and diarylamino groups. Exemplary amino groups include, but are not limited to, $NH_2$, methylamino, dimethylamino, phenylamino, and diphenylamino. "Halo" groups are halogens including, e.g., fluoro, chloro, bromo, and iodo.

Specific examples of compounds of formula I or II include:

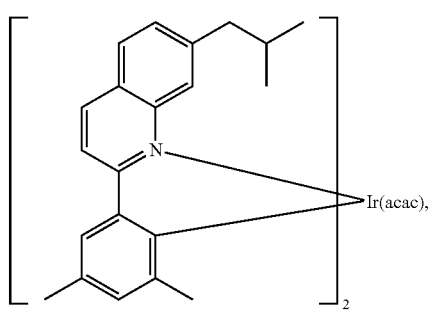

Compound 9

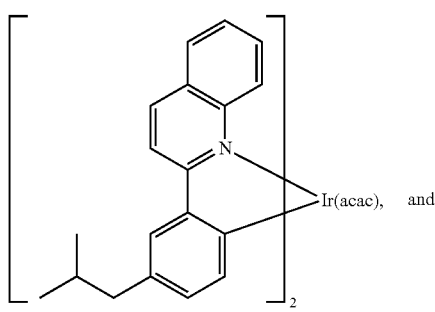

Compound 20

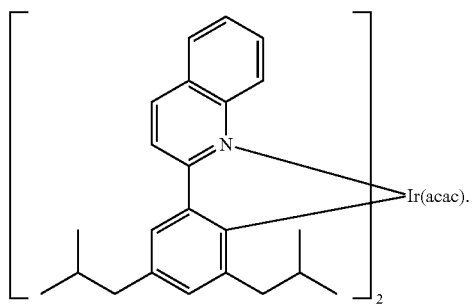

Compound 23

In another embodiment, a compound including a ligand has the formula:

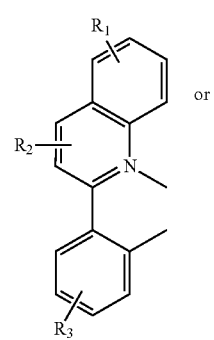

I' or

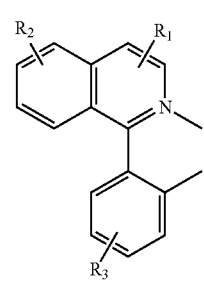

II' wherein each of $R_1$, $R_2$, and $R_3$ is independently a hydrogen, or a mono-, di-, tri-, tetra-, or penta-substitution of alkyl or aryl;

at least one of $R_1$, $R_2$, and $R_3$ is a branched alkyl containing at least 4 carbon atoms, and wherein the branching occurs at a position further than the benzylic position.

In one embodiment, the ligand is coordinated to a metal having an atomic number greater than 40. The metal can be any metal atom, including second and third row transition metals, lanthanides, actinides, main group metals, alkali metals, and alkaline earth metals. Heavy metals may provide thermal stability and superior phosphorescent properties. Second row transition metals include any of Zr, Nb, Mo, Tc, Ru, Rh, Pd, Ag, and Cd, and third row transition metals include any of La, Hf, Ta, W, Re, Os, Ir, Pt, Au, and Hg. Main group metals include, e.g., In, Sn, Sb, Tl, Pb, Bi, and Po. In some embodiments, M is Ir, Os, Pt, Pb, Re, or Ru. In other embodiments, the metal atom is Ir. The metal atom M can have any formal charge designated as m. In some embodiments, the formal charge is positive such as 1+, 2+, 3+, 4+, 5+, 6+, 7+, or 8+. In one embodiment, formal charge is greater than 1+. In another embodiment, formal charge is greater than 2+. In yet another embodiment, formal charge can be 3+.

In another embodiment, a compound is selected from the group consisting of:

Compound 1

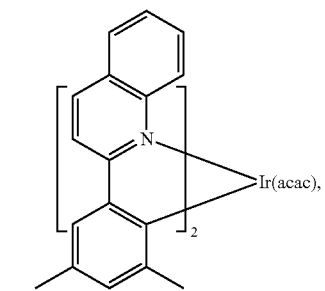

Compound 2

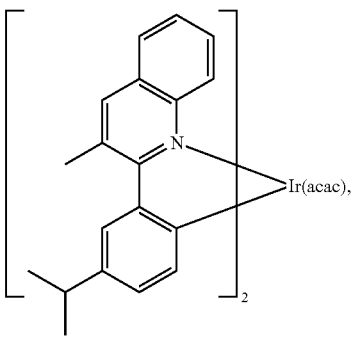

Compound 3

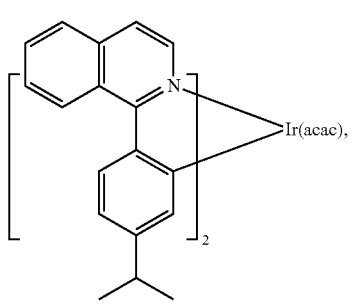

Compound 4

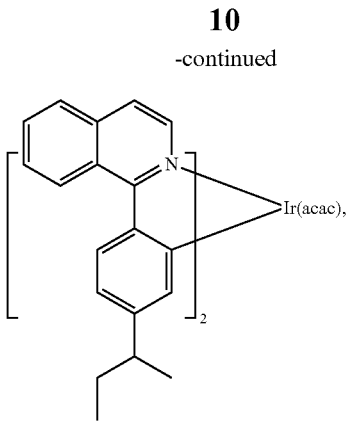

Compound 5

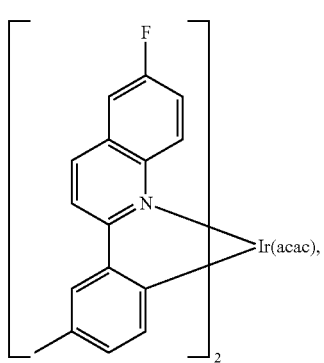

Compound 6

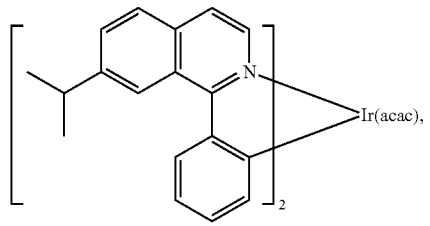

Compound 7

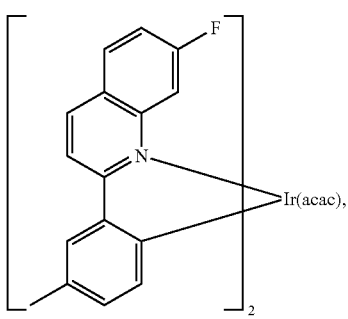

Compound 8

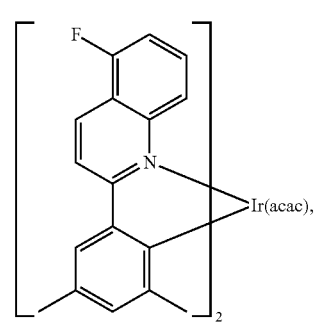

Compound 10
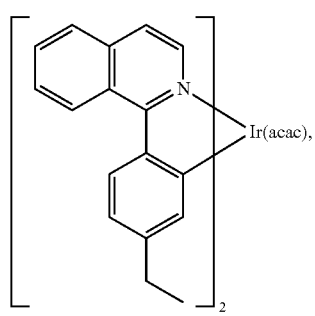
Compound 11
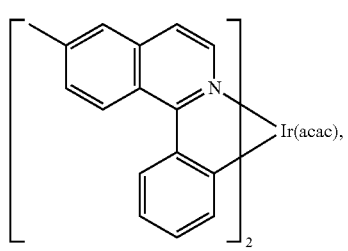
Compound 12
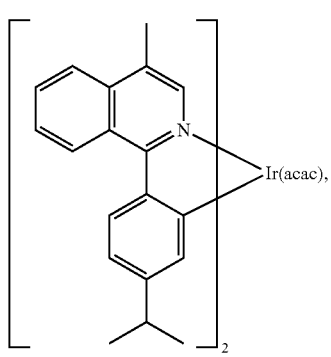
Compound 13
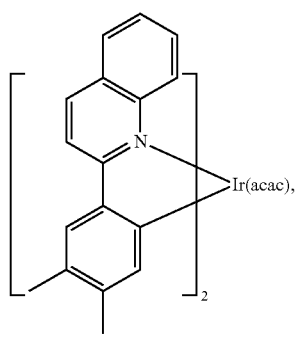
Compound 14
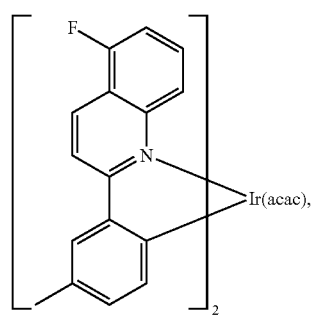
Compound 15
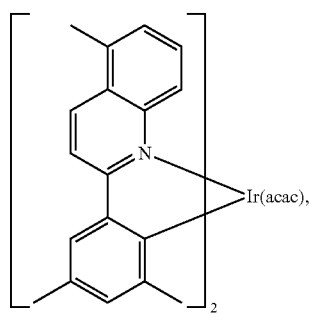
Compound 16
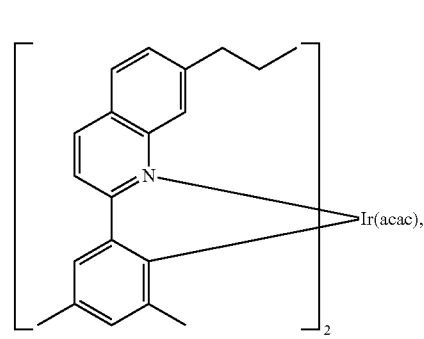
Compound 17
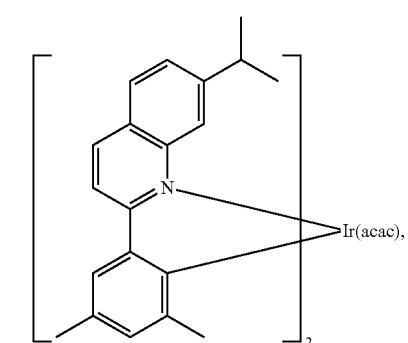
Compound 18
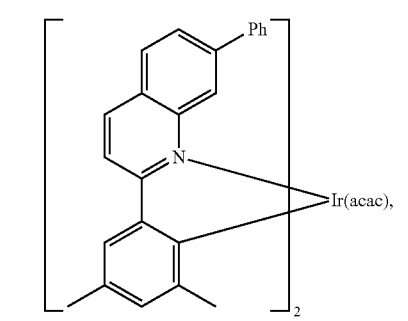
Compound 19
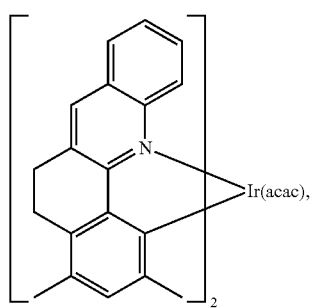

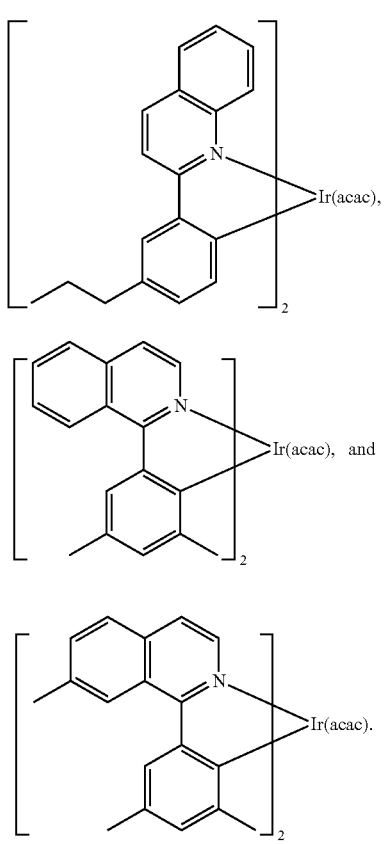

Compound 21

Compound 22

Compound 24

Some of the compounds provided can be photoluminescent. In some embodiments, the compounds are efficient phosphors having, for example, a significant portion of luminescence arising from phosphorescent emission. In some embodiments, the emission can be red or reddish. Color of emission can be estimated from the photoluminescence spectrum. A luminescence maximum of about 550 to about 700 nm can indicate red or reddish emission. A maximum at lower wavelengths can indicate green or blue emission. Additionally, the color of emission can be described by color index coordinates x and y (Commision Internationale de L'Eclairage (CIE) 1931 standard 2-degree observer; see, e.g., Shoustikov, et al., IEEE Journal of Selected Topics in Quantum Electronics, 1998, 4, 3; Dartnall, et al., Proceedings of the Royal Society of London B, 1983, 220, 115; Gupta, et al., Journal of Photochemistry, 1985, 30, 173; Colorimetry, 2.sup.nd ed., Publication CIE 15.2-1986 (ISBN 3-900-734-00-3)). For example, a compound emitting in the reds can have coordinates of about 0.5 to about 0.8 for x and about 0.2 to about 0.5 for y.

Some of the compounds provided may advantageously emit a more saturated hue, particular red. In other words, the compounds may emit a color that is closer to the pure spectral colors falling along the outside curve of the chromaticity diagram, i.e., colors that are produced by a single wavelength of light. The compounds may exhibit a narrower emission than other comparative compounds. Alternatively, the compounds may exhibit an emission profile that is closer to an industry standard hue for displays.

Processes for preparing compounds are also provided. Phenylquinolinato ligands (L) having desired substitutions can be made using the general procedure of coupling phenyl boronic acid having desired substitution with chloroquinoline (e.g., 2-chloroquinoline, 3-chloroisoquinoline, or 2-chloroisoquinoline) also having desired substitution. Coupling procedures can be, for example, conducted under Suzuki conditions in the presence of palladium(II) (see, e.g., Miyaura, et al., Chem. Rev. 1995, 2457). The quinoline (or isoquinoline) and boronic acid starting materials can be obtained from commercial sources or synthesized by methods known in the art. For example, 3-chloroisoquinoline can be made according to the procedures described in Haworth, R. D., et al., J Chem. Soc., 1948, 777.

Phenylquinoline ligands (L) having desired substitution can be coordinated to a metal atom by, for example, contacting the ligands with a metal halide complex. Metal halide complexes include compounds comprising at least one metal coordinated to one or more halide ligands. Metal halide complexes can be of the Formula $M(Q)_q$ where Q is a halide ligand and q is the number of halide ligands. For example, q can be about 2 to about 6. For the preparation of iridium-containing compounds, the metal halide complex can be $IrCl_3$. This and other metal halide complexes are well known in the art and commercially available. Under sufficient time and conditions, the contacting can result in the formation of a metal-containing intermediate, having mixed coordination of halide and phenylquinoline ligands L. In some embodiments, the metal atom of the intermediate can coordinate to at least one L. In other embodiments, the metal atom of the intermediate can coordinate two L. In further embodiments, the intermediate can be polynuclear comprising, for example, more than one metal atom and bridging halide ligands. When the metal halide complex is $IrCl_3$, the metal-containing intermediate can be an iridium dimer complex having, for example, the structure $L_2Ir(\mu\text{-}Cl)_2IrL_2$. Any remaining halide ligands of the intermediate, including bridging halides, can be replaced by ligand substitution with one or more ancillary ligands, such as represented by X and Y in Formula I or II. For example, 2,4-pentanedione in the presence of base can replace coordinated halide ligands in the metal-containing intermediate to give an acetylacetonato complex. Syntheses of exemplary compounds are provided in the Examples.

Some of the compounds provided can be used as emitters in organic light emitting devices. Accordingly, the compounds can be present in an emissive layer (i.e., a layer from which light is primarily emitted) of a such device. The emissive layer can be, for example, a layer consisting essentially of one or more of the compounds provided. Some of the compounds provided can also be present as dopants. For example, an emissive layer can comprise host material doped with one or more of the compounds provided. The host material can comprise any compound, including organic and organometallic compounds, suitable in an emissive layer in an OLED. Exemplary organic host materials include, but are not limited to, BCP (bathocuproine or 2,9-dimethyl-4,7-diphenyl-1,10-phenanthroline), CBP (4,4'-N,N'-dicarbazole biphenyl), OXD7 (1,3-bis(N,N-t-butyl-phenyl)-1,3,4-oxadiazole), TAZ (3-phenyl-4-(1'-naphthyl)-5-phenyl-1,2,4-triazole), NPD (4,4'-bis[N-(1-naphthyl)-N-phenyl-amino]biphenyl), CuPc (copper phthalocyanine), $Alq_3$ (aluminum tris(8-hydroxyquinolate)), and BAlq ((1,1'-biphenyl)-4-olato)bis(2-methyl-8-quinolinolato N1,O8)aluminum). Other materials that can be included in an emissive layer in addition to the emissive compounds include Irppy (tris(2-phenylpyridinato-N,C2')iridium(III)), FIrpic (bis(2-(4,6-difluorophenyl)pyridinato-N,C2')iridium(III)(picolinate)), and other metal complexes such as those described in U.S. Pat. No. 7,001,536; U.S. Pat. Nos. 6,911,271; and 6,939,624. As dopants, some of the compounds provided can be present in the emissive layer, such as in host material, in amounts of about 1 to about 20 wt %, about 5 to about 15 wt %, about 5 to about 10 wt %, or other similar ranges.

In one embodiment, specific combinations of dopants and hosts are provided. For example, the organic emissive layer can comprise BAlq or Compound C.

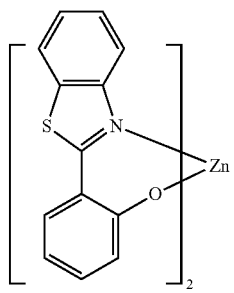

Compound C

In one embodiment, the organic emissive layer comprises Compound 1 and Compound C. In another embodiment, the organic emissive layer comprises Compound 9 and Compound C. In yet another embodiment, the organic emissive layer comprises Compound 22 and BAlq. In still another embodiment, the organic emissive layer comprises Compound 24 and BAlq.

Accordingly, in another embodiment, a composition comprises one or more of the compounds provided. In some embodiments, compositions comprise at least one of the compounds provided and a further compound suitable for use in an OLED. For example, further compounds can include any of the host materials mentioned above. Additionally, further compounds can include other emitters or metal complexes, such as FIrpic, Irppy, and other complexes mentioned above.

Devices comprising at least one of the compounds provided may have superior properties as compared with known devices. For example, high external quantum and luminous efficiencies can be achieved in the present devices. Device lifetimes are also generally better than, or at least comparable to, some of the most stable fluorescent devices reported.

Table 1 provides data for devices using exemplary compounds as well as devices using Comparative Examples 1 and 2:

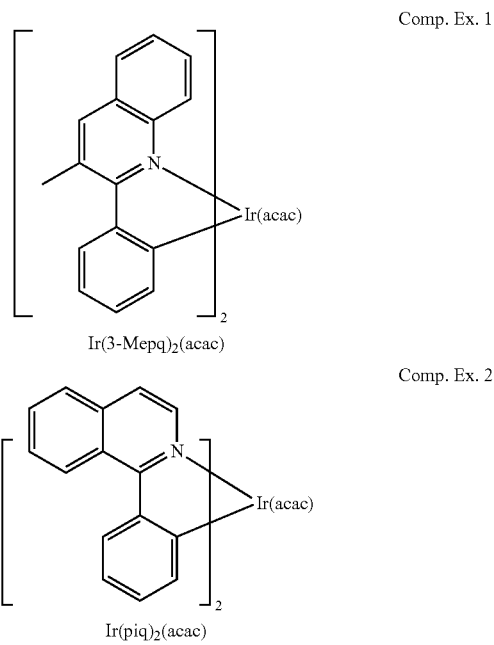

Ir(3-Mepq)$_2$(acac)

Ir(piq)$_2$(acac)

TABLE 1

| Dopant | Tsubl at 0.24 Å/s (° C.) | EML dopant % | λ max | FWHM (nm) | CIE | At 10 mA/cm$^2$ V (V) | LE (cd/A) | EQE (%) | LE:EQE | T$_{80\%}$ at 40 mA/cm$^2$ (hr) L$_0$ (cd/m$^2$) | RT | 70° C. | 70° C. Lifetime comparison (L$_0$)$^2$(T80%) at 70° C. (×10$^9$) |
|---|---|---|---|---|---|---|---|---|---|---|---|---|---|
| Comp. Ex. 1 | 206 | 12 | 622 | 94 | 0.65 0.35 | 8.1 | 14.3 | 14 | 1.01 | 4817 | 991 | 60 | 1.39 |
| Comp. Ex. 2 | 229 | 9 | 630 | 84 | 0.68 0.32 | 9.1 | 11.1 | 15 | 0.72 | 3808 | 1200 | 180 | 2.61 |
| 1 | 192 | 12 | 622 | 66 | 0.67 0.33 | 8.8 | 18.3 | 17.7 | 1.03 | 6382 | n.m. | 73 | 2.97 |
| 2 | 220 | 12 | 634 | 82 | 0.68 0.32 | 8.9 | 9.6 | 13.5 | 0.71 | 3308 | n.m. | 127 | 1.39 |
| 3 | 200 | 12 | 632 | 80 | 0.68 0.32 | 8.8 | 10.8 | 15.6 | 0.69 | 3784 | n.m. | 145 | 2.08 |
| 4 | 186 | 12 | 630 | 82 | 0.68 0.32 | 9.49 | 11.07 | 16 | 0.69 | 3852 | n.m. | 132 | 1.96 |
| 5 | 206 | 12 | 626 | 82 | 0.66 0.33 | 8.8 | 14.6 | 16.1 | 0.91 | 5175 | n.m. | 55 | 1.47 |
| 6 | 207 | 12 | 628 | 86 | 0.67 0.32 | 9 | 11.2 | 15.3 | 0.73 | 4007 | n.m. | 127 | 2.04 |
| 7 | 202 | 12 | 626 | 83 | 0.66 0.34 | 8.6 | 14.3 | 14 | 1.02 | 4877 | n.m. | 127 | 3.02 |
| 8 | 177-185 | 12 | 636 | 70 | 0.69 0.31 | 8.6 | 9.8 | 14.6 | 0.67 | 3390 | n.m. | 38 | 0.44 |
| 9 | 163-172 | 12 | 618 | 61 | 0.66 0.34 | 9.2 | 23.5 | 18.8 | 1.25 | 7992 | n.m. | 60 | 3.83 |
| 13 | 211 | 12 | 618 | 78 | 0.65 0.35 | 9.1 | 20.1 | 17.2 | 1.17 | 6865 | n.m. | 52 | 2.45 |
| 14 | 212 | 12 | 632 | 80 | 0.67 0.33 | 9.6 | 7.9 | 10.1 | 0.78 | 2810 | n.m. | 32 | 0.25 |
| 15 | 217 | 12 | 622 | 66 | 0.665 0.333 | 8.9 | 18.6 | 17.5 | 1.06 | 6411 | n.m. | 40 | 1.64 |
| 16 | 186 | 12 | 618 | 65 | 0.658 0.340 | 9.8 | 22.4 | 18.7 | 1.20 | 7593 | n.m. | 10.6 | 0.61 |
| 20 | 210 | 12 | 620 | 79 | 0.655 0.347 | 8.7 | 16.8 | 15.4 | 1.09 | 6026 | n.m. | 80 | 2.91 |
| 22 | 210 | 12 | 637 | 66 | 0.693 0.304 | 9.5 | 9.8 | 17.5 | 0.56 | 3277 | n.m. | 80 | 0.86 |
| 24 | 218 | 12 | 635 | 66 | 0.691, 0.306 | 8.9 | 11.5 | 19.0 | 0.61 | 3894 | n.m. | 90 | 1.36 | n.m. = not measured

As shown in Table 1, several exemplary compounds demonstrated efficiency and lifetime that was is better than, or at least comparable to, the comparative examples. For example, the LE and EQE of Compound 1 are 18.3 cd/A and 17.7%, respectively, at CIE of (0.67, 0.33). The LE:EQE ratio is 1.03, which is significantly higher than that of Comparative Example 2 (LE:EQE=0.72), which is only slightly more red (0.68, 0.32). The 70° C. lifetime comparison shows that Compound 1 is more stable than Comparative Example 2. Compound 1 is the best deep red emitter to date in the industry.

Some exemplary compounds also have high LE:EQE ratios compared to Comparative Examples 1 with similar CIE coordinates (0.65-0.66, 0.34-0.35) due to the narrow emission profile of the exemplary compounds. For example, Compound 9 has a deeper red CIE than Comparative Example 1, yet the LE:EQE ratio of Compound 9 is 1.25, which is significantly higher than that of Comparative Example 1 (1.01).

Table 2 shows data for devices using exemplary compounds as well as devices using Comparative Examples.

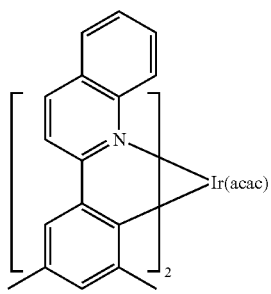

Compound 1

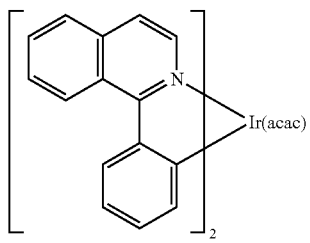

Comp. Ex. 5

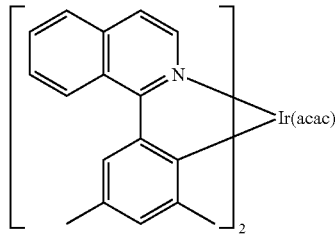

Compound 22

TABLE 2

| Dopant | Tsubl at 0.24 Å/s (° C.) | λ max | FWHM (nm) | CIE | At 10 mA/cm² | | | | $L_0$ (cd/m²) | $T_{80\%}$ at 40 mA/cm² (hr) | |
| --- | --- | --- | --- | --- | --- | --- | --- | --- | --- | --- | --- |
| | | | | | V (V) | LE (cd/A) | EQE (%) | LE:EQE | | RT | 70° C. |
| Comp. Ex. 3 | 200-210 | 602 | 78 | 0.61 0.38 | 8.5 | 27.1 | 16.6 | 1.63 | 9370 | 200 | n.m. |
| Comp. Ex. 4 | 237 | 618 | 78 | 0.65 0.34 | 8 | 9.8 | 8.8 | 1.11 | 3622 | 530 | n.m. |
| 1 | 192 | 622 | 66 | 0.67 0.33 | 8.8 | 18.3 | 17.7 | 1.03 | 6382 | n.m. | 73 |
| Comp. Ex. 5 | 229 | 632 | 84 | 0.68 0.32 | 8.8 | 10.6 | 15.2 | 0.70 | 3757 | n.m. | 240 |
| 22 | 210 | 637 | 66 | 0.693 0.304 | 9.5 | 9.8 | 17.5 | 0.56 | 3277 | n.m. | 80 |

As shown by Table 2, Compound 1 has lower sublimation temperature, higher efficiency, and narrower emission compared with Comparative Examples 3 and 4. Similarly, Compound 22 has a lower sublimation temperature, higher efficiency, and narrower emission compared with Comparative Example 5.

Compounds having branched alkyl substitution may be particular advantageous. Branched alkyl substitutions on red compounds seem to improve lineshape, efficiency, and lifetime. Table 3 shows data for devices using exemplary compounds, including those having branched alkyl substitutions, as well as devices using Comparative Examples.

Comp. Ex. 6

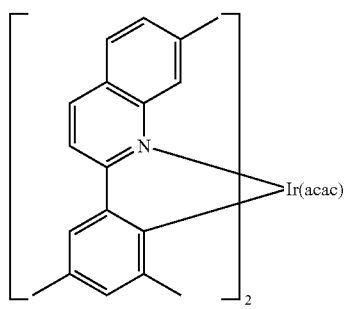

Compound 9

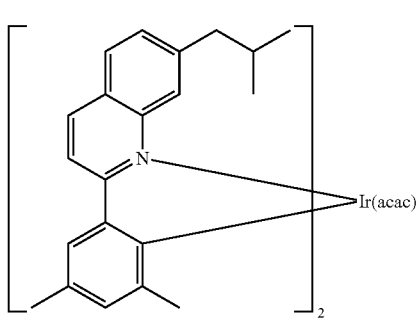

Compound 16

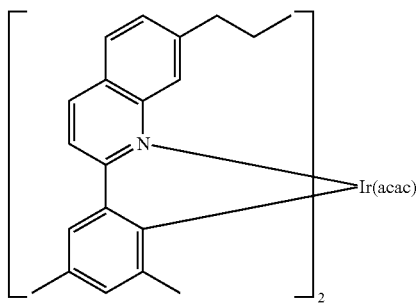

Compound 20

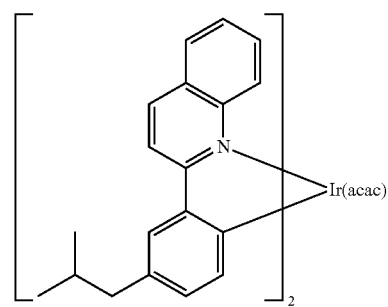

Comp. Ex. 7

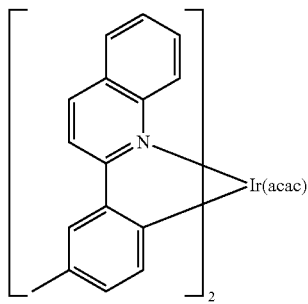

TABLE 3

| Dopant | Tsubl at 0.24 Å/s (° C.) | λ max | FWHM (nm) | At 10 mA/cm² | | | | | L₀ | T₈₀% at 40 mA/cm² (hr) | |
|---|---|---|---|---|---|---|---|---|---|---|---|
| | | | | CIE | V (V) | LE (cd/A) | EQE (%) | LE:EQE | (cd/m²) | RT | 70° C. |
| Comp. Ex. 6 | 190 | 618 | 64 | 0.66 0.34 | 8.7 | 20 | 16.8 | 1.19 | 7014 | n.m. | 31 |
| 9 | 198 | 618 | 61 | 0.66 0.34 | 9.2 | 23.5 | 18.8 | 1.25 | 7992 | n.m. | 60 |
| 16 | 186 | 618 | 65 | 0.658 0.340 | 9.8 | 22.4 | 18.7 | 1.20 | 7593 | n.m. | 10.6 |
| 20 | 210 | 620 | 79 | 0.655 0.347 | 8.7 | 16.8 | 15.4 | 1.09 | 6026 | n.m. | 80 |
| Comp. Ex. 7 | 237 | 618 | 78 | 0.65 0.34 | 8 | 9.8 | 8.8 | 1.11 | 3622 | 530 | n.m. |

As shown by Table 3, isobutyl substitutions on either quinoline or phenyl ring resulted in higher efficiency and longer lifetime. Compared to methyl and n-propyl substitution on the 7 position of quinoline, the isobutyl substitution maintained the emission maximum. However, the spectrum is narrower than methyl or n-propyl substitution. The full width of half maxima (FWHM) decreased to 61 nm, which resulted in a higher ratio of current efficiency to external quantum efficiency. In addition, isobutyl substitution shows much longer lifetime than methyl and n-propyl substitution.

When the methyl group was replaced by isobutyl group on the phenyl ring (see Compound 20 and Comparative Example 7), the evaporation temperature decreased by 27 degrees. The emission slightly shifted to a more saturated red color. Again, the external quantum efficiency increased from 8.8% to 15.4%.

In some embodiments, e.g., those comprising Ir, the device emits red. Red devices can have electroluminescence maxima of about 550 to about 700 nm. Similarly, color index coordinates (CIE) for red devices can be about 0.5 to about 0.8 for x and about 0.2 to about 0.5 for y. In some embodiments, devices, e.g., red devices, can have external quantum efficiencies greater than about 4%, 5%, 6%, 7%, 8%, 10%, 12%, or higher at a brightness greater than about 10, 100, 1000 $cd/m^2$, or more.

Typical devices are structured so that one or more layers are sandwiched between a hole injecting anode layer and an electron injecting cathode layer. The sandwiched layers have two sides, one facing the anode and the other facing the cathode. Layers are generally deposited on a substrate, such as glass, on which either the anode layer or the cathode layer may reside. In some embodiments, the anode layer is in contact with the substrate. In some embodiments, for example when the substrate comprises a conductive or semi-conductive material, an insulating material can be inserted between the electrode layer and the substrate. Typical substrate materials may be rigid, flexible, transparent, or opaque, and include, but are not limited to, glass, polymers, quartz, and sapphire.

In some embodiments, devices comprise further layers in addition to a layer comprising at least one of compounds provided (e.g., an emissive layer). For example, in addition to the electrodes, devices can include any one or more of hole blocking layers, electron blocking layers, exciton blocking layers, hole transporting layers, electron transporting layers, hole injection layers, and electron injection layers. Anodes can comprise an oxide material such as indium-tin oxide (ITO), Zn—In—$SnO_2$, $SbO_2$, or the like, and cathodes can comprises a metal layer such as Mg, Mg:Ag, or LiF:Al. Among other materials, the hole transporting layer (HTL) can comprise triaryl amines or metal complexes such as those described in U.S. Pat. No. 7,261,954. Similarly, the electron transporting layer (ETL) can comprise, for example, aluminum tris(8-hydroxyquinolate) ($Alq_3$) or other suitable materials. Additionally, a hole injection layer can comprise, for example, 4,4',4"-tris(3-methylphenylphenylamino)triphenylamine (MTDATA), polymeric material such as poly(3,4-ethylenedioxythiophene) (PEDOT), metal complex such as copper phthalocyanine (CuPc), or other suitable materials. Hole blocking, electron blocking, and exciton blocking layers can comprise, for example, BCP, BAlq, and other suitable materials such as FIrpic or other metal complexes described in U.S. Pat. No. 7,261,954. Some of the compounds provided can also be included in any of the above mentioned layers.

Light emitting devices can be fabricated by a variety of well-known techniques. Small molecule layers, including those comprised of neutral metal complexes, can be prepared by vacuum deposition, organic vapor phase deposition (OVPD), such as disclosed in U.S. Pat. No. 6,337,102, or solution processing such as spin coating. Polymeric films can be deposited by spin coating and chemical vapor deposition (CVD). Layers of charged compounds, such as salts of charged metal complexes, can be prepared by solution methods such a spin coating or by an OVPD method such as disclosed in U.S. Pat. No. 5,554,220. Layer deposition generally, although not necessarily, proceeds in the direction of the anode to the cathode, and the anode typically rests on a substrate. Devices and techniques for their fabrication are described throughout the literature, e.g., U.S. Pat. Nos. 5,703,436; 5,986,401; 6,013,982; 6,097,147; and 6,166,489. For devices from which light emission is directed substantially out of the bottom of the device (i.e., substrate side), a transparent anode material such as ITO may be used as the bottom electron. Since the top electrode of such a device does not need to be transparent, such a top electrode, which is typically a cathode, may be comprised of a thick and reflective metal layer having a high electrical conductivity. In contrast, for transparent or top-emitting devices, a transparent cathode may be used such as disclosed in U.S. Pat. Nos. 5,703,436 and 5,707,745. Top-emitting devices may have an opaque and/or reflective substrate, such that light is produced substantially out of the top of the device. Devices can also be fully transparent, emitting from both top and bottom.

Transparent cathodes, such as those used in top-emitting devices preferably have optical transmission characteristics such that the device has an optical transmission of at least about 50%, although lower optical transmissions can be used. In some embodiments, devices include transparent cathodes having optical characteristics that permit the devices to have optical transmissions of at least about 70%, 85%, or more. Transparent cathodes, such as those described in U.S. Pat. Nos. 5,703,436 and 5,707,745, typically comprise a thin layer of metal such as Mg:Ag with a thickness, for example, that is less than about 100 Å. The Mg:Ag layer can be coated with a transparent, electrically-conductive, sputter-deposited ITO layer. Such cathodes are often referred to as compound cathodes or as TOLED (transparent-OLED) cathodes. The thickness of the Mg:Ag and ITO layers in compound cathodes may each be adjusted to produce the desired combination of both high optical transmission and high electrical conductivity, for example, an electrical conductivity as reflected by an overall cathode resistivity of about 30 to 100 ohms per square. However, even though such a relatively low resistivity can be acceptable for certain types of applications, such a resistivity can still be somewhat too high for passive matrix array OLED pixels in which the current that powers each pixel needs to be conducted across the entire array through the narrow strips of the compound cathode.

Light emitting devices can be used in a pixel for an electronic display. Virtually any type of electronic display can incorporate the devices. Displays include, but are not limited to, computer monitors, televisions, personal digital assistants, printers, instrument panels, and bill boards. In particular, the devices can be used in flat-panel displays and heads-up displays.

The following examples are illustrative only and are not intended to be limiting. Those skilled in the art will recognize, or be able to ascertain through routine experimentation, numerous equivalents to the specific substances and procedures described herein. Such equivalents are considered to be within the scope of the claimed invention. All references named herein are expressly and entirely incorporated by reference.

Examples

In the exemplary syntheses described herein, the following reagents are abbreviated as follows:
DME 1,2-dimethoxyethane
$Pd_2(dba)_3$ Tris(dibenzylideneacetone)dipalladium
$Pd(OAc)_2$ Palladium acetate
$Pd(PPh_3)_4$ Tetrakis(triphenylphosphine)palladium
$Ph_3P$ Triphenylphosphine
$RuCl_2(PPh_3)_3$ Dichlorotris(triphenylphosphine)ruthenium (III)
THF Tetrahydrofuran Synthesis of Compound 1

Step 1

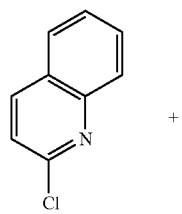
+
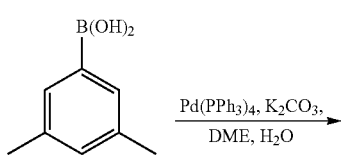

To a 500 mL round bottle flask, 9.0 g (~54.4 mmol) of 2-chloroquinoline, 9.2 g (59.8 mmol) of 3,5-dimethylphenylboronic acid, 1.8 g (1.5 mmol) of $Pd(PPh_3)_4$, 22.4 g (163 mmol) of $K_2CO_3$, 150 mL of DME, and 150 mL of water were charged. The reaction mixture was heated to reflux under nitrogen overnight. The reaction mixture was cooled, and the organic extracts were purified by a silica gel column chromatography (10% ethyl acetate in hexane as eluent). The material obtained was further purified by vacuum distillation (Kugelrohr) at 185° C. to yield 12.2 g (95% yield) of product as a colorless liquid.

Step 2

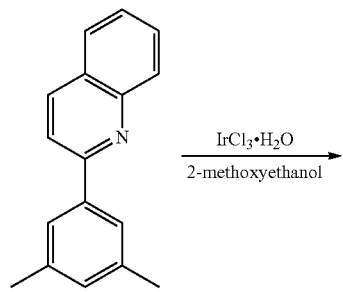

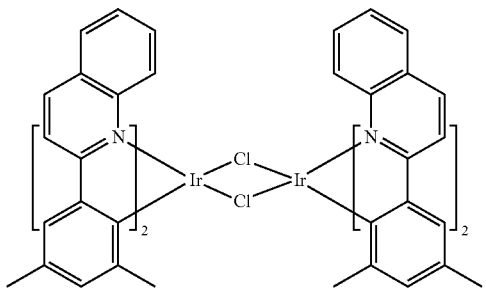

46 g (197.4 mmol) of the product from Step 1, 536 mL of 2-methoxyethanol, and 178 mL of water were charged in a 1000 mL three-neck flask. The reaction mixture was bubbled with nitrogen for 45 min with stirring. Then 32 g (86.2 mmol) of $IrCl_3.H_2O$ was added into this mixture and heated to reflux (100-105° C.) under nitrogen for 17 hrs. The reaction mixture was cooled and filtered. The black-gray solid was washed with methanol (4×150 mL) followed by hexane (3×300 mL). 36.5 g of the dimer was obtained after drying in a vacuum oven. The dimer was used for the next step without further purification.

Step 3

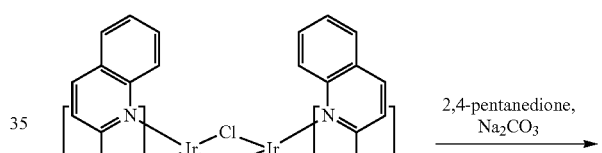

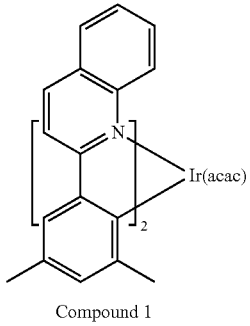

Compound 1

36 g of the dimer (26 mmol), 120 g of 2,4-pentanedione (~1200 mmol), 66 g (622 mmol) of sodium carbonate, and about 500 mL of 2-methoxyethanol were added in a 1000 mL round bottle flask. The reaction mixture was vigorously stirred at room temperature for 24 hrs. The reaction mixture was then suction filtered and washed with methanol (3×250 mL) followed by hexane (4×300 mL) The solid was collected and stirred in ~1000 mL of a solvent mixture (900 mL of methylene chloride and 100 mL of triethylamine) for ~10 min. Then the mixture was gravity filtered with a Whatman Quality 1 Circle filter paper. ~20 g of red final product (52% yield) was obtained after evaporating the solvent in the filtrate (99.5% pure with non-acidic HPLC column).

Synthesis of Compound 2
Step 1

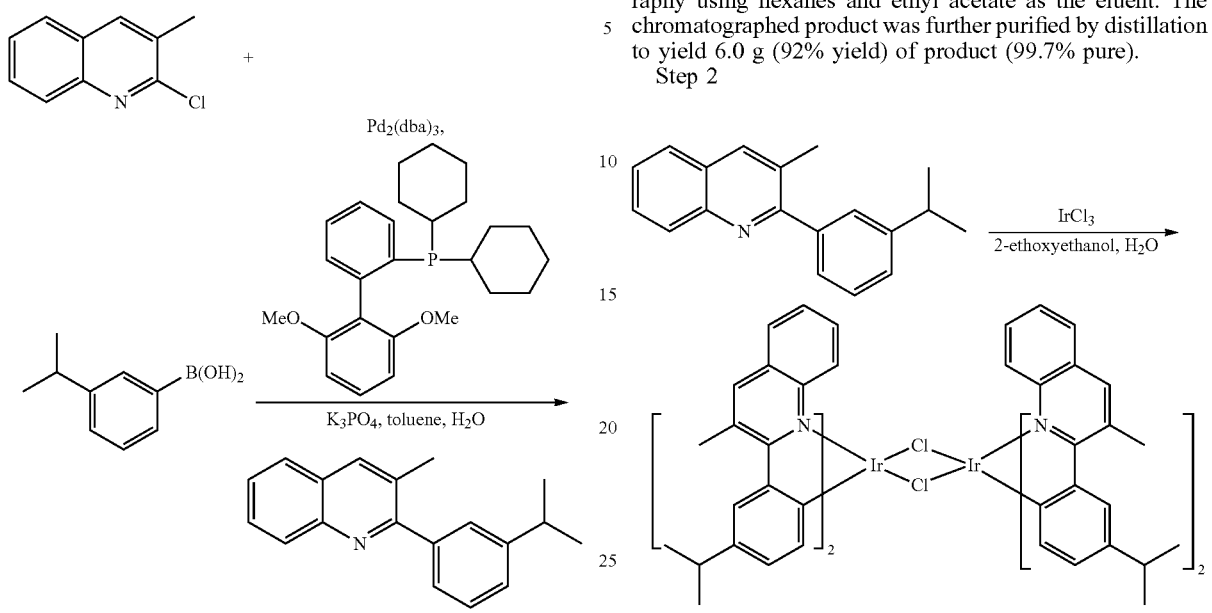

4.5 g (25 mmol) of 2-chloro-3-methyl-quinoline, 5.0 g (30 mmol) of 3-isopropylphenylboronic acid, 17.3 g (75 mmol) of potassium phosphate monohydrate, 0.4 g (1.0 mmol) of 2-dicyclohexylphosphino-2',6'-dimethoxybiphenyl, 100 mL of toluene, and 25 mL of water were added to a 250 mL three-neck flask. The system was purged with nitrogen for 30 min before 0.23 g (0.25 mmol) of $Pd_2(dba)_3$ was added to the mixture. The reaction mixture was then heated to reflux for 3 hrs. After cooled to room temperature, the layers were separated. The aqueous layer was extracted with ethyl acetate. The organic layers were combined, washed with water, and dried over magnesium sulfate. After evaporating the solvent, the residue was purified by column chromatography using hexanes and ethyl acetate as the eluent. The chromatographed product was further purified by distillation to yield 6.0 g (92% yield) of product (99.7% pure).

Step 2

5.4 g (20.7 mmol) of the product from Step 1 and 3.2 g (9.0 mmol) of iridium chloride were mixed in 90 mL of 2-ethoxyethanol and 30 mL of water. The mixture was heated to reflux overnight. The solvent was evaporated. 60 mL of 2-ethoxyethanol was added, and the mixture was heated to reflux for another 40 hrs. After cooled to room temperature, the solid was collected by filtration. 3.2 g of the dimer was obtained. The dimer was used for the next step without further purification.

Step 3

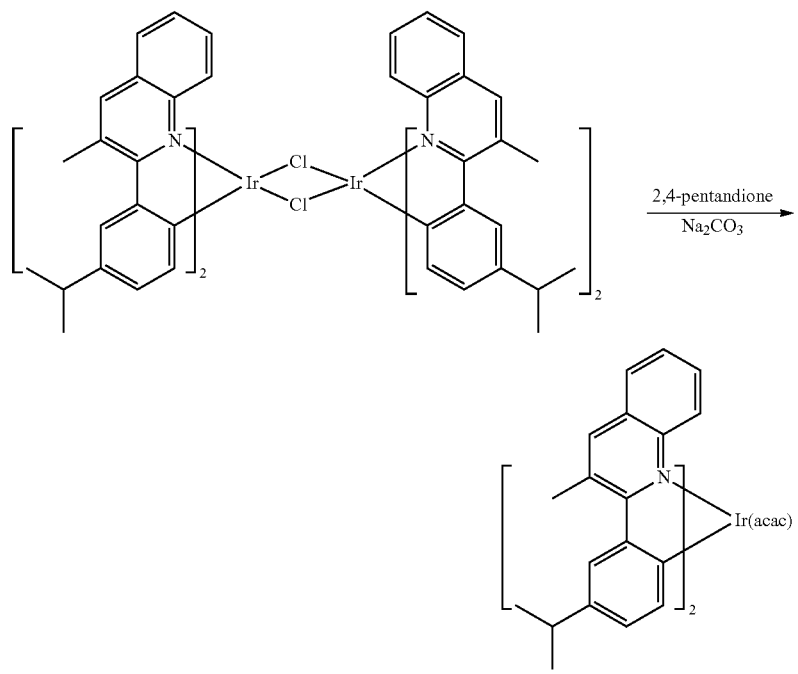

Compound 2

3.2 g of the dimer, 10 mL of 2,4-pentanedione, and 2.5 g of sodium carbonate were added to 50 mL of 1,2-dichloroethane and heated to reflux overnight. After cooled to room temperature, the mixture was filtered. The filtrate was concentrated and run through a triethylamine treated silica gel column. The final compound was sublimed twice, yielding 0.63 g of 98.7% pure product.

Synthesis of Compound 3

Step 1

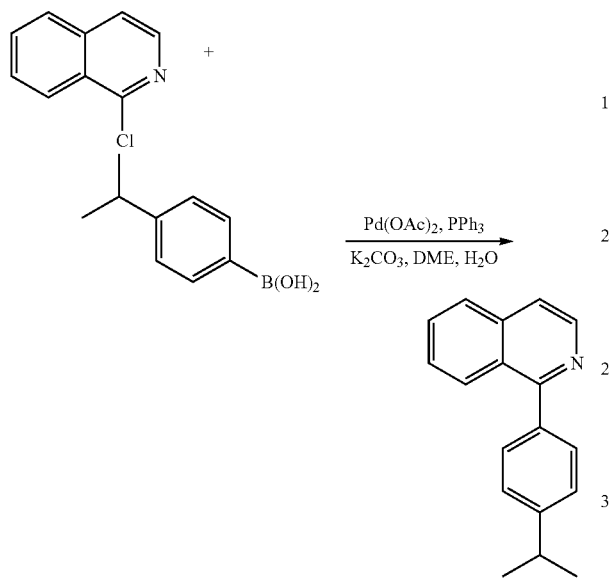

A mixture of 1-chloroisoquinoline (5.0 g, 30.56 mmol), 4-isopropylphenylboronic acid (5.5 g, 33.62 mmol), Pd(OAc)$_2$ (0.34 g, 1.53 mmol), Ph$_3$P (1.60 g, 6.11 mmol), and K$_2$CO$_3$ (10.98 g, 79.46 mmol) in 25 mL water and 25 mL of 1,2-dimethoxyethane was stirred and purged with nitrogen for 30 min. The mixture was heated to reflux overnight under nitrogen. The reaction mixture was cooled to room temperature, and water was added, followed by ethyl acetate. The layers were separated, and the aqueous layer was extracted with ethyl acetate. The organic extracts were washed with water, brine, dried over magnesium sulfate, filtered, and evaporated. The residue was purified by column chromatography eluting with 0, 5, and 10% ethyl acetate/hexanes. The chromatographed product was purified by distillation using a Kugelrohr at 180° C. to yield 5.56 g (74% yield) of the product as a clear oil.

Step 2

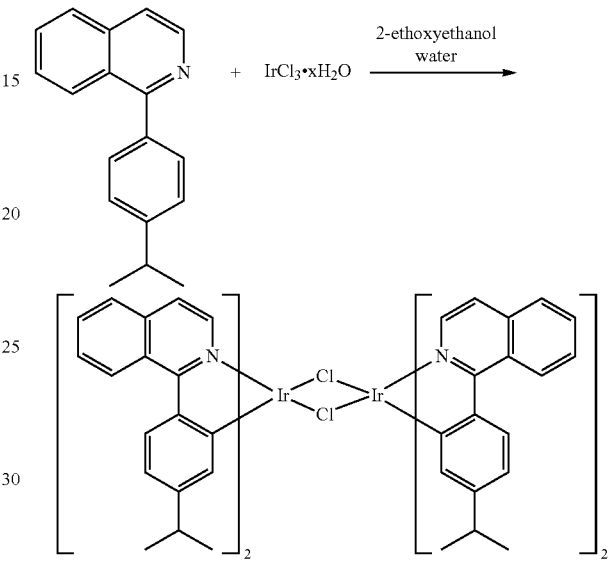

A mixture of the ligand from Step 1 (5.56 g, 22.48 mmol), iridium chloride (3.78 g, 10.2 mmol), 2-ethoxyethanol (45 mL), and 15 mL of water was refluxed overnight under nitrogen. The mixture was cooled to room temperature, and the solid was filtered, washed with methanol, dried, and used without further purification.

Step 3

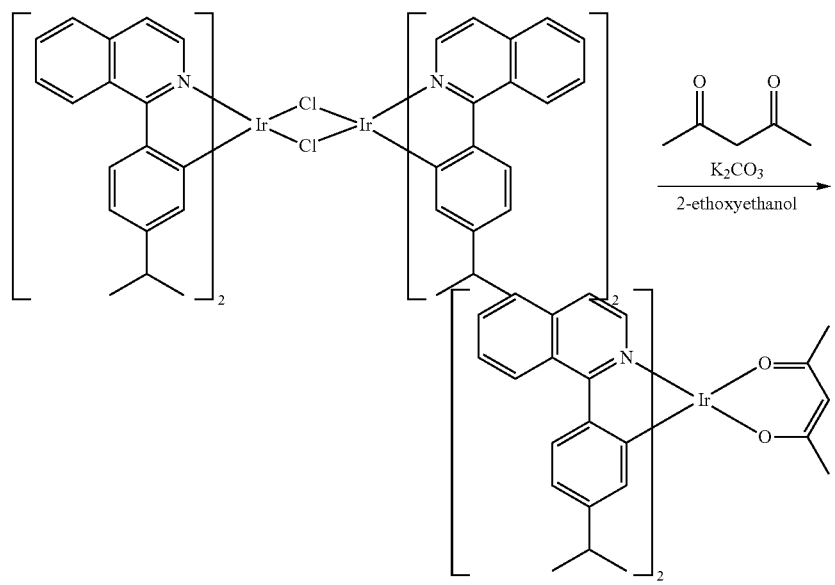

A mixture of the dimer, 2,4-pentanedione (10.5 mL, 102 mmol), and K$_2$CO$_3$ (4.23 g, 30.6 mmol) in 75 mL of 2-ethoxyethanol was refluxed overnight under nitrogen. The reaction was cooled to room temperature and methanol was added. A red solid was filtered off and washed with methanol. The solid was purified by column chromatography. The column was treated with 20% triethylamine/hexanes prior to purification, then eluted with 20 and 50% dichloromethane/hexanes after loading the solid to the column. 4.2 g (53% yield) of a red solid was obtained as the product, which was further purified by recrystallization from acetonitrile followed by sublimation at 250° C.

Synthesis of Compound 4

Step 1

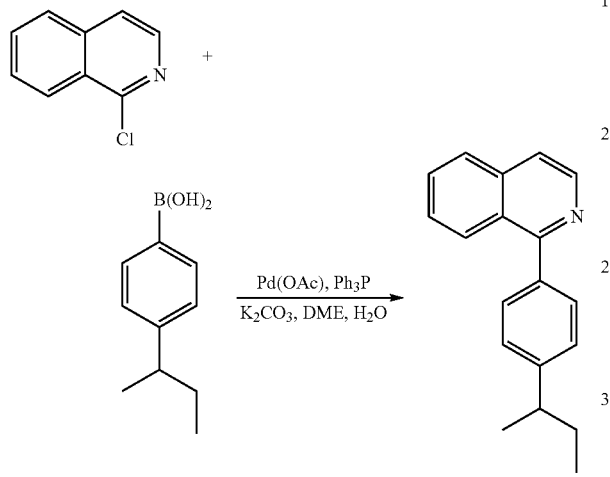

1-chloroisoquinoline (2.95 g, 18.00 mmol) was dissolved in 25 mL of DME and 25 mL of water. 4-sec-butylphenylboronic acid (3.36 g, 18.90 mmol), Ph$_3$P (0.94 g, 3.60 mmol), and K$_2$CO$_3$ (7.46 g, 54.01 mmol) were added, and the mixture was stirred and purged with nitrogen for 30 min. Pd(OAc)$_2$ (0.20 g, 0.90 mmol) was added, and the mixture was refluxed overnight. The product was extracted with ethyl acetate, washed with water, and dried over sodium sulfate. Chromatography (0-20% ethyl acetate/hexanes) yielded a light yellow oil. Further purification by Kugelrohr distillation at 185° C. gave 2.52 g the product as a clear oil.

Step 2

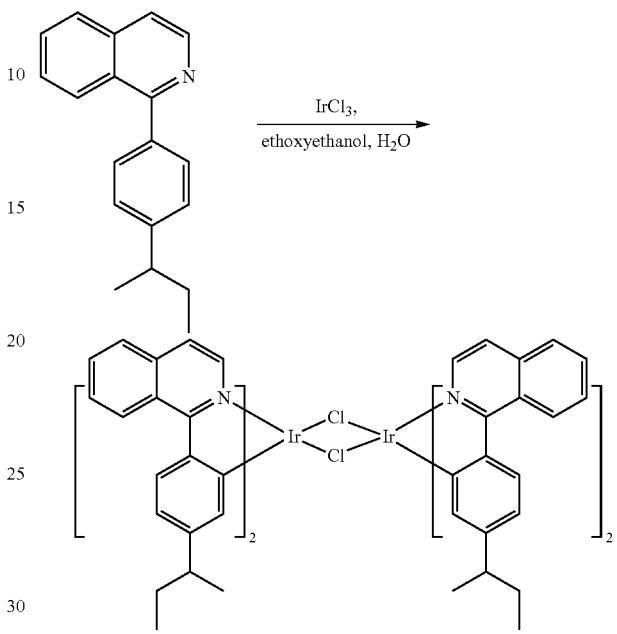

The ligand from Step 1 (2.52 g, 9.64 mmol) was combined with iridium chloride (1.62 g, 4.38 mmol) in 40 mL of 3:1 ethoxyethanol:water and refluxed for 24 hrs. The mixture was cooled to room temperature, and the solid was filtered, washed with methanol, dried, and used without further purification.

Step 3

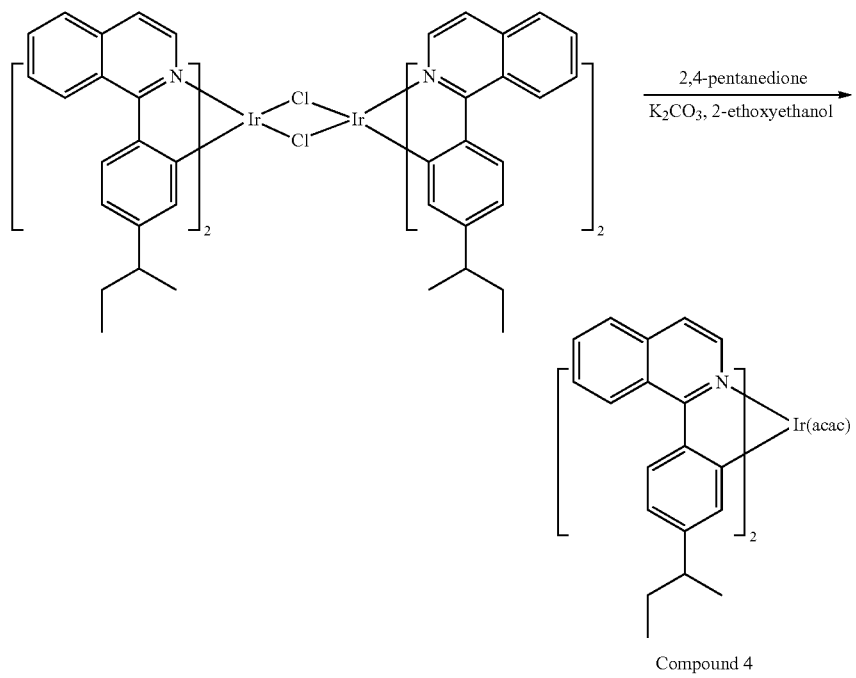

Compound 4

The dimer was suspended in 25 mL of ethoxyethanol. 2,4-pentanedione (4.51 mL, 43.83 mmol) and K$_2$CO$_3$ (1.82 g, 13.15 mmol) were added, and the reaction was refluxed overnight. After cooling the mixture was poured into a large excess of stirring methanol. A red precipitate was filtered and purified by column chromatography (column pretreated with 20% triethylamine/hexanes, run with 0-20% dichloromethane/hexanes) to give red solids, which were further purified by recrystallization from acetonitrile followed by sublimation at 200° C., yielding 0.41 g of product (99.1% pure).

Synthesis of Compound 5

Step 1

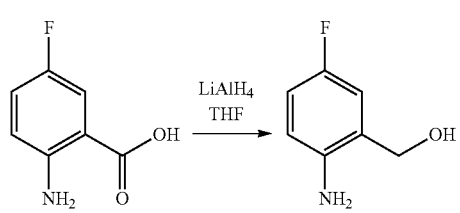 [SMILES: Nc1ccc(F)cc1C(=O)O ; Nc1ccc(F)cc1CO]

2-Amino-5-fluorobenzoic acid (10.0 g, 64.46 mmol) was dissolved in 50 mL of THF and cooled to 0° C. 1.0 M of lithium aluminum hydride in THF (79.93 mL, 79.93 mmol) was added dropwise. The mixture was allowed to warm to room temperature and stirred for 6 hrs. The reaction was placed in an ice bath and 3 mL of water was added dropwise. 50 mL of 1.0 N NaOH was added dropwise and stirred for 15 min. 50 mL of water was added and stirred for 15 min. The mixture was extracted with ethyl acetate, washed with water, and concentrated to a volume of about 100 mL. This was then poured into a large excess of stirring hexanes. The precipitate that formed was filtered, washed with hexanes, and dried under vacuum to yield 6.71 g of off-white solids as the product.

Step 2

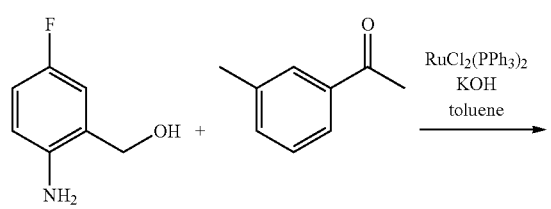

The product from Step 1 (6.71 g, 47.56 mmol) was combined with 3-methylacetophenone (11.28 g, 84.13 mmol), RuCl$_2$(PPh$_3$)$_3$ (0.05 g, 0.05 mmol), and potassium hydroxide (0.83 g, 0.02 mmol) in 70 mL of toluene and refluxed overnight using a Dean-Stark trap to remove water. The reaction was cooled to room temperature, and a small amount of Celite was added to the mixture, which was then filtered through a silica gel plug. The filtrate was concentrated. Purification was achieved by chromatography (5% ethyl acetate/hexanes) and vacuum distillation at 200° C. to yield 6.59 g of yellow solids as the product.

Step 3

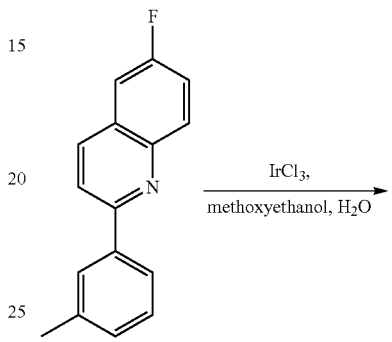

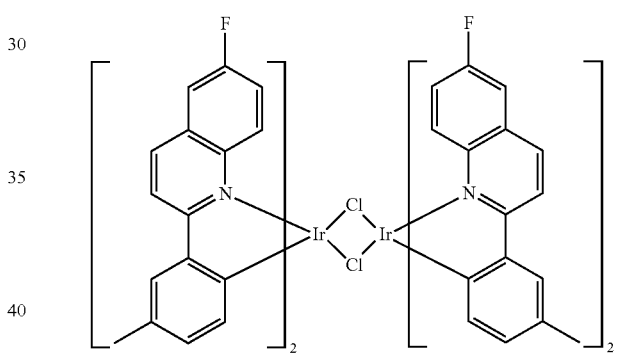

The ligand from Step 2 (6.59 g, 26.22 mmol) was combined with iridium chloride (4.41 g, 11.92 mmol) in 80 mL of a 3:1 methoxyethanol:water solution. The mixture was purged with nitrogen for 20 min and refluxed overnight. The dark red precipitate that formed was filtered off, washed with methanol and hexanes, and used for the next step without further purification.

Step 4

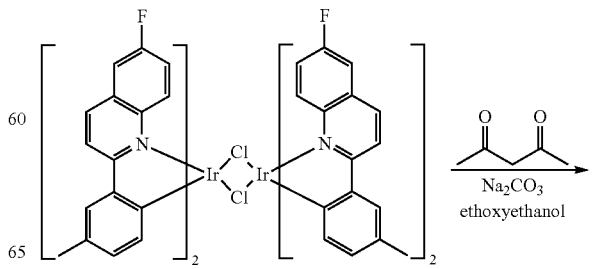

-continued

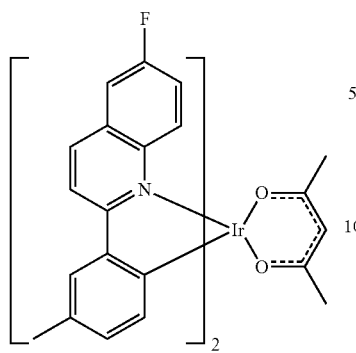

The dimer (17.39 g, 11.92 mmol) was suspended in 50 mL of ethoxyethanol. 2,4-pentanedione (12.28 mL, 119.20 mmol), and sodium carbonate (3.79 g, 35.76 mmol) were added, and the reaction was stirred overnight at room temperature. The mixture was poured into a large excess of stirring methanol. A red precipitate formed and was filtered off. This precipitate was dissolved in dichloromethane, poured into stirring methanol, and filtered to give a red solid. This procedure was repeated. This solid was dried under vacuum to yield 4.40 g of red solid as the product, which was further purified by two sublimations yielding 3.21 g (99.9% pure).

Synthesis of Compound 6

Step 1

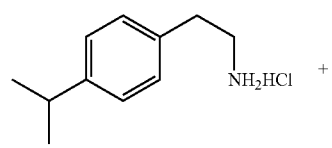

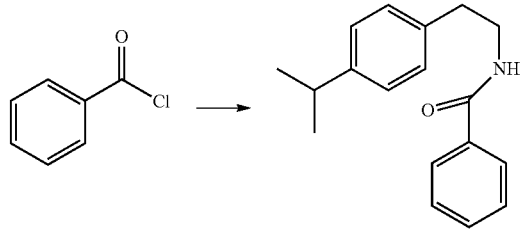

5.9 g (0.075 mol) of pyridine and 5 g (0.025 mol) 4-isopropylphenylethylamine hydrochloride were added to a three-neck round-bottom flask with 25 mL of dichloromethane as the solvent. The solution was cooled in an ice bath, and 3.2 mL (0.027 mol) of benzoyl chloride was added slowly via a syringe. The solution was warmed to room temperature and stirred for 12 hrs. Dichloromethane was added, and the organic phase was washed with water, 5% HCl solution, 5% NaOH solution, and dried over MgSO₄. The solvent was evaporated resulting in 7.5 g of crude product, which was used without further purification.

Step 2

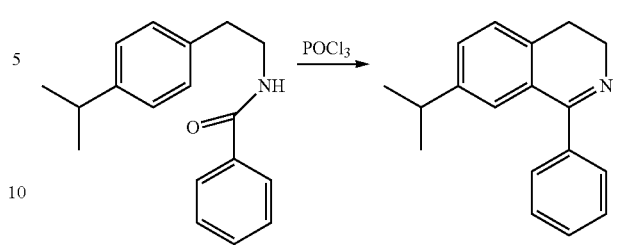

N-(4-p-isopropylphenylethyl)benzamide (7.5 g), 25 g phosphorous pentoxide, and 25 mL of phosphorous oxychloride in 80 mL of xylenes were refluxed for 3 hrs. After cooling, the solvent was decanted, and ice was slowly added to the solid. The water-residue mixture was made weakly alkaline with 50% NaOH, and the product was extracted with toluene. The organic layer was washed with water and dried over MgSO₄. The solvent was evaporated resulting in 6.2 g of crude product, which was used without further purification.

Step 3

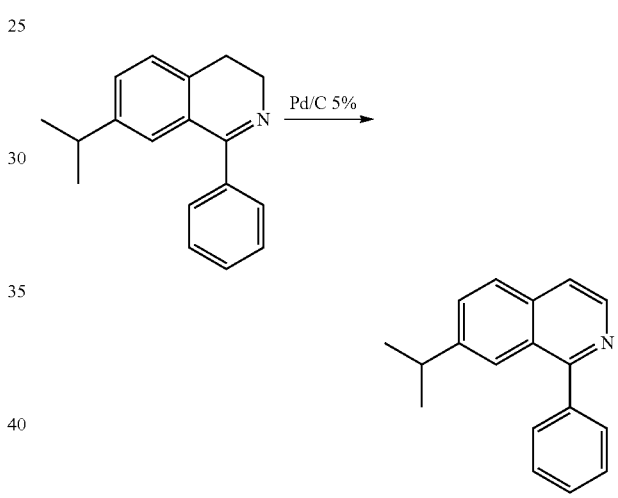

6.2 g of 7-isopropyl-1-phenyl-3,4-dihydroisoquinoline and 1 g of 5% Pd/C (~10% by weight) were added to a round-bottom flask with 100 mL of xylenes. The solution was refluxed for 24 hrs, and the formation of the product was monitored by TLC. The xylenes solvent was removed, and the product was purified by column chromatography with ethyl acetate/hexanes. The pure fractions were collected, and the solvent was removed. The product was then distilled in a Kugelrohr apparatus at 185° C. affording 1.8 g (0.0073 mol) of pure product. The overall yield of ligand formation was ~15%.

Step 4

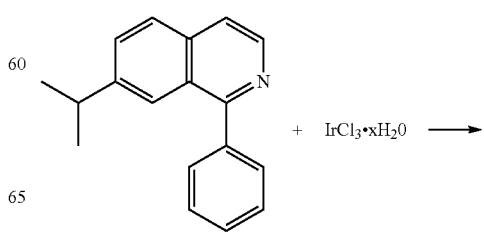

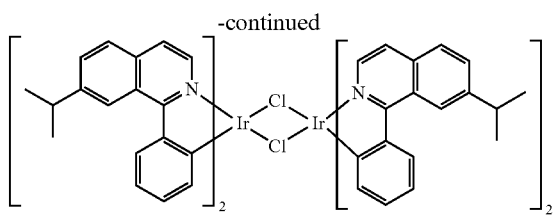

A mixture of 1.8 g of the 1-phenyl-7-isopropylisoquinoline ligand (0.0073 mol) and 1.2 g of IrCl$_3$ (0.0036 mol) in 25 mL of 2-ethoxyethanol and 5 mL of water was refluxed for 18 hrs. Upon cooling, the red solid dimer was filtered and washed with 300 mL of methanol resulting in 1.3 g (25% yield) of crude product.
Step 5

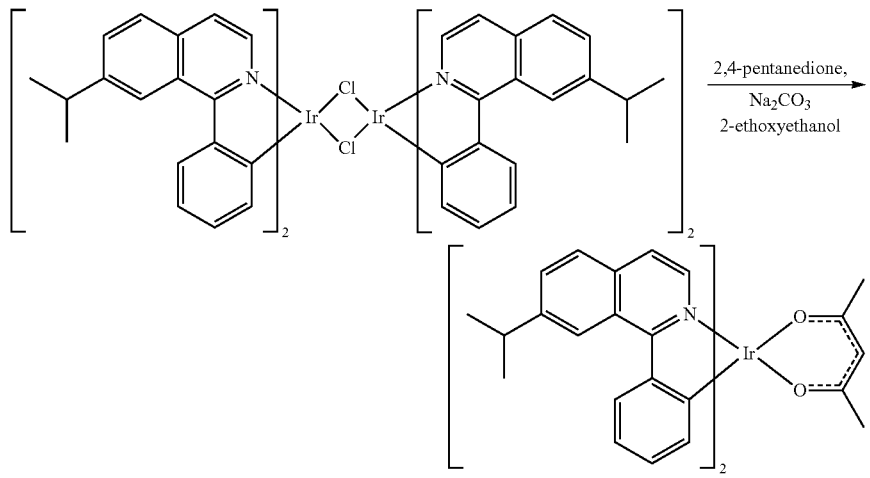

Compound 6

1.3 g of the dimer (0.0009 mol), 2 mL of 2,4-pentandione, and 1 g of sodium carbonate were added to a flask with 25 mL of 2-ethoxyethanol. The solution was refluxed for 12 hrs. After cooling, the product was run through a Celite plug with dichloromethane as the solvent. The solvent was removed, and the product was precipitated from 2-ethoxyethanol by adding water. The compound was dissolved in dichloromethane, dried with MgSO$_4$, filtered, and the solvent was evaporated. The compound was purified by column chromatography using dichloromethane and hexane as the eluent. The pure fractions were collected, and the solvent was removed. The compound was purified by a second column treated with triethylamine using dichloromethane solvent resulting in 0.55 g of product. The material was sublimed under vacuum at 210° C. resulting in 0.35 (50% yield) of the product.
Synthesis of Compound 7
Step 1

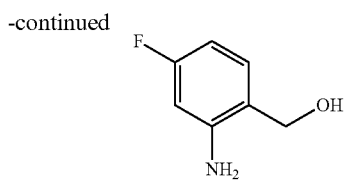

2-Amino-4-fluorobenzoic acid (10.0 g, 64.46 mmol) was dissolved in 50 mL of THF and cooled to 0° C. 1.0 M of lithium aluminum hydride in THF (79.93 mL, 79.93 mmol) was added dropwise. The mixture was allowed to warm to room temperature and stirred for about 6 hrs. The reaction was placed in an ice bath, and 3.0 mL of water was added dropwise. 50 mL of 1N NaOH was added dropwise and stirred for 15 min. 50 mL of water was added and stirred for 15 min. The mixture was extracted with ethyl acetate, washed with water, and concentrated to a volume of about 100 mL. This was then poured into a large excess of stirring hexanes. The precipitate that formed was filtered, washed with hexanes, and dried under vacuum to yield 6.71 g of off-white solids.
Step 2

The product from Step 1 (6.71 g, 47.5 mmol) was combined with 3-methylacetophenone (11.28 g, 84.13 mmol), RuCl$_2$(PPh$_3$)$_3$ (0.05 g, 0.048 mmol) and potassium hydroxide (0.83 g, 0.015 mmol) in 70 mL of toluene and refluxed overnight using a Dean-Stark trap to remove water.

of a 3:1 methoxyethanol:water solution. The mixture was purged with nitrogen for 20 min and refluxed overnight. The dark red precipitate that formed was filtered off, washed with methanol and hexanes, and used for the next step.

Step 4

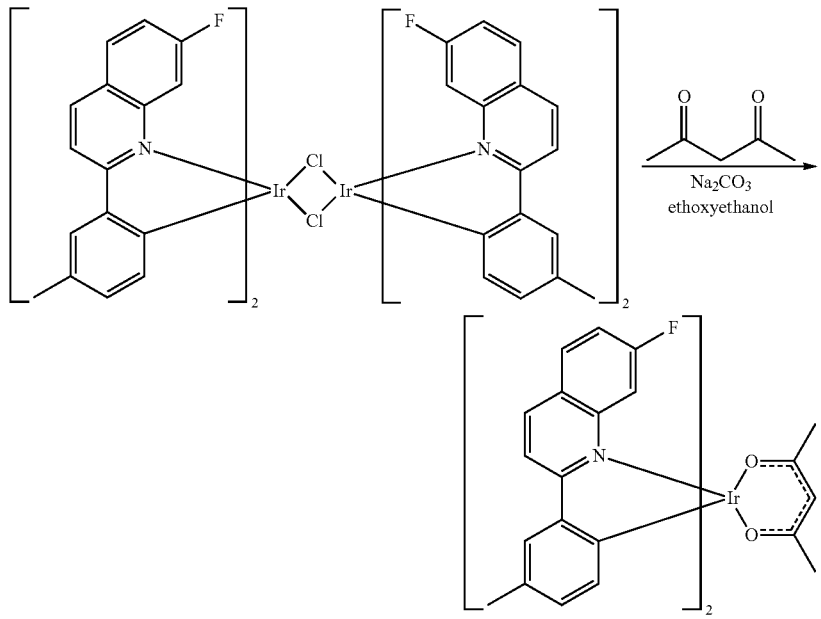

The reaction was cooled to room temperature, and a small amount of Celite was added to the mixture, which was then filtered through a silica gel plug and concentrated. Purification was achieved by chromatography (5% ethyl acetate/hexanes) followed by vacuum distillation at 200° C. to yield 6.59 g of yellow solids.

Step 3

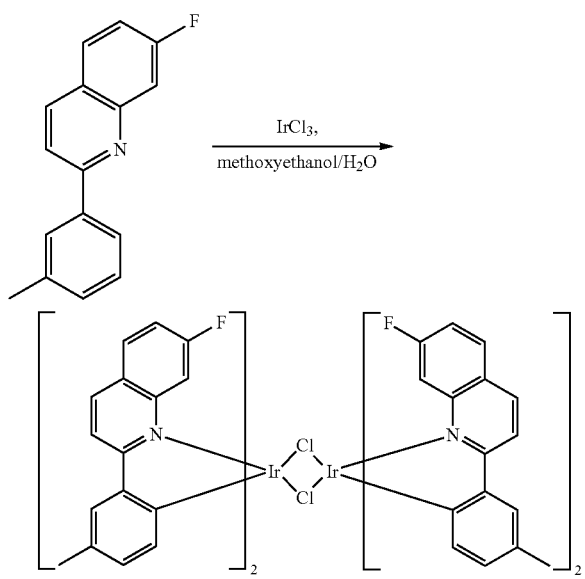

The ligand from Step 2 (6.59 g, 26.22 mmol) was combined with iridium chloride (4.41 g, 11.92 mmol) in 80 mL The dimer (17.39 g, 11.92 mmol) was suspended in 50 mL of ethoxyethanol. 2,4-pentanedione (12.28 mL, 119.20 mmol) and sodium carbonate (3.79 g, 35.76 mmol) were added, and the reaction was stirred overnight at room temperature. The reaction was poured into a large excess of stirring methanol. The red precipitate formed was filtered off, dissolved in dichloromethane, poured into stirring methanol, and filtered to give a red solid. This procedure was repeated. This solid was dried under vacuum to yield 4.40 g of red solid which was further purified by two sublimations, yielding 3.21 g of red solids (99.8% pure).

Synthesis of Compound 8

Step 1

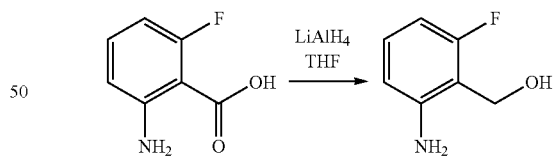

2-Amino-6-fluorobenzoic acid (10.0 g, 64.46 mmol) was dissolved in 50 mL of THF and cooled to 0° C. 1.0 M lithium aluminum hydride in THF (79.93 mL, 79.93 mmol) was added dropwise. The mixture was allowed to warm to room temperature and stirred for about 60 hrs. The reaction was placed in an ice bath, and 3 mL of water was added dropwise. 50 mL of 1N NaOH was added dropwise and stirred for 15 min. 50 mL of water was added and stirred for 15 min. The mixture was extracted with ethyl acetate, washed with water, and concentrated to a volume of about 100 mL This was then poured into a large excess of stirring hexanes. The precipitate formed was filtered, washed with hexanes and dried under vacuum to yield 6.71 g of off-white solids.

Step 2

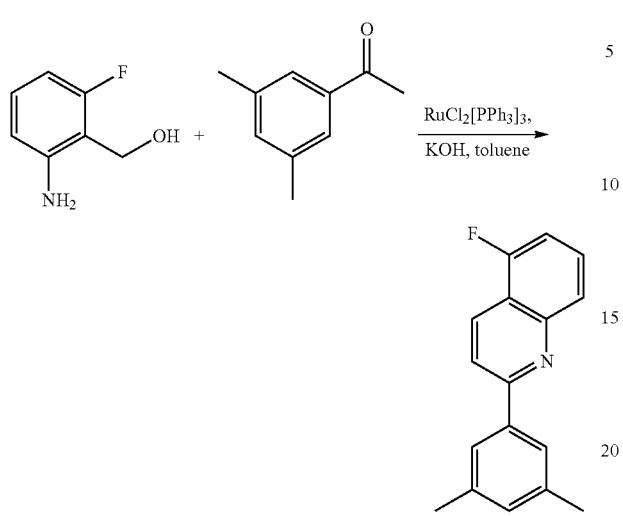

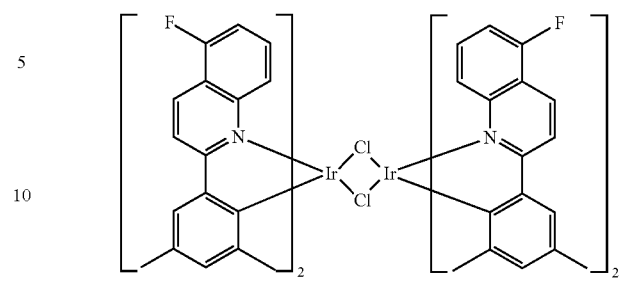

The ligand from Step 3 (6.59 g, 26.22 mmol) was combined with iridium chloride (4.41 g, 11.92 mmol) in 80 mL of a 3:1 methoxyethanol:water solution. The mixture was purged with nitrogen for 20 min and refluxed overnight. The black precipitate formed was filtered off, washed with methanol and hexanes, and used for the next step.

Step 4

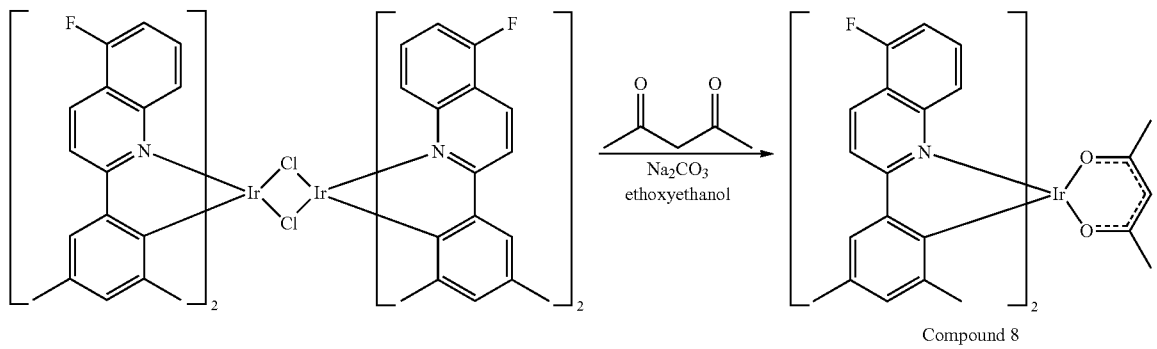

Compound 8

The product from Step 1 (6.71 g, 47.56 mmol) was combined with 3,5-dimethylacetophenone (11.28 g, 76.09 mmol), $RuCl_2(PPh_3)_3$ (0.05 g, 0.048 mmol) and potassium hydroxide (0.83 g, 0.015 mmol) in 70 mL of toluene and refluxed overnight using a Dean-Stark trap to remove water. The reaction was cooled to room temperature, and a small amount of Celite was added to the mixture, which was then filtered through a silica gel plug and concentrated. Purification was achieved by chromatography (5% ethyl acetate/hexanes) and two Kugelrohr distillations at 200° C. to yield 6.59 g of yellow solids.

Step 3

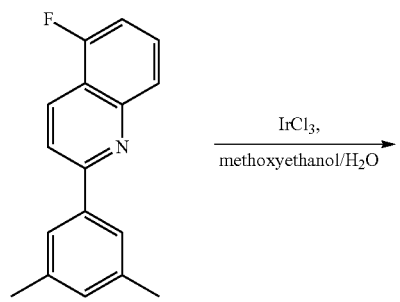

The dimer (17.39 g, 11.92 mmol) was suspended in 50 mL of ethoxyethanol. 2,4-pentanedione (12.28 mL, 119.20 mmol) and sodium carbonate (3.79 g, 35.76 mmol) were added, and the reaction was stirred overnight at room temperature. The reaction was poured into a large excess of stirring methanol. The red precipitate that formed was filtered off, dissolved in dichloromethane, poured into stirring methanol and filtered to give a red solid. This procedure was repeated. This solid was dried under vacuum to yield 4.40 g red solid, which was further purified by two sublimations, yielding 3.21 g red solids (99.0% pure).

Synthesis of Compound 9

Step 1

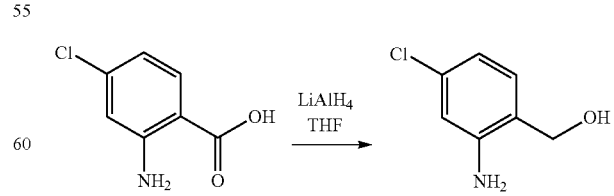

42.8 g of 2-amino-4-chlorobenzoic acid was dissolved in 200 mL of THF and cooled with an ice-water bath. To the solution was added 11.76 g of lithium aluminum hydride chips. The resulting mixture was stirred at room temperature for 8 hrs. 12 g of water was added followed by 12 g of 15% NaOH. 36 g of water was then added. The slurry was stirred at room temperature for 30 min. The slurry was filtered. The solid was washed with ethyl acetate. The liquid was combined, and the solvent was evaporated. The crude material was used for next step 113 without purification.

Step 2

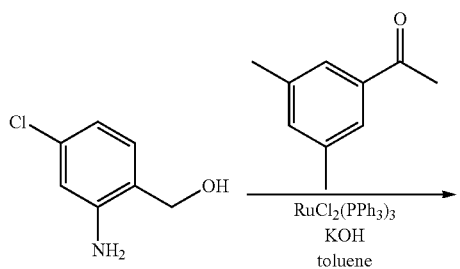

Step 3

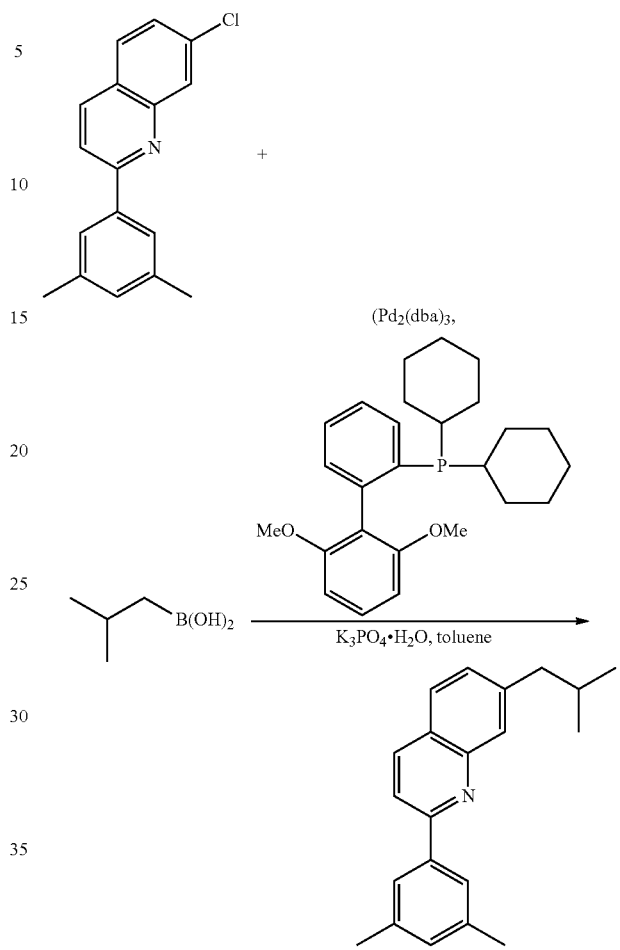

6.6 g of (2-amino-4-chlorophenyl)methanol, 10 g of 1-(3,5-dimethylphenyl)ethanone, 0.1 g of RuCl$_2$(PPh$_3$)$_3$, and 2.4 g potassium hydroxide in 100 mL of toluene were refluxed for 10 hrs. Water was collected from the reaction using a Dean-Stark trap. After cooled to room temperature, the mixture was filtered through a silica gel plug. The product was further purified with column chromatography using 2% ethyl acetate in hexanes as solvent to yield 9 g product. The product was further recrystallized from isopropanol. 5 g of product was obtained.

3.75 g of 7-chloro-2-(3,5-dimethylphenyl)quinoline, 2.8 g of isobutylboronic acid, 0.26 g of Pd$_2$(dba)$_3$, 0.47 g of 2-dicyclohexylphosphino-2',6'-dimethoxybiphenyl, and 16 g of potassium phosphate monohydrate were mixed in 100 mL of toluene. The system was degassed for 20 min and heated to reflux overnight. After cooled to room temperature, the crude product was purified by column chromatography using 2% ethyl acetate in hexanes as solvent. 3.6 g of product was obtained.

Step 4

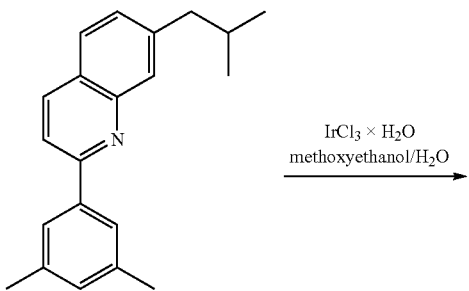

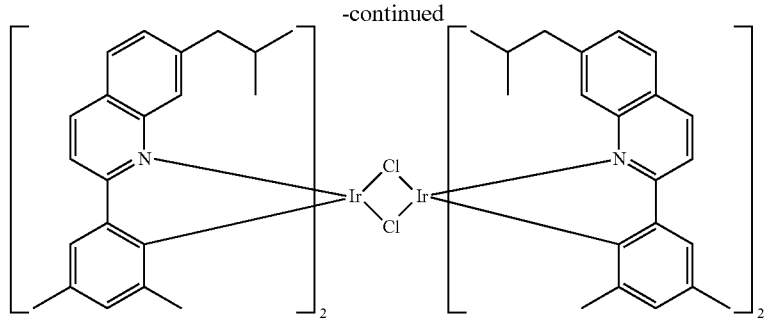

3.2 g of 2-(3,5-dimethylphenyl)-7-isobutylquinoline and 1.8 g of iridium chloride were mixed in 45 mL of methoxyethanol and 15 mL of water. After degassed for 10 min, the mixture was heated to reflux overnight. After cooled to room temperature, the precipitate was filtered and washed with methanol and hexanes. The dimer was then dried under vacuum and used for next step without further purification. 2.2 g of the dimer was obtained after vacuum drying.

Step 5

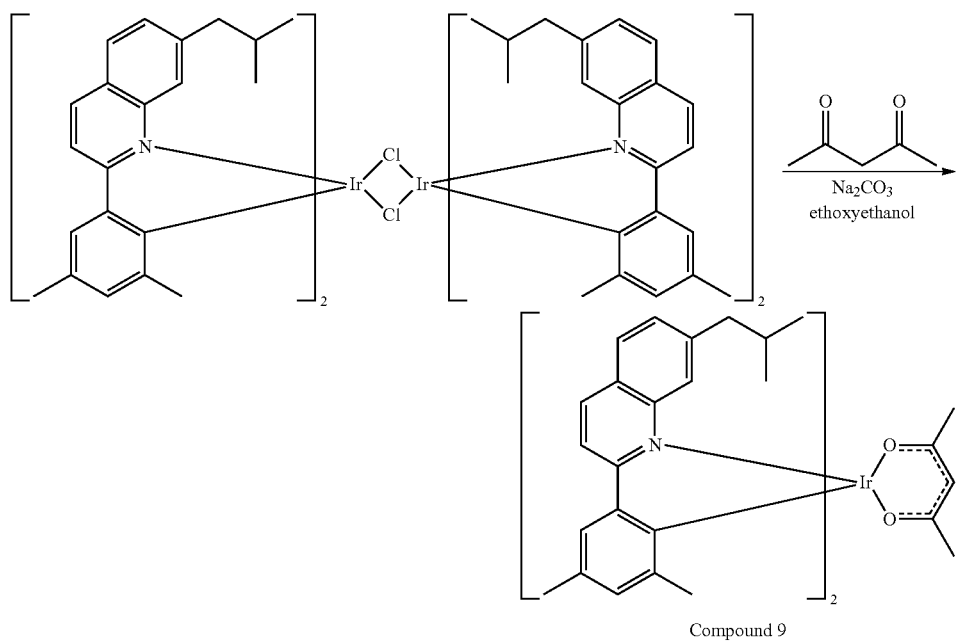

Compound 9

2.2 g of the dimer, 1.4 g of 2,4-pentanedione, and 0.83 g of sodium carbonate were mixed in 35 mL of 2-ethoxyethanol and stirred at room temperature for 24 hrs. The precipitate was filtered and washed with methanol. The solid was redissolved in dichloromethane. After evaporating the solvent, the solid was sublimed under high vacuum at 210° C. twice to obtain 1 g of final product.

Synthesis of Compound 10
Step 1

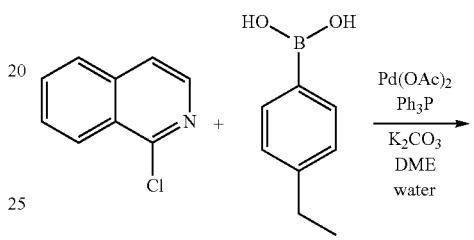

-continued

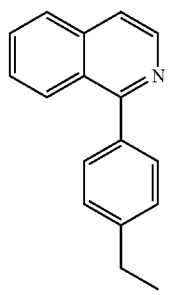

A mixture 1-chloroisoquinoline (5.0 g, 30.56 mmol), 4-ethylphenylboronic acid (5.04 g, 33.62 mmol), Ph₃P (1.60 g, 6.11 mmol), K₂CO₃ (10.98 g, 79.46 mmol), 25 mL of dimethoxyethane, and 25 mL of water was purged with nitrogen for 30 min. Pd(OAc)₂ was then added (0.34 g, 1.53 mmol), and the mixture was heated to reflux overnight under nitrogen. The cooled solution was diluted with water and ethyl acetate. The layers were separated, and the aqueous layer extracted with ethyl acetate. The organic layers were dried over magnesium sulfate, filtered, and evaporated to a residue. The residue was purified by column chromatography eluting with 0 to 20% ethyl acetate/hexanes. The chromatographed product was purified by Kugelrohr distillation to yield 5.74 g (81% yield) of product.

Step 2

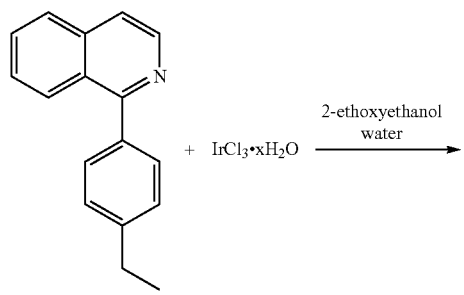

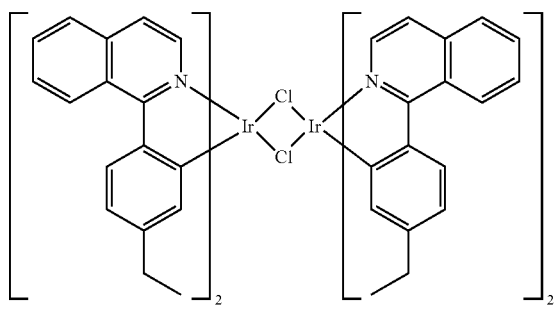

A mixture of 1-(4-ethylphenyl)isoquinoline (5.74 g, 24.60 mmol), iridium chloride (4.14 g, 11.18 mmol), 45 mL of 2-ethoxyethanol, and 15 mL of water was refluxed for 2 days under nitrogen. The cooled mixture was filtered, washed with water and methanol, and allowed to air dry.

Step 3

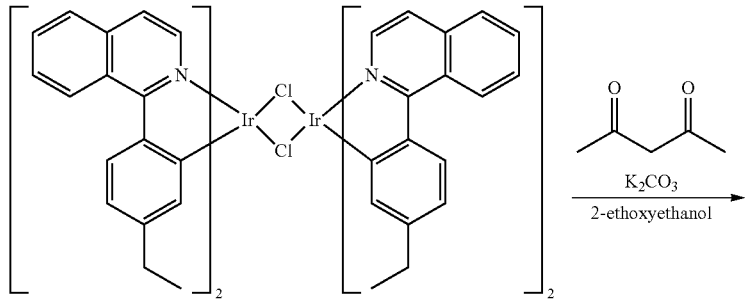

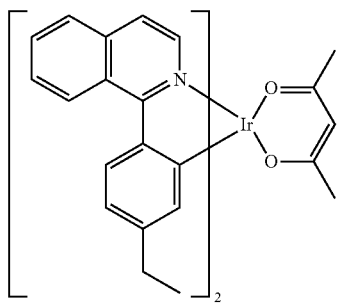

Compound 10

The dimer was mixed with 2,4-pentanedione (12.1 mL, 111.8 mmol), K₂CO₃ (4.64 g, 33.54 mmol), and 2-ethoxyethanol (75 mL) and heated to reflux under nitrogen. The cooled mixture was filtered, and the red solid was rinsed with methanol. The solid was purified by column chromatography. The column was pretreated with 20% triethylamine/hexanes, and then the compound was loaded and eluted with 20 and 50% dichloromethane/hexanes. The material was further purified by recrystallization from acetonitrile followed by two sublimations at 250° C. to afford 1.87 g (22% yield) of pure material.

Synthesis Compound 11

Step 1

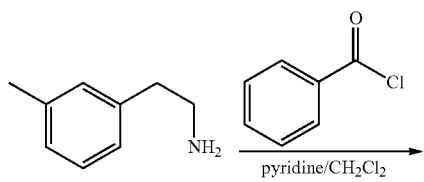

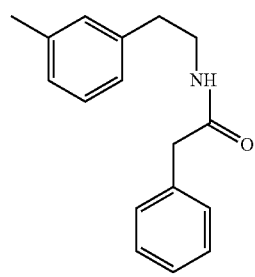

6.8 g of pyridine was added to 9.67 g (71.5 mmol) of 2-m-tolylethanamine in 100 mL of dichloromethane. The solution was cooled to 0° C. using an ice water bath. To the solution was added 10 mL of benzoyl chloride. After complete addition, the mixture was stirred at room temperature for 2 hrs and quenched by water. The organic layer was separated, washed with dilute HCl and sodium bicarbonate solution and water, dried over magnesium sulfate, and concentrated to a residue. The product was used for the next step without further purification.

Step 2

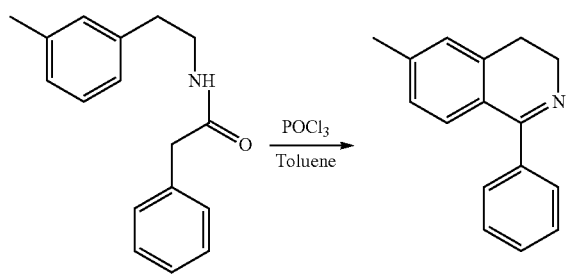

17.5 g of N-(3-methylphenethyl)-2-phenylacetamide and 60 mL of POCl₃ were mixed with 150 mL of xylenes. The mixture was heated to reflux for 4 hrs. After cooled to room temperature, the solvent was decanted. The solid was dissolved with ice water. The mixture was neutralized with NaOH. The mixture was extracted with dichloromethane. The organic layer was then washed with water and dried over magnesium sulfate. After solvent evaporation, 12 g of product was obtained. The product was used for the next step without further purification.

Step 3

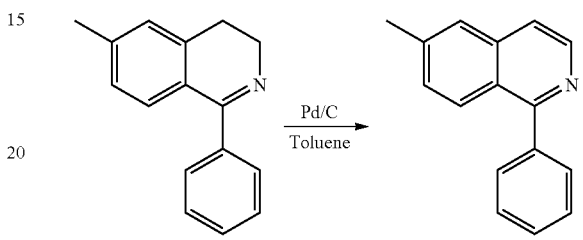

12 g of 6-methyl-1-phenyl-3,4-dihydroisoquinoline was mixed with 10 g of Pd/C (5%) in 100 mL of xylenes and heated to reflux overnight. After cooled to room temperature, the solid was removed by filtration. The solvent was then evaporated. The residue was purified by silica gel column chromatography using hexanes and ethyl acetate as solvent. 7.1 g of product was obtained after final distillation.

Step 4

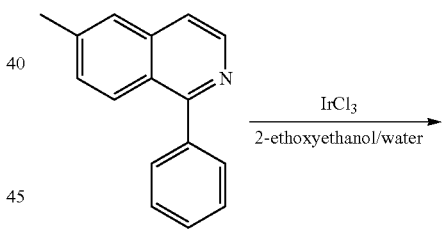

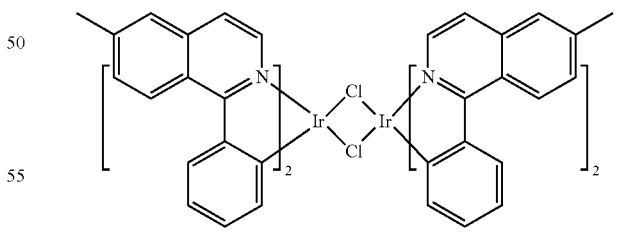

6.1 g (27.8 mmol) of 6-methyl-1-phenylisoquinoline and 4.3 g (12 mmol) of iridium chloride were mixed in 90 mL of 2-ethoxyethanol and 30 mL of water. The mixture was heated to reflux overnight. After cooled to room temperature, the solid was collected by filtration. 6.2 g of the dimer was obtained. The dimer was used for the next step without further purification.

Step 5

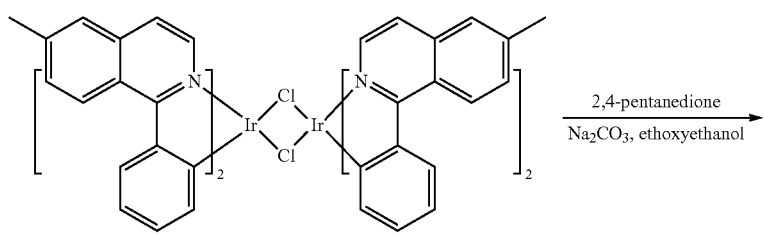

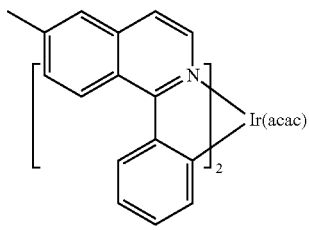

Compound 11

6.0 g of the dimer, 1.8 g of 2,4-pentanedione, and 2.9 g of sodium carbonate were added to 100 mL of 2-ethoxyethanol and heated to reflux overnight. After cooled to room temperature, the solid was collected by filtration. The solid was then washed with dichloromethane. The filtrate was concentrated and run through a triethylamine treated silica gel column. The final compound was sublimed under high vacuum. 2.0 g of 99.6% pure product was obtained after sublimation.

Synthesis of Compound 12

Step 1

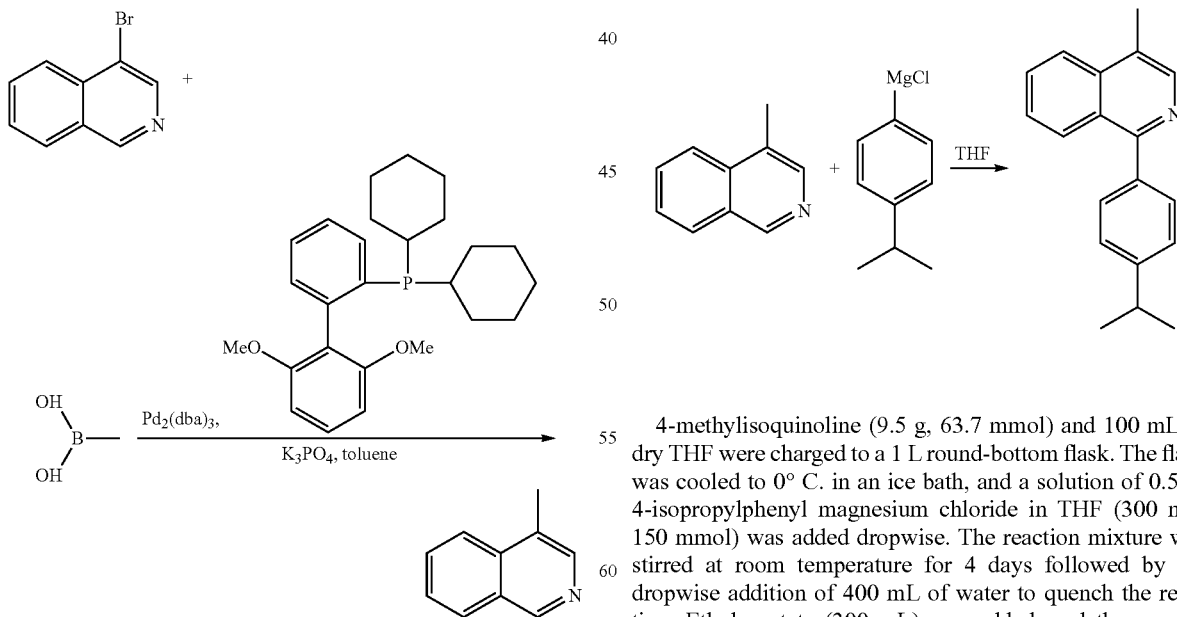

4-bromoisoquinoline (15 g, 72.5 mmol), methylboronic acid (8.8 g, 145 mmol), $K_3PO_4$ (62 g, 290 mmol), $Pd_2(dba)_3$ (6.6 g, 7.2 mmol), 2-dicyclohexylphosphino-2',6'-dimethoxybiphenyl (5.9 g, 14.4 mmol, 0.2 equiv), and 350 mL of anhydrous toluene were charged to a dry 500 mL three-neck flask. The mixture was refluxed under nitrogen for 20 hrs. After cooling, 200 mL of methylene chloride was added. The mixture was filtered to remove insolubles, then concentrated under vacuum. The resulting crude material was distilled at 130° C. (first fraction at 95° C. was discarded). Approximately 9.8 g of a colorless liquid was obtained (94% yield). The product was used for the next step without further purification (96% product, 3.5% isoquinoline).

Step 2

4-methylisoquinoline (9.5 g, 63.7 mmol) and 100 mL of dry THF were charged to a 1 L round-bottom flask. The flask was cooled to 0° C. in an ice bath, and a solution of 0.5 M 4-isopropylphenyl magnesium chloride in THF (300 mL, 150 mmol) was added dropwise. The reaction mixture was stirred at room temperature for 4 days followed by the dropwise addition of 400 mL of water to quench the reaction. Ethyl acetate (300 mL) was added, and the organic layers were separated and bubbled with air for 2 days with stirring. Then, the organic layer was concentrated under vacuum. The resulting oil was purified by column chromatography using 10% ethyl acetate/hexanes and vacuum distilled to give 2.7 g (16% yield) of a pale yellow oil.

Step 3

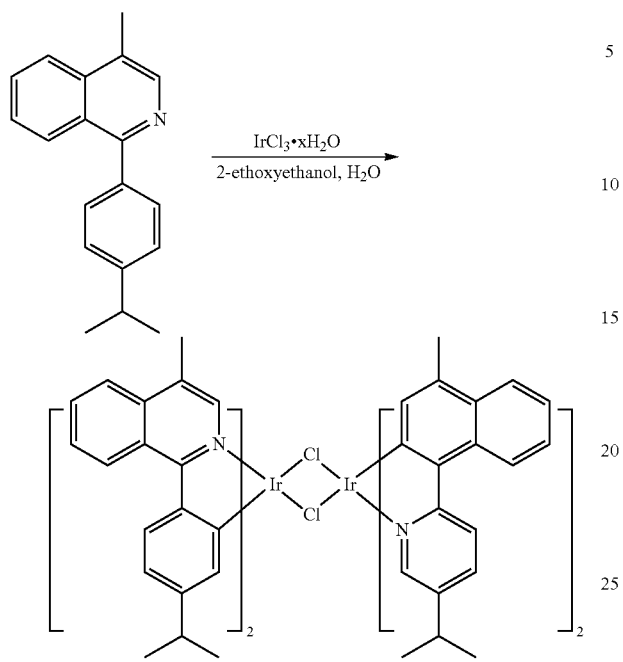

1-(4-isopropylphenyl)-4-methylisoquinoline (2.7 g, 10.3 mmol, 2.2 equiv), iridium chloride (1.67 g, 4.7 mmol), 40 mL of 2-ethoxyethanol, and 8 mL of water were charged to a 125 mL three-neck flask. The mixture was heated at reflux for 24 hrs. The cooled mixture was filtered and washed with 2-ethoxyethanol, methanol, and hexanes to afford 2.9 g of a reddish-brown powder (83% yield).

Step 4

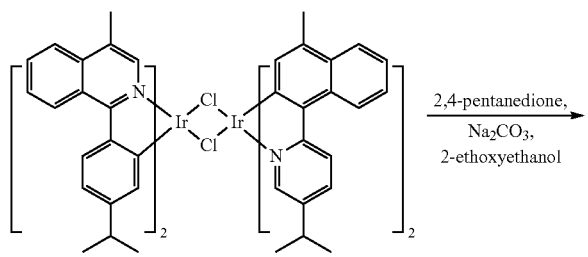

Compound 12

The dimer (2.9 g, 1.94 mmol), 2,4-pentanedione (1.94 g, 19.4 mmol), sodium carbonate (2.05 g, 19.3 mmol), and 30 mL of 2-ethoxyethanol were charged to a 125 mL three-neck flask. The mixture was stirred at reflux for 5 hrs. The cooled solution was filtered and washed with 2-ethoxyethanol, methanol, and hexanes to afford 1.85 g of a red solid (97% pure), which was further purified by sublimation.

Synthesis of Compound 13

Step 1

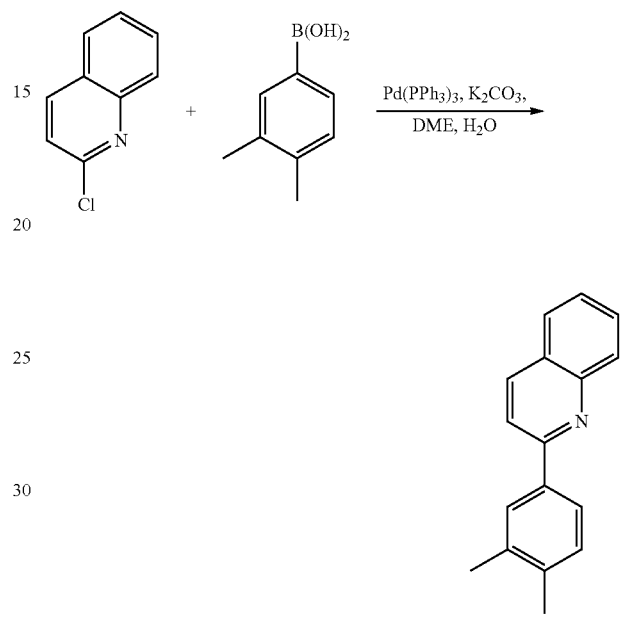

To a 500 mL round bottle flask, 12.05 g (72.9 mmol) of 2-chloroquinoline, 13.2 g (83.86 mmol) of 3,4-dimethylphenylboronic acid, 2.5 g (2.18 mmol) of Pd(PPh$_3$)$_4$, 30.0 g (214 mmol) of K$_2$CO$_3$, 150 mL of DME, and 150 mL of water were charged. The reaction mixture was heated to reflux under nitrogen overnight. The reaction mixture was cooled. The organic extracts were purified by silica gel column chromatography (10% ethyl acetate in hexane as eluent). The material obtained was further purified by vacuum distillation (Kugelrohr) at 200° C. to yield 15.5 g (95% yield) of product as a colorless liquid.

Step 2

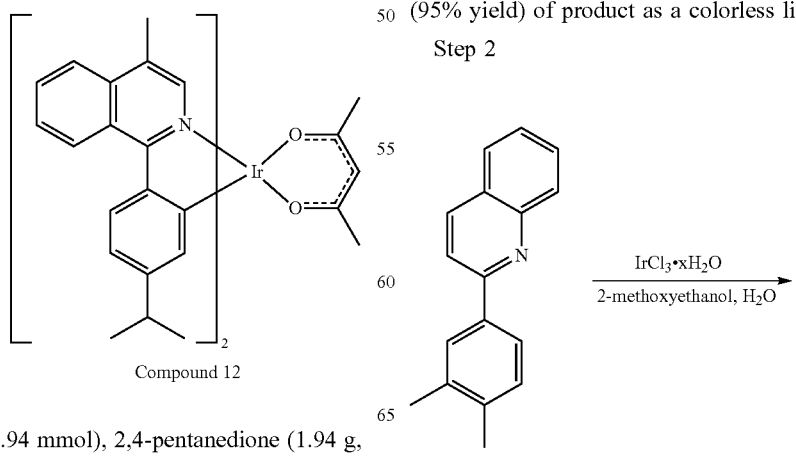

53

-continued

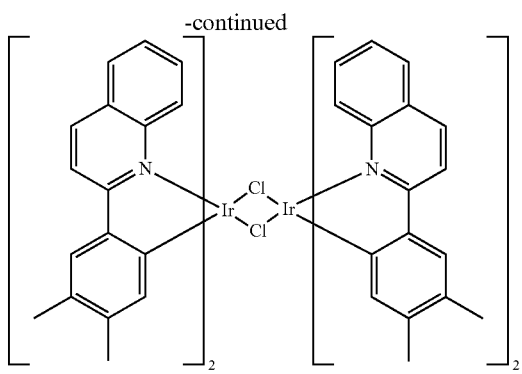

8.1 g (34.7 mmol) of ligand from Step 1, 120 mL of 2-methoxyethanol, and 40 mL of water were charged in a 500 mL three-neck flask. The reaction mixture was bubbled with nitrogen for 45 min with stirring. Then, 5.3 g (14.5 mmol) of IrCl$_3$.xH$_2$O was added into this mixture and heated to reflux under nitrogen for 17 hrs. The reaction mixture was cooled and filtered. The solid was washed with methanol (3×100 mL) followed by hexane (3×100 mL). 7.8 g of the dimer (65%) was obtained after drying in a vacuum oven. The dimer was used for next step without further purification.

Step 3

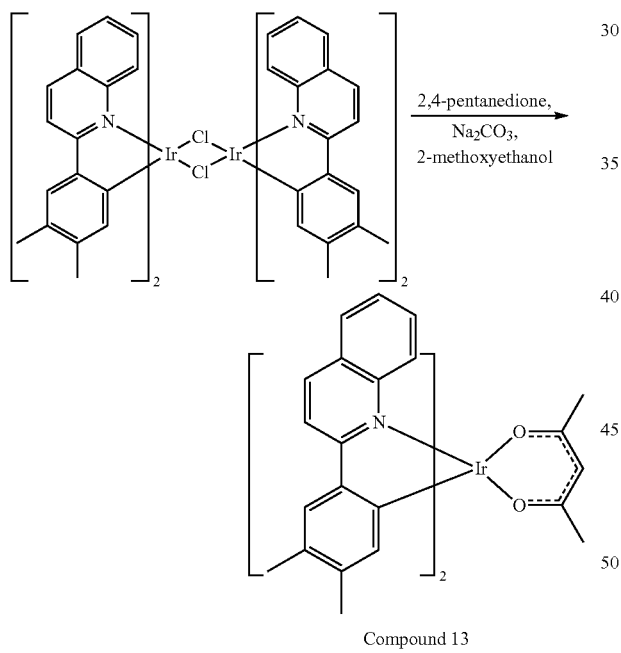

Compound 13

6.0 g of the dimer (4.3 mmol), 4.4 g of 2,4-pentanedione (43 mmol), 4.7 g (43.0 mmol) of sodium carbonate, and 200 mL of 2-methoxyethanol were added in a 500 mL round bottle flask. The reaction mixture was vigorously stirred at room temperature for 28 hrs. The reaction mixture was then suction filtered and washed with methanol (3×100 mL) followed by hexane (2×100 mL) The solid was collected and stirred in ~500 mL of a solvent mixture (450 mL of methylene chloride and 50 mL of triethylamine) for ~10 min. Then the mixture was separated by silica gel column (column pretreated with triethylamine/hexane) with 50% methylene chloride in hexane as elute. ~6 g red solid was obtained as the product.

54

Synthesis of Compound 14

Step 1

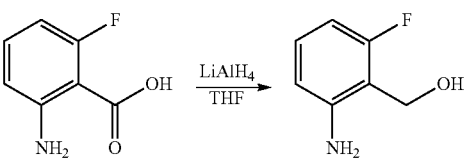

Lithium aluminum hydride (2.65 g, 69.8 mmol) was added to 80 mL of THF that was cooled in an ice bath. A solution of 2-amino-6-fluorobenzoic acid (10 g, 64.46 mmol) in 50 mL THF was added dropwise via a dropping funnel. The reaction was allowed to stir overnight at room temperature. Another portion of 20 mL of 1M lithium aluminum hydride in THF was added, and the reaction was heated to 40° C. Upon cooling in an ice bath, 3 mL of water was added carefully via a dropping funnel followed by 50 mL of 1N NaOH, and the mixture was stirred for 15 min. Next, 50 mL of water was added, and the mixture was stirred for 10 min. More NaOH solution was added, and the emulsion was stirred overnight. The organic layers were extracted, washed with water, and concentrated, and the residue was dissolved in 100 mL of ethyl acetate. Hexanes were added, and a solid precipitated out and was filtered to yield 3.66 g of a tan solid, which was used for the next step.

Step 2

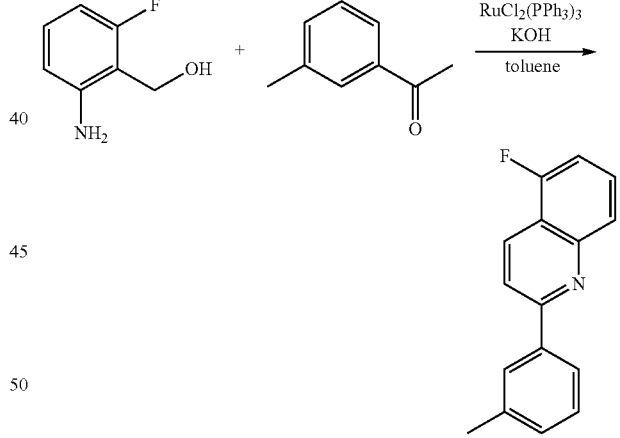

A mixture of (2-amino-6-fluorophenyl)methanol (3.66 g, 25.94 mmol), 3'-methylacetophenone (5.6 mL, 41.50 mmol), RuCl$_2$(PPh$_3$)$_3$ (25 mg, 0.026 mmol), and powdered potassium hydroxide (247 mg, 4.41 mmol) in 60 mL of toluene was refluxed overnight under nitrogen in a 200 mL round-bottom flask equipped with a Dean-Stark trap under nitrogen. Upon cooling, Celite was added, and the mixture was filtered through a silica gel plug that was eluted with ethyl acetate. The solution was evaporated to a brown oil, which was purified by column chromatography eluting with 0 and 2% ethyl acetate/hexanes. The cleanest fractions were further purified by Kugelrohr distillation at 220° C. to yield 4.6 g of product.

Step 3

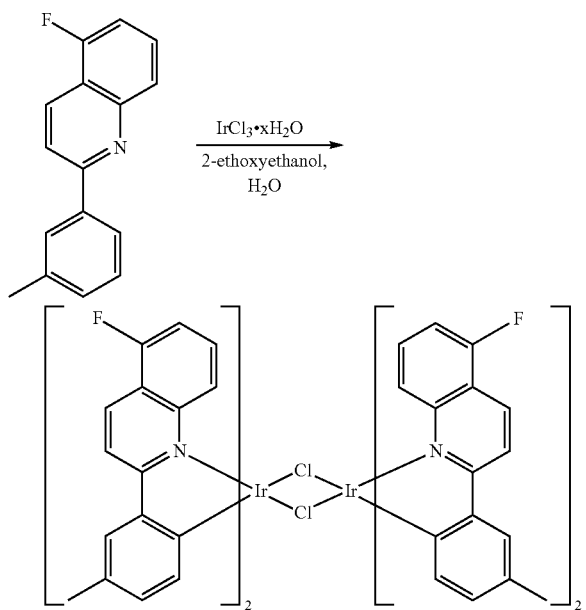

A mixture of 5-fluoro-2-m-tolylquinoline (3.0 g, 12.64 mmol), iridium chloride (2.13 g, 5.75 mmol), 25 mL of 2-ethoxyethanol, and 8 mL of water was purged with nitrogen for 20 min and then heated to reflux overnight under nitrogen. The cooled mixture was filtered, washed with water and methanol, and allowed to air dry.

Step 4

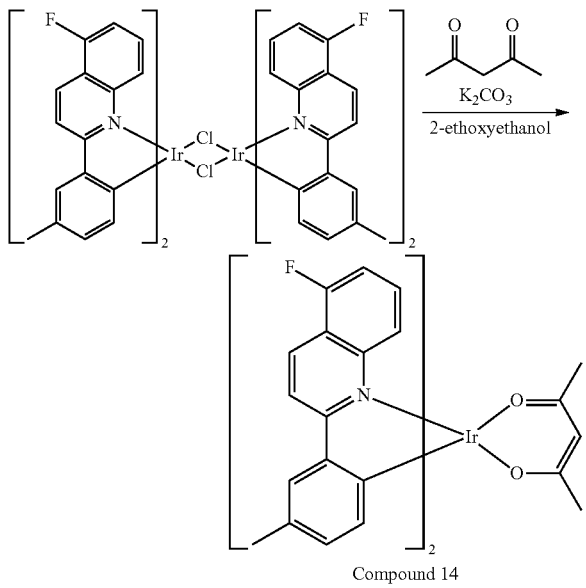

Compound 14

The dimer was mixed with 2,4-pentanedione (3.0 mL, 28.8 mmol), K$_2$CO$_3$ (1.23 g, 8.90 mmol), and 2-ethoxyethanol (50 mL) and heated to near reflux under nitrogen overnight. The cooled mixture was filtered, and the red solid rinsed with isopropanol. The solid was dissolved in dichloromethane and purified on a silica gel plug. The plug was treated with 10% triethylamine/hexanes followed by hexanes prior to loading the material, and the product was eluted with dichloromethane. The fractions with product were collected and concentrated to a small volume. Isopropanol was added, and the mixture was concentrated. The precipitated solid was filtered and purified by two sublimations to yield 0.82 g of product.

Synthesis of Compound 15

Step 1

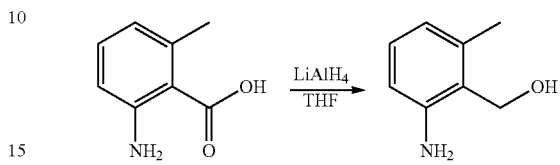

A solution of 2-amino-6-methylbenzoic acid (10 g, 66.15 mmol) in 60 mL of THF was cooled in an ice-salt bath. A solution of lithium aluminum hydride in THF was added using a dropping funnel under nitrogen (2.4 M, 33 mL, 79.38 mmol). The reaction was allowed to proceed overnight. The reaction was quenched with water, then 50 mL of 1N NaOH solution was added dropwise as the reaction was cooled in an ice-salt bath. Next, 50 mL of water was added and stirred for 1 hr, followed by 50% NaOH solution. The mixture was extracted with dichloromethane. The organic extracts were dried over magnesium sulfate, filtered, and evaporated to a residue. The residue was purified by column chromatography eluting with 10 to 60% ethyl acetate/hexanes to yield 7.7 g (85% yield) of a tan solid.

Step 2

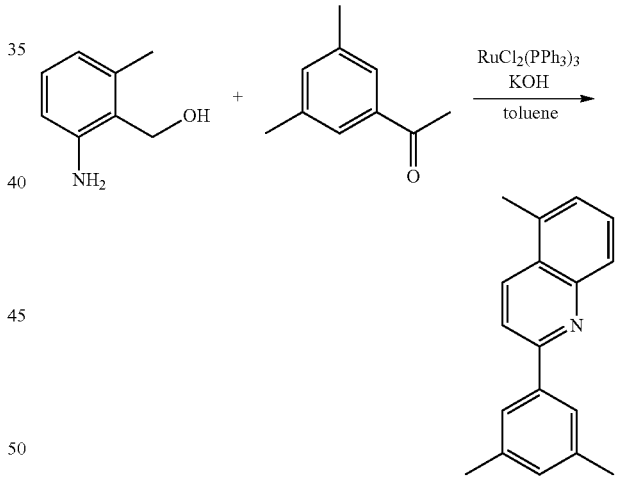

A mixture of (2-amino-6-methylphenyl)methanol (7.7 g, 56.13 mmol), 3',5'-dimethylacetophenone (12.5 g, 84.20 mmol), dichlorotris(triphenylphosphine)ruthenium (III) (54 mg, 0.056 mmol), and powdered potassium hydroxide (535 mg, 9.54 mmol) in 150 mL of toluene was refluxed overnight under nitrogen in a 500 mL round-bottom flask equipped with a Dean-Stark trap under nitrogen. Upon cooling, Celite was added, and the mixture was filtered through a silica gel plug that was eluted with ethyl acetate. The solution was evaporated to a dark oil, which was purified by column chromatography eluting with 0 to 2% ethyl acetate/hexanes. A yellow oil was obtained, which solidified upon drying on high vacuum. The solid was recrystallized from hexanes to yield 7.8 g (56% yield) of a yellow solid.

Step 3

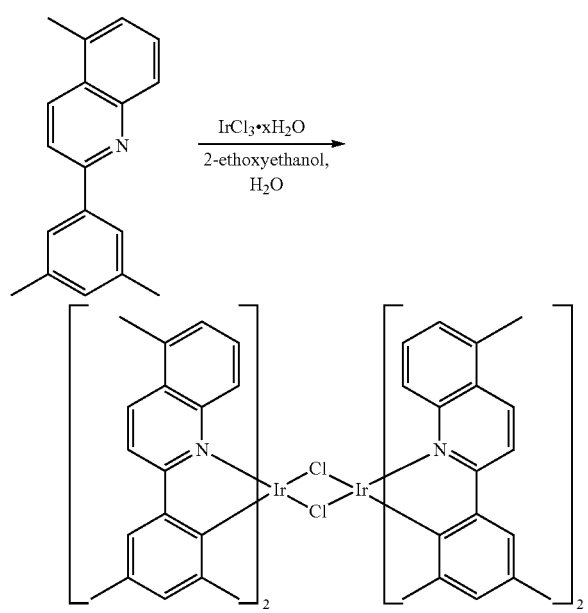

A mixture of 5-methyl-2-(3,5-dimethylphenyl)quinoline (7.8 g, 31.54 mmol), iridium chloride (3.89 g, 10.51 mmol), 45 mL of 2-ethoxyethanol, and 15 mL of water was purged with nitrogen for 20 min, then heated to reflux under nitrogen for 24 hrs. The cooled mixture was filtered, washed with water and methanol, and allowed to air dry.

Step 4

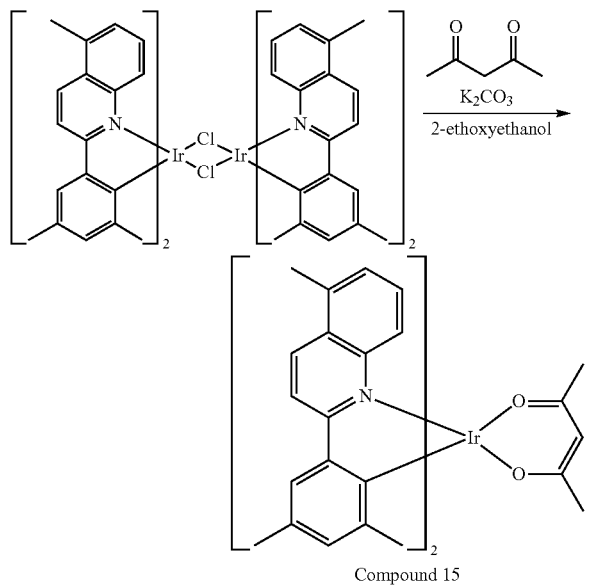

Compound 15

The dimer was mixed with 2,4-pentanedione (5.5 mL, 53 mmol), $K_2CO_3$ (1.23 g, 8.90 mmol), and 2-ethoxyethanol (100 mL) and heated to 110° C. under nitrogen for 1 day. The cooled mixture was filtered, and the red solid was rinsed with isopropanol. The solid was dissolved in dichloromethane and purified on a silica gel plug. The plug was treated with 10% triethylamine/hexanes followed by hexanes prior to loading the material, and the product was eluted with dichloromethane. The fractions with product were collected and concentrated to a small volume. Isopropanol was added, and the mixture was concentrated. The precipitated solid was filtered and purified by two sublimations to yield 3.73 g of product.

Synthesis of Compound 16

Step 1

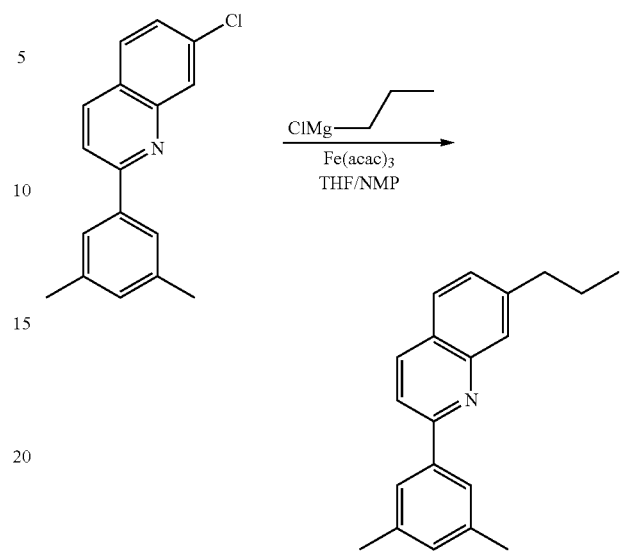

2-xylyl-7-chloroquinoline (3.0 g, 11 mmol) from Step 2 of Compound 9 and iron(III) acetylacetonate (0.2 g, 0.56 mmol) were dissolved in 66 mL of a solution of THF/1-methyl-2-pyrrolidinone (60/6) in a 250 mL round-bottom flask. Nitrogen was bubbled through the reaction mixture for 10 min. The solution was cooled using an ice bath. 11.2 mL of 2.0 M propylmagnesium chloride in ether was added dropwise. The reaction was stirred for 2 hrs, then quenched slowly with water. The reaction mixture was allowed to warm to room temperature, and ethyl acetate was added. The organic phase was washed with water and dried over magnesium sulfate. The solvent was removed under vacuo, and the product was chromatographed using a silica gel column with 2% ethyl acetate in hexanes as the eluent to give 2 g (67% yield) of product.

Step 2

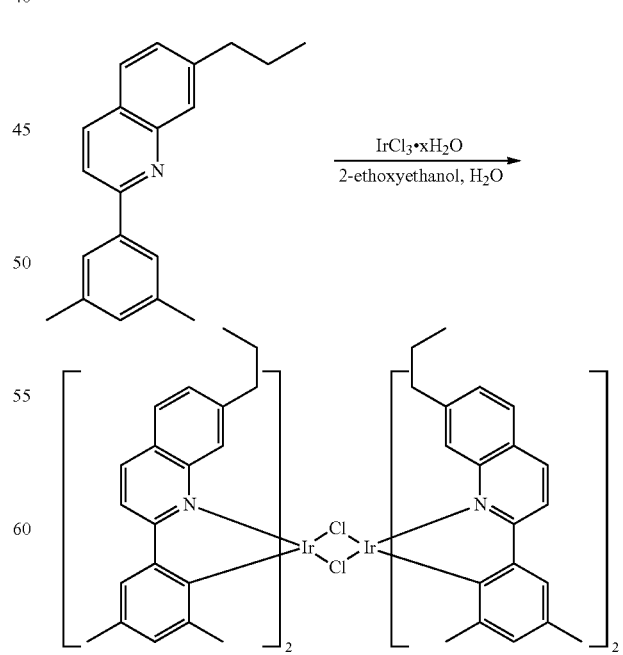

2-(3,5-dimethylphenyl)-7-propylquinoline (2.5 g, 9.1 mmol) and iridium(III) chloride (1.3 g, 3.6 mmol) were dissolved in 50 mL of a 3:1 mixture of 2-ethoxyethanol and water, respectively, in a 100 mL round-bottom flask. The solution was purged with nitrogen for 10 min, then refluxed under nitrogen for 16 hrs. The reaction mixture was allowed to cool to room temperature, and the precipitate was filtered and washed with methanol. The dimer was then dried under vacuum and used for next step without further purification. 2.0 g of the dimer was obtained after vacuum drying.

Step 3

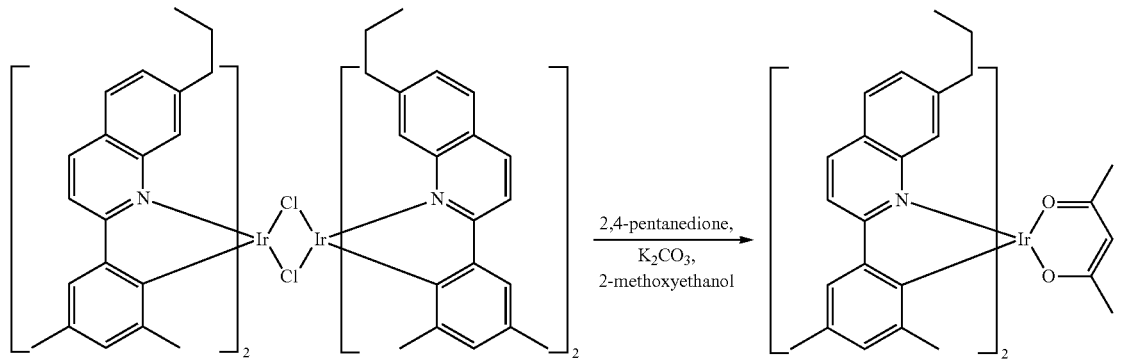

The dimer (2.0 g, 1.3 mmol), 2,4-pentanedione (1.3 g, 1.0 mmol), and $K_2CO_3$ (2.0 g, 14.0 mmol) were added to 50 mL of 2-methoxyethanol and stirred at room temperature for 24 hrs. The precipitate was filtered and washed with methanol. The solid was re-dissolved in dichloromethane and passed through a plug with Celite, silica gel, and basic alumina. The solvent was evaporated under vacuum to give 1.0 g (50% yield) of product.

Synthesis of Compound 17

Step 1

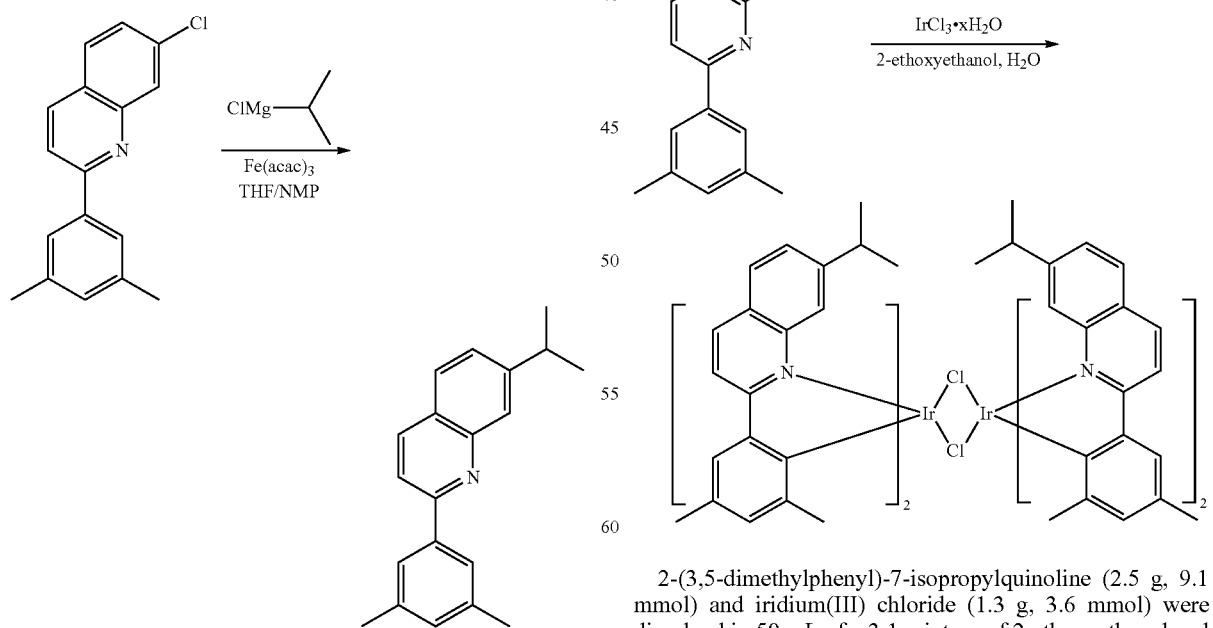

2-xylyl-7-chloroquinoline (3.0 g, 11 mmol) from Step 2 of Compound 9 and iron(III) acetylacetonate (0.2 g, 0.56 mmol) were dissolved in 66 mL of a solution of THF/1-methyl-2-pyrrolidinone (60/6) in a 250 mL round-bottom flask. Nitrogen was bubbled through the reaction mixture for 10 min. The solution was cooled using an ice bath. 11.2 mL of 2.0M isopropylmagnesium chloride in ether was added dropwise. The reaction was stirred for 2 hrs and then quenched slowly with water. The reaction mixture was allowed to warm to room temperature, and ethyl acetate was added. The organic phase was washed with water and dried over magnesium sulfate. The solvent was removed under vacuo, and the product was chromatographed using a silica gel column with 2% ethyl acetate in hexanes as the eluent to give 2 g (67% yield) of product.

Step 2

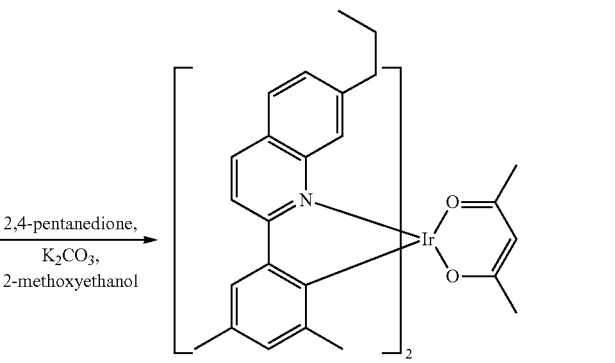

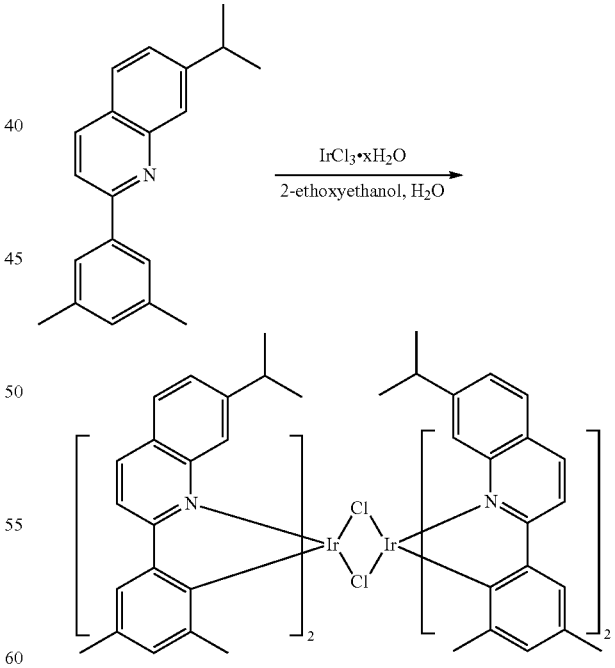

2-(3,5-dimethylphenyl)-7-isopropylquinoline (2.5 g, 9.1 mmol) and iridium(III) chloride (1.3 g, 3.6 mmol) were dissolved in 50 mL of a 3:1 mixture of 2-ethoxyethanol and water, respectively, in a 100 mL round-bottom flask. The solution was purged with nitrogen for 10 min and then refluxed under nitrogen for 16 hrs. The reaction mixture was then allowed to cool to room temperature, and the precipitate was filtered and washed with methanol. The dimer was then dried under vacuum and used for next step without further purification. 2.0 g of the dimer was obtained after vacuum drying.

Step 3 mmol) were mixed with 40 mL of DME and 40 mL water in a 100 mL flask. The reaction mixture was heated to reflux under nitrogen overnight. The reaction was cooled, and the organic extracts were purified with a silica gel column with 2% ethyl acetate in hexanes as the eluent to give 1.0 g (58% yield) of product.

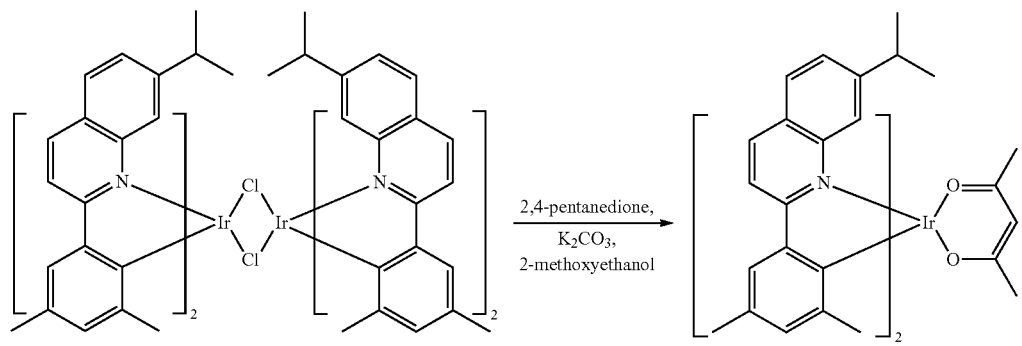

Compound 17

The dimer (2.0 g, 1.3 mmol), 2,4-pentanedione (1.3 g, 1.0 mmol), and K$_2$CO$_3$ (2.0 g, 14.0 mmol) were added to 50 mL of 2-methoxyethanol and stirred at room temperature for 24 hrs. The precipitate was filtered and washed with methanol. The solid was re-dissolved in dichloromethane and passed through a plug with Celite, silica gel, and basic alumina. The solvent was evaporated under vacuum to give 1.0 g (50% yield) of product.

Synthesis of Compound 18

Step 1

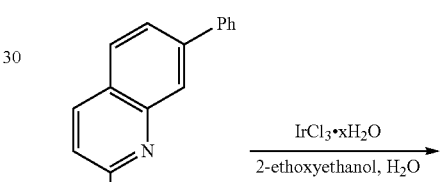

Step 2

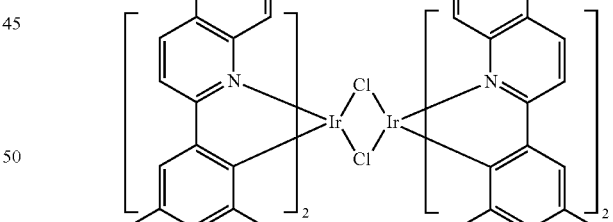

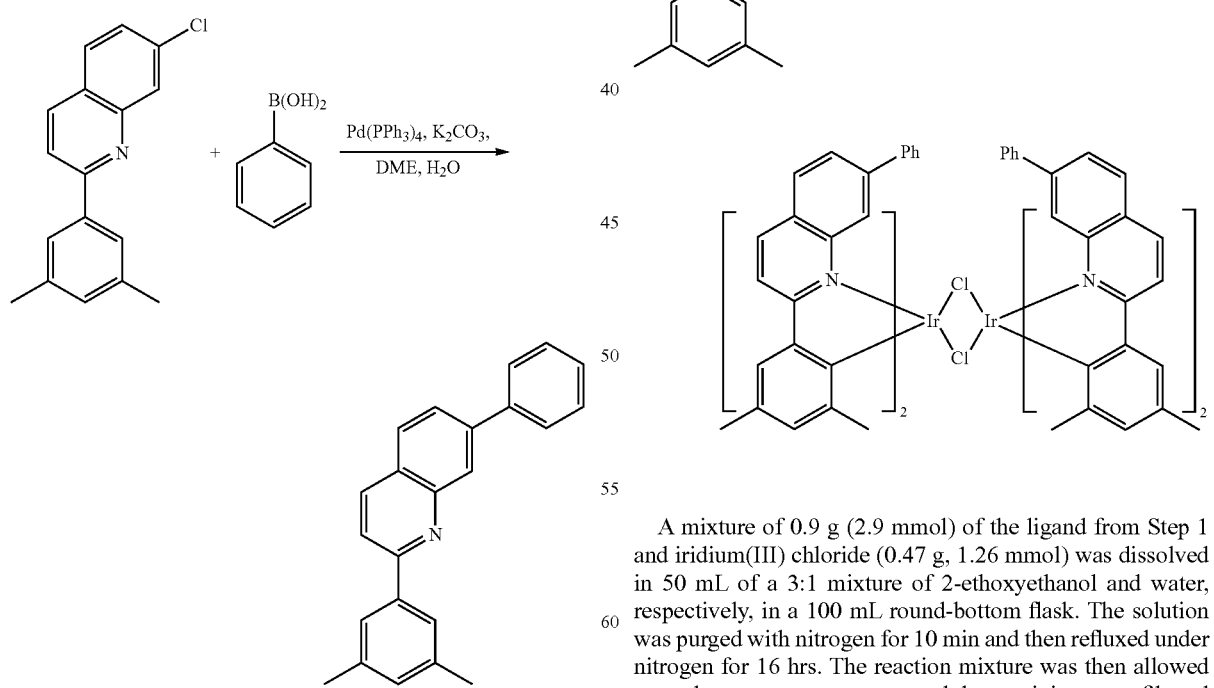

2-xylyl-7-chloroquinoline (1.5 g, 5.6 mmol) from Step 2 of Compound 9, phenylboronic acid (1.4 g, 11.0 mmol), Pd(PPh$_3$)$_4$ (0.2 g, 0.168 mmol), and K$_2$CO$_3$ (2.3 g, 16.6

A mixture of 0.9 g (2.9 mmol) of the ligand from Step 1 and iridium(III) chloride (0.47 g, 1.26 mmol) was dissolved in 50 mL of a 3:1 mixture of 2-ethoxyethanol and water, respectively, in a 100 mL round-bottom flask. The solution was purged with nitrogen for 10 min and then refluxed under nitrogen for 16 hrs. The reaction mixture was then allowed to cool to room temperature, and the precipitate was filtered and washed with methanol. The dimer was then dried under vacuum and used for next step without further purification. 0.61 g (50% yield) of the dimer was obtained after vacuum drying.

Step 3

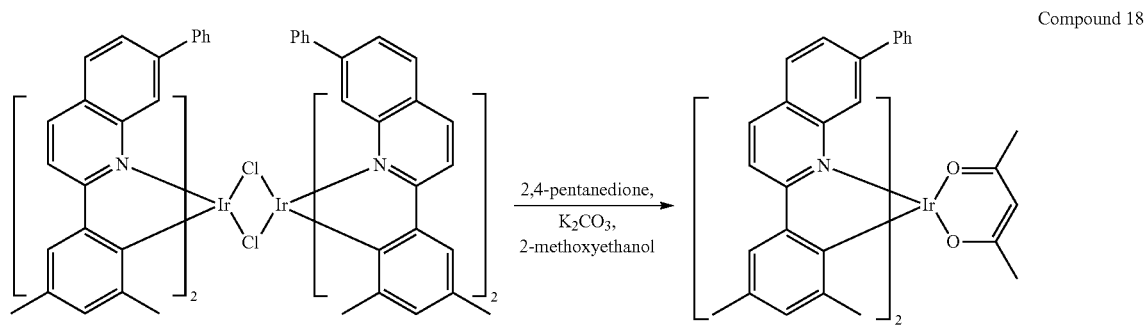
Compound 18

0.6 g the dimer, 2,4-pentanedione (0.37 g, 3.5 mmol), and K$_2$CO$_3$ (0.38 g, 3.5 mmol) were added to 50 mL of 2-methoxyethanol and stirred at room temperature for 24 hrs. The precipitate was filtered and washed with methanol. The solid was redissolved in dichloromethane and passed through a plug with Celite, silica gel, and basic alumina. The solvent was evaporated under vacuum to give ~0.45 g (69% yield) of product.

Synthesis of Compound 19

Step 1

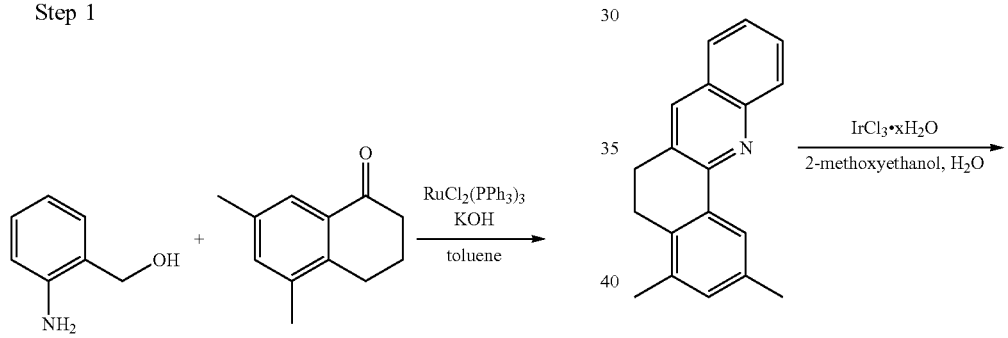

acetate. The solution was evaporated, and the residue was purified by column chromatography eluting with 5 and 10% ethyl acetate/hexanes. 10.7 g (76% yield) product was obtained.

Step 2

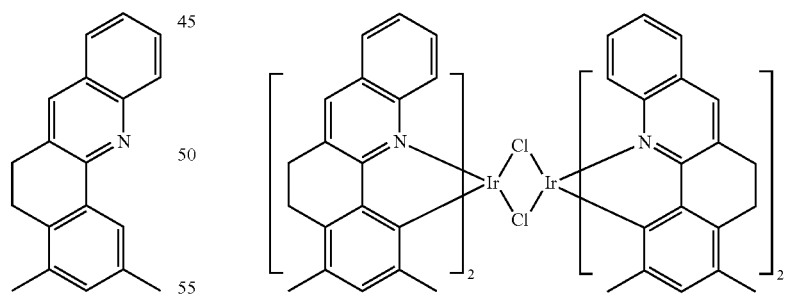

A mixture of 2-aminobenzyl alcohol (11.2 g, 89.2 mmol), 5,7-dimethyl-1-tetralone (10.0 g, 55.7 mmol), dichlorotris (triphenylphosphine)ruthenium (III) (0.11 g, 0.111 mmol), and powdered potassium hydroxide (0.63 g, 11.2 mmol) in 200 mL of toluene was refluxed overnight under nitrogen in a 500 mL round-bottom flask equipped with a Dean-Stark trap. Celite was added to the cooled reaction mixture and filtered through a silica gel plug that was eluted with ethyl 2.8 g (10.8 mmol) of the ligand from Step 1, 1.67 g (4.5 mmol) of IrCl$_3$·xH$_2$O, 60 mL 2-methoxyethanol, and 20 mL water were mixed in a 100 mL round flask. The reaction mixture was heated to reflux under nitrogen overnight. The reaction was cooled and filtered. The solid was washed by methanol and hexane. 2.0 g of the dimer (50%) was obtained.

Step 3

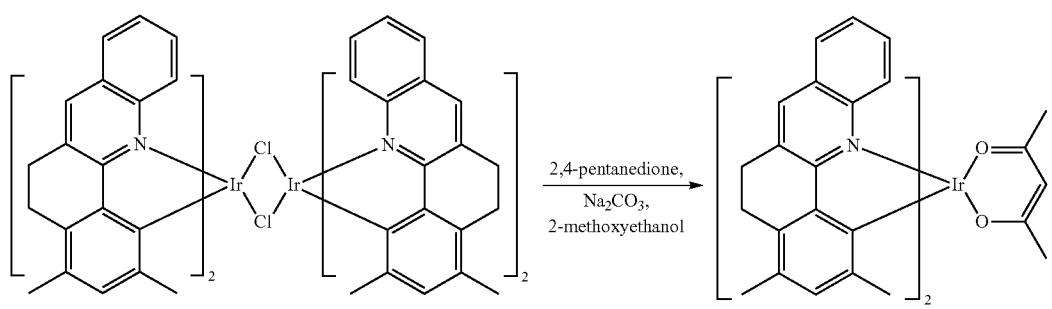

2.0 g (1.3 mmol) of the dimer, 1.3 g (13 mmol) of 2,4-pentanedione, 1.4 g (13 mmol) of sodium carbonate, and 50 mL of 2-methoxyethanol were mixed in a 100 mL flask. The reaction mixture was heated to reflux under nitrogen overnight. Upon cooling, the solid was filtered, washed by methanol, then purified by silica gel column chromatography to afford 1.2 g (57% yield) of product.

Synthesis of Compound 20

Step 1

Step 2

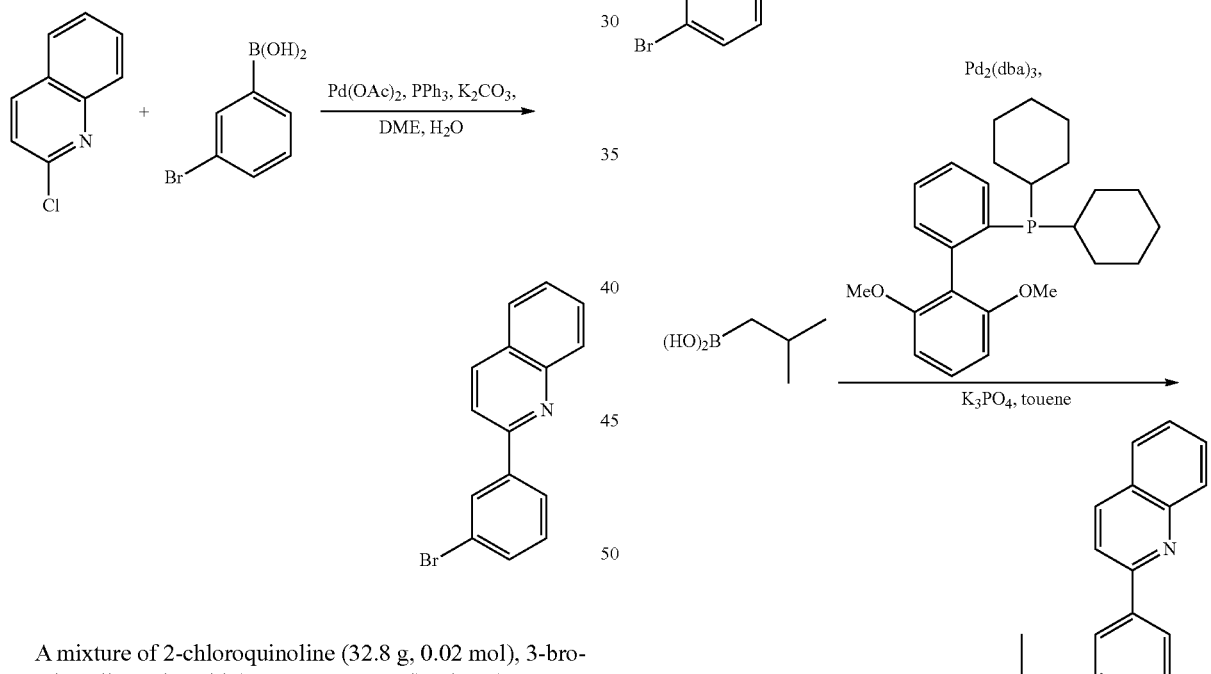

A mixture of 2-chloroquinoline (32.8 g, 0.02 mol), 3-bromophenylboronic acid (40.53 g, 0.02 mol), $Ph_3P$ (5.3 g, 10 mol %), $Pd(OAc)_2$ (2.3 g, 5 mol %), and $K_2CO_3$ (111.4 g, 0.08 mol) in 300 mL of dimethoxyethane and 300 mL of $H_2O$ was purged with nitrogen for 20 min and refluxed for 8 hrs under nitrogen. The reaction was then allowed to cool to room temperature, and the organic phase was separated from the aqueous phase. The aqueous phase was washed with ethyl acetate. The organic fractions were combined and dried over magnesium sulfate, and the solvent was removed under vacuum. The product was chromatographed using silica gel with ethyl acetate and hexanes as the eluent to yield 55 g (95% yield) of a white solid.

A mixture of 2-(3-bromophenyl)quinoline (10.0 g, 0.035 mol), isobutylboronic acid (7.2 g, 0.07 mol), $Pd_2(dba)_3$ (0.32 g, 1 mol %), 2-dicyclohexylphosphino-2',6'-dimethoxybiphenyl (0.7 g, 4 mol %), and potassium phosphate monohydrate (24 g, 0.1 mol) in 100 mL of toluene was purged with nitrogen for 20 min and refluxed overnight under atmosphere. The reaction mixture was allowed to cool, and the solvent was removed under vacuum. The crude product was chromatographed using a silica gel column with 2% ethyl acetate in hexanes as the eluent. The solvent was then removed under vacuo to give 8.0 g of product.

Step 3

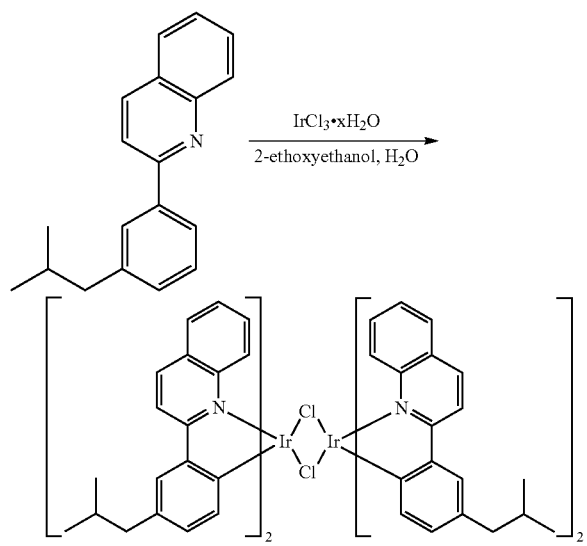

2-(3-isobutylphenyl)quinoline (5.4 g, 20.7 mmol) and iridium(III) chloride (2.5 g, 7 mmol) were dissolved in 50 mL of a 3:1 mixture of 2-ethoxyethanol and water, respectively, in a 100 mL round-bottom flask. Nitrogen was bubbled through the solution for 10 min, and then the mixture was refluxed under nitrogen for 16 hrs. The reaction mixture was then allowed to cool to room temperature, and the precipitate was filtered and washed with methanol. The dimer was then dried under vacuum and used for next step without further purification. 4.0 g of the dimer was obtained after vacuum drying.

Step 4

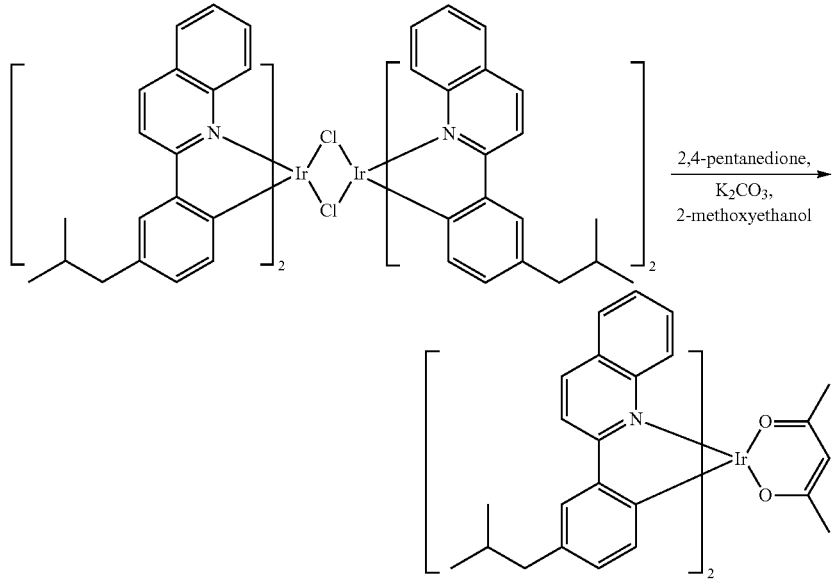

The dimer (3.0 g, 1.8 mmol), 2,4-pentanedione (1.8 g, 18.0 mol), and $K_2CO_3$ (3.0 g, 18.0 mmol) were added to 100 mL of 2-methoxyethanol and stirred at room temperature for 24 hrs. The precipitate was filtered and washed with methanol. The solid was redissolved in dichloromethane and passed through a plug with Celite, silica gel, and basic alumina. The solvent was evaporated under vacuum to give 2.0 g of product.

Synthesis of Compound 21

Step 1

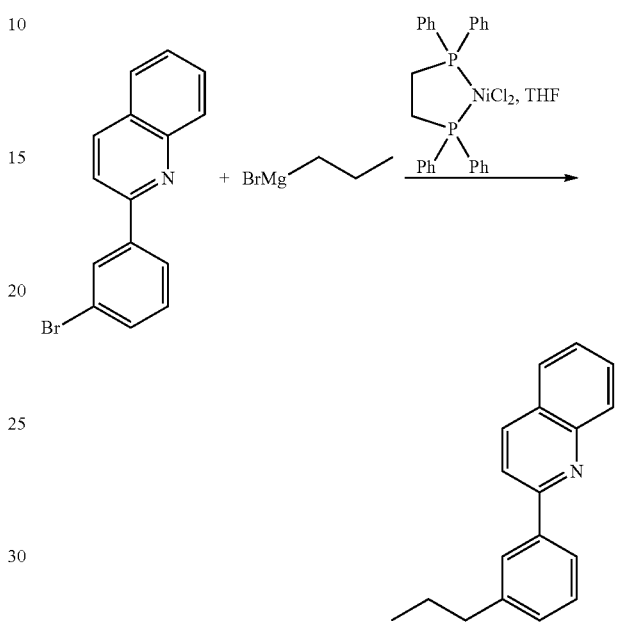

Compound 20

2-(3-bromophenyl)quinoline (10.0 g, 35 mmol) from Step 1 of Compound 20, 1,2-bis(diphenylphosphino)ethane]dichloronickel(II) (0.5 g, 0.9 mmol), and 100 mL anhydrous THF were mixed in a 500 mL round-bottom flask. Nitrogen was bubbled through the mixture, and the flask was placed in an ice bath for 30 min. 88 mL of 2.0 M propylmagnesium bromide in ether was added dropwise to the reaction mixture over a period of 20 min after which the mixture was further stirred for 30 min and then quenched with water. The mixture was brought to room temperature, and ethyl acetate was added. The water layer was removed. The organic phase was dried over magnesium sulfate, and the solvent was removed in vacuo. The product was chromatographed using a silica gel column with ethylacetate and hexanes as the eluent. The solvent was once again removed to give 5 g of product.

Step 2

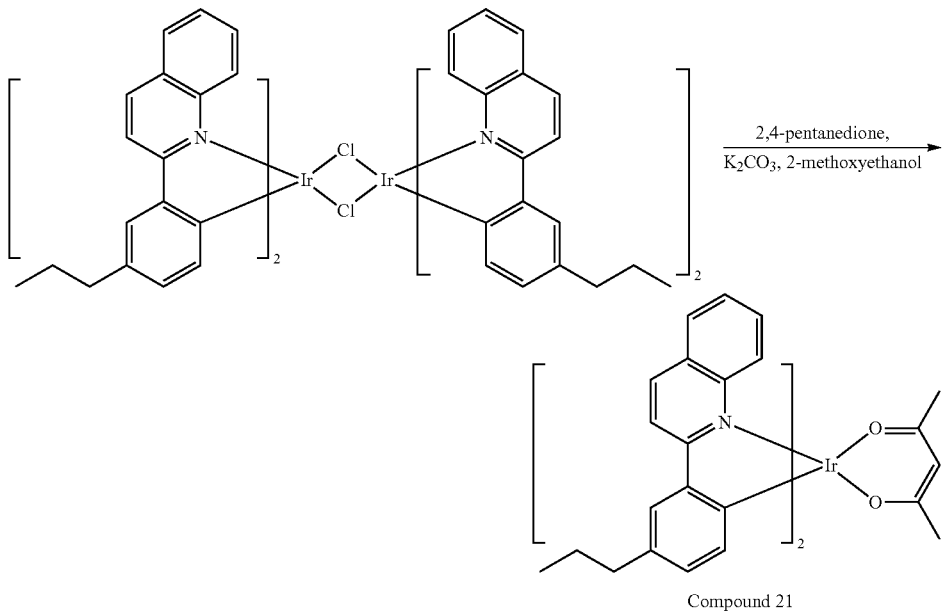

2-(3propylphenyl)quinoline (3.2 g, 13.0 mmol) and iridium(III) chloride (1.8 g, 5.2 mmol) were dissolved in 50 mL of a 3:1 mixture of 2-ethoxyethanol and water, respectively, in a 100 mL round-bottom flask. Nitrogen was bubbled through the solution for 10 min and then refluxed under nitrogen for 16 hrs. The reaction mixture was then allowed to cool to room temperature, and the precipitate was filtered and washed with methanol. The dimer was then dried under vacuum and used for next step without further purification. 2.6 g of the dimer was obtained after vacuum drying.

Step 3

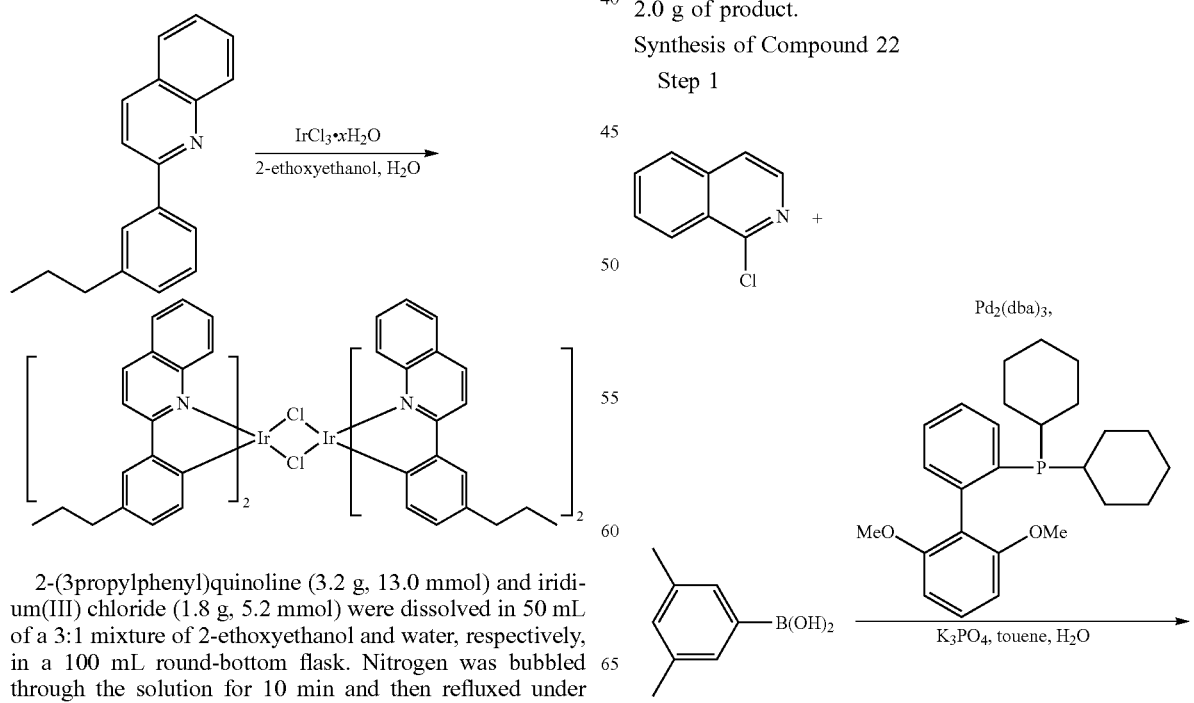

Compound 21

The dimer (2.6 g, 1.8 mmol), 2,4-pentanedione (1.8 g, 18.0 mol), and $K_2CO_3$ (3.0 g, 18.0 mmol) were added to 100 mL of 2-methoxyethanol and stirred at room temperature for 24 hrs. The precipitate was filtered and washed with methanol. The solid was redissolved in dichloromethane and passed through a plug with Celite, silica gel, and basic alumina. The solvent was evaporated under vacuum to give 2.0 g of product.

Synthesis of Compound 22

Step 1

-continued

Step 2

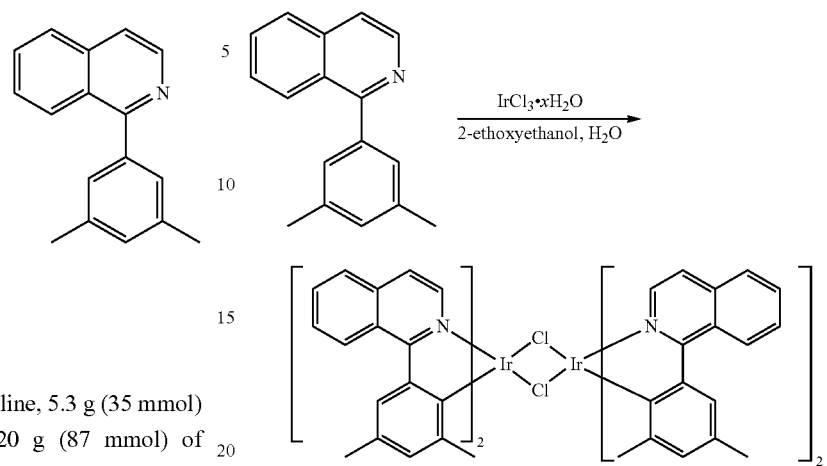

4.8 g (29 mmol) of 1-chloroisoquinoline, 5.3 g (35 mmol) of 3,5-dimethylphenylboronic acid, 20 g (87 mmol) of potassium phosphate, 0.5 g (1.16 mmol) of 2-dicyclohexyl-phosphino-2',6'-dimethoxybiphenyl, 100 mL of toluene, and 30 mL of water were mixed in a three-neck flask. The system was bubbled with nitrogen for 30 min. 0.27 g (0.29 mmol) of $Pd_2(dba)_3$ was added, and the mixture was heated to reflux for 4 hrs. After cooled to room temperature, the reaction mixture was filtered through a Celite bed. The product was columned with 2% ethyl acetate and hexanes. 6.0 g (87% yield) of product was obtained after column.

5.5 g (23.6 mmol) of 1-(3,5-dimethylphenyl)isoquinoline, and 3.4 g (9.5 mmol) of iridium chloride were mixed in 90 mL of 2-ethoxyethanol and 30 mL of water. The mixture was purged with nitrogen for 10 min and then heated to reflux for 24 hrs. After cooled to room temperature, the solid was collected by filtration. The solid was thoroughly washed with methanol and hexanes. The product was dried under vacuum. 4.6 g (70% yield) of solid was obtained and used for the next step without further purification.

Step 3

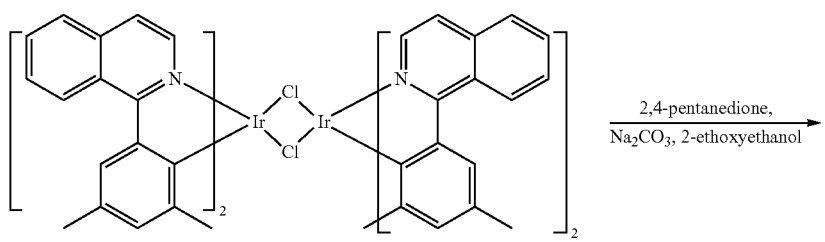

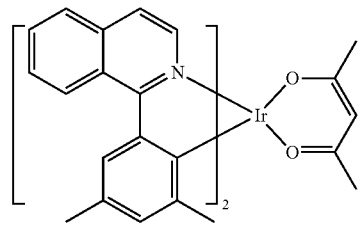

Compound 22

4.5 g (3.25 mmol) of the dimer, 3.3 g (32.5 mmol) of 2,4-pentanedione, and 1.7 g (16.3 mmol) of sodium carbonate were refluxed in 150 mL of 2-ethoxyethanol for 10 hrs. After cooled to room temperature, the mixture was filtered through a Celite bed and washed thoroughly with methanol. The red solid on top was then washed with dichloromethane. The product was purified by column chromatography using 1:1 dichloromethane and hexanes as eluent. 1.6 g of product was obtained. The product was further purified by high vacuum sublimation at 220° C.

Synthesis of Compound 23

Step 1

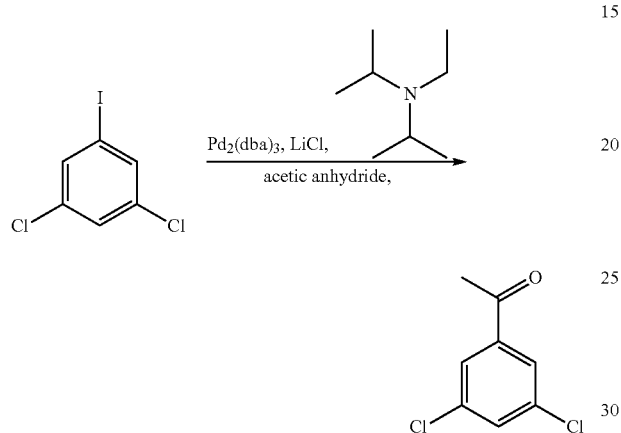

Dichloroiodobenzene (37.0 g 136 mmol), Pd$_2$(dba)$_3$ (1.5 g, 1.6 mmol), and lithium chloride (29.0 g, 682 mmol) were dissolved in 100 mL of DMF in a 500 mL round-bottom flask. 64.0 mL of acetic anhydride and 47.0 mL of N-ethyldiisopropylamine were then added to the reaction mixture. The reaction was heated to 100° C. for 8 hrs. Water was added to the reaction mixture, and the product was extracted with ethyl acetate and chromatographed using a silica gel column with ethyl acetate and hexanes as the eluent. 8 g of product was obtained.

Step 2

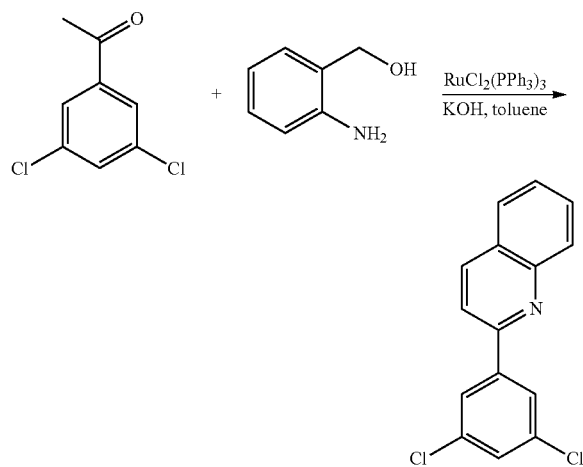

2-aminobenzyl alcohol (6.0 g, 48 mmol), 3,5-dichloroacetophenone (12.0 g, 63.5 mmol), RuCl$_2$(PPh$_3$)$_3$ (0.5 g, 10 mol %), and potassium hydroxide (2.4 g, 42.0 mmol) was refluxed in 100 mL of toluene for 10 hrs. Water was collected from the reaction using a Dean-Stark trap. The reaction mixture was allowed to cool to room temperature and filtered through a silica gel plug. The product was further purified with a silica gel column using 2% ethyl acetate in hexanes as the eluent. 4.0 g (30% yield) product was obtained after column. The product was further recrystallized from isopropanol. 3.5 g of product was obtained.

Step 3

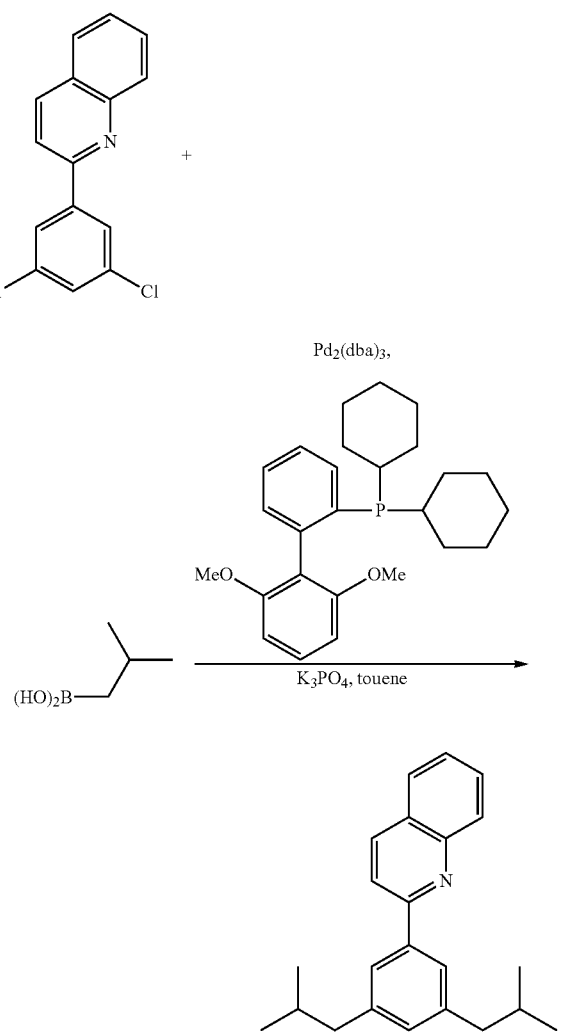

2-(3,5-dichlorophenyl)quinoline (4.0 g, 14.6 mmol), isobutylboronic acid (6.0 g, 58.4 mol), Pd$_2$(dba)$_3$ (0.13 g, 1 mol %), 2-dicyclohexylphosphino-2',6'-dimethoxybiphenyl (0.24 g, 4 mol %), and potassium phosphate monohydrate (10 g, 13.8 mmol) were mixed in 100 mL of toluene in a 250 mL round-bottom flask. Nitrogen was bubbled through the mixture for 20 min, and the mixture was refluxed under nitrogen overnight. The reaction mixture was allowed to cool, and the solvent removed under vacuum. The crude product was chromatographed using a silica gel column with 2% ethyl acetate in hexanes as the eluent. The solvent was then removed under vacuo to give 3.5 g of product.

Step 4

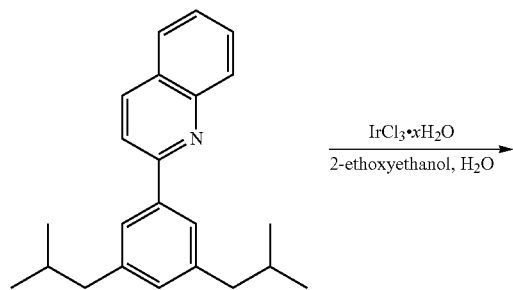

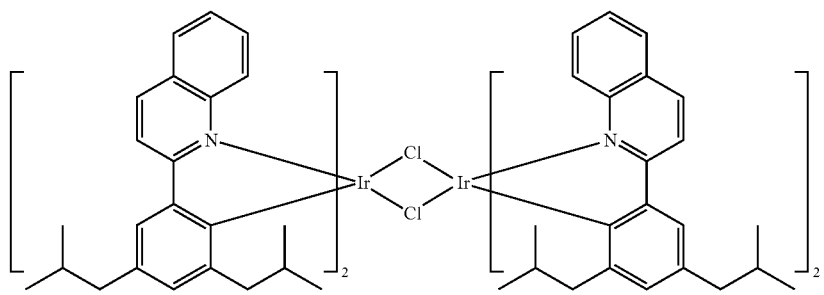

2-(3,5-diisobutylphenyl)quinoline (3.0 g, 9.50 mmol) and iridium(III) chloride (0.70 g, 2.4 mmol) were dissolved in 50 mL of a 3:1 mixture of 2-ethoxyethanol and water, respectively, in a 100 mL round-bottom flask. Nitrogen was bubbled through the solution for 10 min and then refluxed under a nitrogen for 16 hrs. The reaction mixture was then allowed to cool to room temperature, and the precipitate was filtered and washed with methanol. The dimer was then dried under vacuum and used for next step without further purification. 2.0 g of the dimer was obtained after vacuum drying.

Step 5

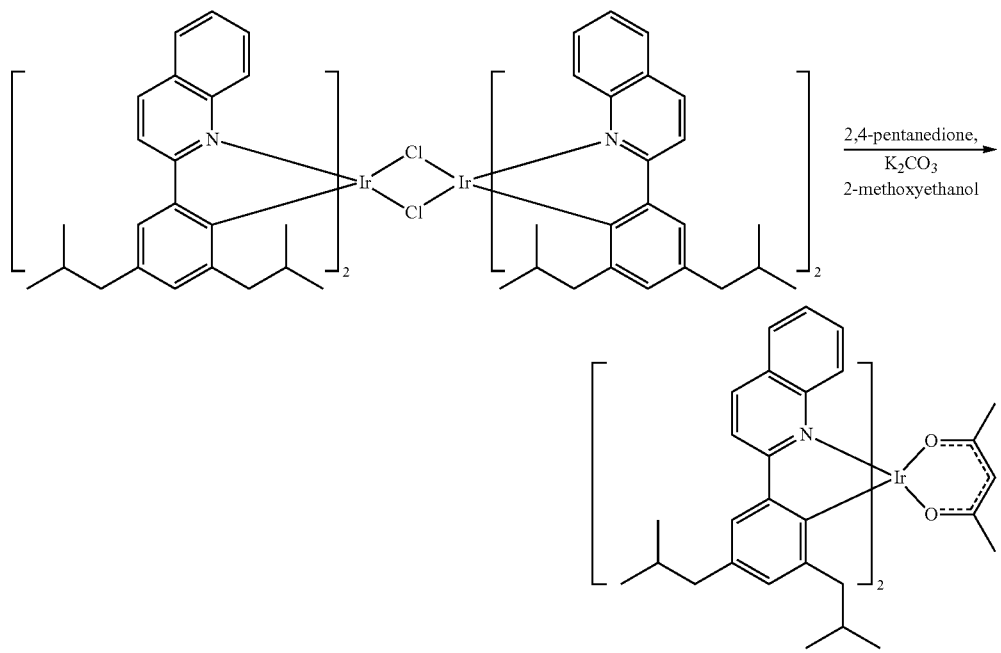

Compound 23

A mixture of the dimer, 2,4-pentanedione, and K$_2$CO$_3$ in 2-methoxyethanol is stirred at room temperature for 24 hrs. The precipitate is filtered and washed with methanol. The solid is redissolved in dichloromethane and passed through a plug with Celite, silica gel, and basic alumina. The solvent is evaporated under vacuum to give the product.

Synthesis of Compound 24

Step 1

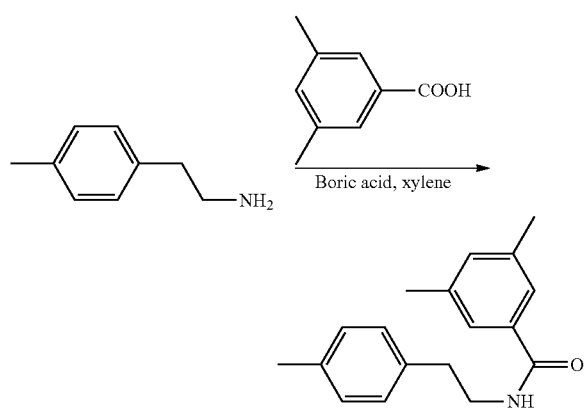

10.6 g (78.4 mmol) of 2-p-tolylethanamine, 10.7 g (71.2 mmol) of 3,5-dimethylbenzoic acid, and 0.5 g of boric acid were heated to reflux in 200 mL of p-xylene with a Dean-Stark trap overnight. After cooled to room temperature, 400 mL of hexanes was added. The solid was collected by filtration. The product was dried under vacuum. 16.9 g of white solid was obtained. The product was used for the next step without further purification.

Step 2

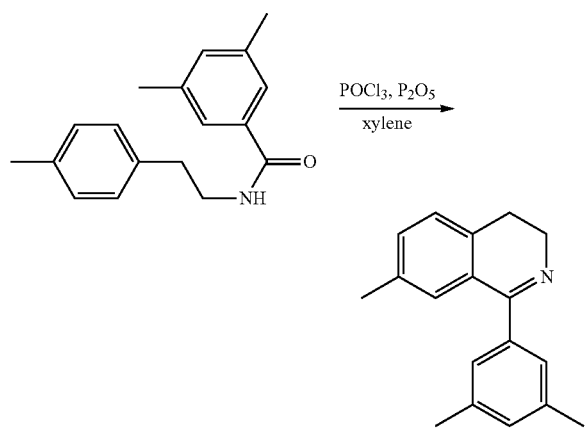

6.9 of 3,5-dimethyl-N-(4-methylphenethyl)benzamide, 60 mL of POCl$_3$, and 50 g of P$_2$O$_5$ were refluxed in 150 mL of p-xylene under nitrogen for 4 hrs. After cooled to room temperature, the solvent was decanted. The solid was dissolved with ice cold water. The solution was neutralized with potassium hydroxide solution, then extracted with toluene. After solvent evaporation, the residue was purified by column chromatography using 1:3 hexanes and ethyl acetate. 12 g (76%) of product was obtained.

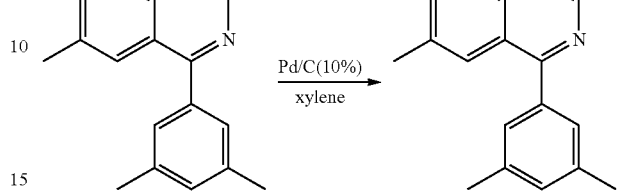

12 g (48 mmol) of 1-(3,5-dimethylphenyl)-7-methyl-3,4-dihydroisoquinoline and 2.0 g of 10% palladium on carbon were refluxed in 200 mL of p-xylene for 4 hrs. After cooled to room temperature, the reaction mixture was filtered through a Celite bed. The product was then purified by column using 5% ethyl acetate in hexanes as eluent. 10 g of product was obtained. The product was further purified by recrystallizing from hexanes three times. 6.2 g of pure product was obtained after multiple recrystallizations.

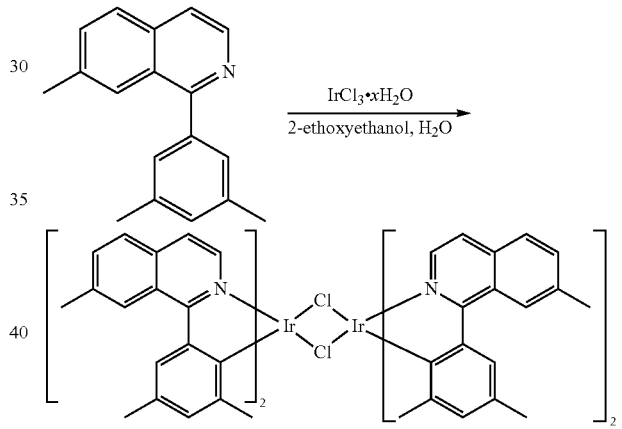

5.5 g (22 mmol) of 1-(3,5-dimethylphenyl)isoquinoline and 2.64 g (7.4 mmol) of iridium chloride were mixed in 90 mL of 2-ethoxyethanol and 30 mL of water. The mixture was purged with nitrogen for 10 min and then heated to reflux for 14 hrs. After cooled to room temperature, the solid was collected by filtration. The solid was thoroughly washed with methanol and hexanes. The product was dried under vacuum. 3.75 g (70% yield) of the dimer was obtained, which was used for next step without further purification.

Step 3

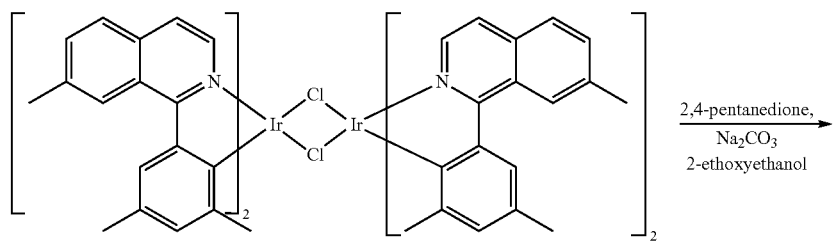

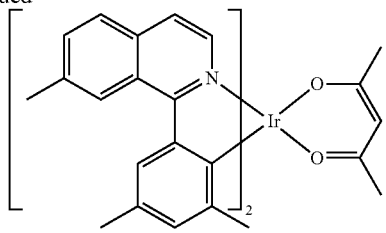

Compound 24

3.7 g (2.6 mmol) of the dimer, 2.6 g (26 mmol) of 2,4-pentanedione, and 1.4 g (13 mmol) of sodium carbonate were reacted in 150 mL of 2-ethoxyethanol at room temperature for 72 hrs. Deep red precipitate formed. The mixture was filtered through a Celite bed and washed thoroughly with methanol. The red solid on top was then washed with dichloromethane. 3.6 g of product was obtained. The product was further purified by high vacuum sublimation at 235° C.

Exemplary and Comparative Devices

All devices are fabricated by high vacuum (<$10^{-7}$ Torr) thermal evaporation. The anode electrode is ~1200 Å of indium tin oxide (ITO). The cathode consists of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack consists of sequentially, from the ITO surface, 100 Å thick of Ir(3-Meppy)$_3$ as the hole injection layer (HIL), 400 Å of 4,4'-bis[N-(1-naphthyl)-N-phenylamino]biphenyl (α-NPD) as the hole transporting layer (HTL), 300 Å of BAlq doped with 6-12 wt % of the dopant emitter (exemplary compounds and comparative compounds) as the emissive layer (EML), 550 Å of tris(8-hydroxyquinolinato)aluminum (Alq$_3$) as the electron transport layer (ETL). The current-voltage-luminance (IVL) characteristics and operational lifetimes are measured and summarized in the Table 1. The device performance is compared at 10 mA/cm$^2$ and lifetime is compared at J=40 mA/cm$^2$ (constant dc) at room temperature and 70° C.

Additional Devices with Compound 1

Using the general method as described above and the additional materials described below, the following devices were fabricated using compound 1 as the dopant emitter:

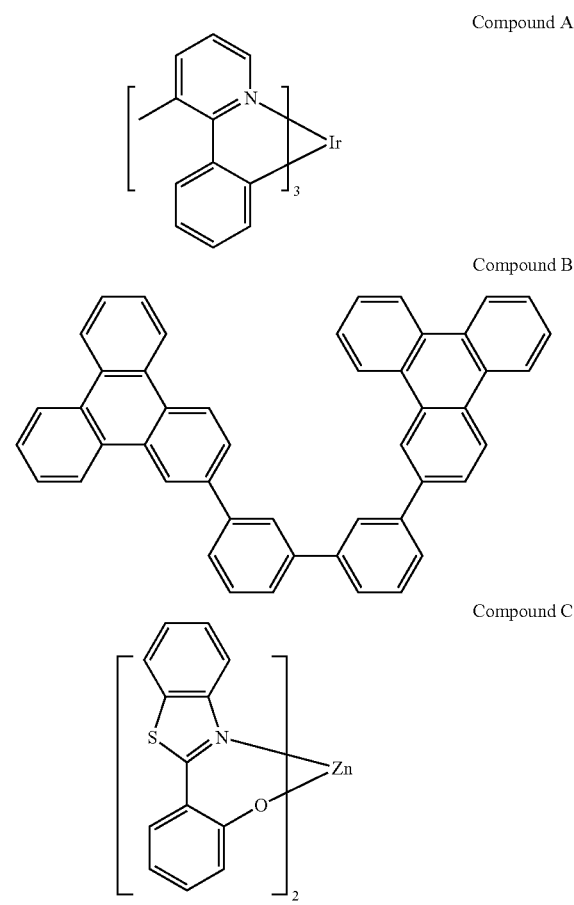

Compound A

Compound B

Compound C

Devices with Compound 1

| Device | Device description |
|---|---|
| 1a | ITO/Compound A (100 Å)/NPD (400 Å)/BAlq: Compound 1(6%) (300 Å)/Alq3 (550 Å)LiF/Al |
| 1b | ITO/Compound A (100 Å)/NPD (400 Å)/BAlq: Compound 1(9%) (300 Å)/Alq3 (550 Å)/LiF/Al |
| 1c | ITO/Compound A (100 Å)/NPD (400 Å)/BAlq: Compound 1(12%) (300 Å)/Alq3 (550 Å)/LiF/Al |
| 1d | ITO/Compound A (100 Å)/NPD (400 Å)/BAlq: Compound A (10%): Compound 1(3%) (300 Å)/Balq (100)/Alq3 (450 Å)/LiF/Al |
| 1e | ITO/Compound A (100 Å)/NPD (400 Å)/Compound B: Compound 1(12%) (300 Å)/Alq3 (550 Å)/LiF/Al |
| 1f | ITO/Compound A (100 Å)/NPD (400 Å)/Compound B: Compound 1(12%) (300 Å)/Compound B (100 Å)/Alq3 (450 Å)/LiF/Al |
| 1g | ITO/Compound A (100 Å)/NPD (400 Å)/Compound C: Compound 1(6%) (300 Å)/Alq3 (550 Å)/LiF/Al |

-continued

| Device | Device description |
|---|---|
| 1h | ITO/Compound A (100 Å)/NPD (400 Å)/Compound C: Compound 1(9%) (300 Å)/Alq3 (550 Å)/LiF/Al |
| 1i | ITO/Compound A (100 Å)/NPD (400 Å)/Compound C: Compound 1(12%) (300 Å)/Alq3 (550 Å)/LiF/Al |

Performance of Devices with Compound 1

| | | | | At 500 nits | | | $T_{80\%}$ at 40 mA/cm² (hr) | | |
|---|---|---|---|---|---|---|---|---|---|
| Device | EML dopant % | λ max | CIE | V (V) | LE (cd/A) | EQE (%) | $L_0$ (cd/m²) | RT | 70° C. |
| 1a | 6 | 620 | 0.66 0.33 | 7.7 | 21.9 | 19.00 | 6472 | n.m. | 62 |
| 1b | 9 | 622 | 0.67 0.33 | 7.1 | 20.2 | 19.17 | 6447 | n.m. | 62 |
| 1c | 12 | 622 | 0.67 0.33 | 6.9 | 18.7 | 18.00 | 6382 | n.m. | 73 |
| 1d | 3 | 618 | 0.66 0.34 | 7.8 | 27.1 | 22.9 | n.m. | n.m. | n.m. |
| 1e | 12 | 626 | 0.673 0.325 | 6.8 | 15.6 | 17 | 5098 | n.m. | n.m. |
| 1f | 12 | 626 | 0.673 0.325 | 7.8 | 16.3 | 17.6 | 5041 | n.m. | n.m. |
| 1g | 6 | 622 | 0.668 0.330 | 6.1 | 20 | 19.3 | 6137 | 287 | 31 |
| 1h | 9 | 624 | 0.671 0.327 | 5.7 | 18.2 | 18.4 | 5798 | 470 | 42 |
| 1i | 12 | 625 | 0.672 0.327 | 5.4 | 17.6 | 18.2 | 5779 | 704 | 58 |

Additional Devices with Compound 9

Using the general method as described above, the following devices were fabricated using compound 9 as the dopant emitter.

Devices with Compound 9

| Device | Device description |
|---|---|
| 9a | ITO/Compound A (100 Å)/NPD (400 Å)/BAlq: Compound 9(6%) (300 Å)/Alq3 (550 Å)/LiF/Al |
| 9b | ITO/Compound A (100 Å)/NPD (400 Å)/BAlq: Compound 9(9%) (300 Å)/Alq3 (550 Å)/LiF/Al |
| 9c | ITO/Compound A (100 Å)/NPD (400 Å)/BAlq: Compound 9(12%) (300 Å)/Alq3 (550 Å)/LiF/Al |
| 9d | ITO/Compound A (100 Å)/NPD (400 Å)/BAlq: Compound A (10%): Compound 9(3%) (300 Å)/Balq (100 Å)/Alq3 (450 Å)/LiF/Al |
| 9e | ITO/Compound A (100 Å)/NPD (400 Å)/BAlq: Compound A (10%): Compound 9(3%) (300 Å)/Alq3 (550 Å)/LiF/Al |
| 9f | ITO/Compound A (100 Å)/NPD (400 Å)/Compound C: Compound 9(9%) (300 Å)/Compound C (100 Å)/Alq3 (450 Å)/LiF/Al |
| 9g | ITO/Compound A (100 Å)/NPD (400 Å)/Compound C: Compound 9(9%) (300 Å)/BAlq (100 Å)/Alq3 (450 Å)/LiF/Al |
| 9h | ITO/Compound A (100 Å)/NPD (400 Å)/Compound C: Compound 9(9%) (300 Å)/Alq3 (550 Å)/LiF/Al |
| 9i | ITO/Compound A (100 Å)/NPD (400 Å)/Compound C: Compound A (10%): Compound 9(3%) (300 Å)/Compound C (100 Å)/Alq3 (450 Å)/LiF/Al |
| 9j | ITO/Compound A (100 Å)/NPD (400 Å)/Compound C: Compound A (10%): Compound 9(3%) (300 Å)/BAlq (100 Å)/Alq3 (450 Å)/LiF/Al |
| 9k | ITO/Compound A (100 Å)/NPD (400 Å)/Compound C: Compound A (10%): Compound 9(3%) (300 Å)/Alq3 (550 Å)/LiF/Al |

Performance of Devices with Compound 9

| Device | EML dopant % | λ max | CIE | V (V) | LE (cd/A) | EQE (%) | L₀ (cd/m²) | T₈₀% at 40 mA/cm² (hr) RT | 70° C. |
|---|---|---|---|---|---|---|---|---|---|
| | | | At 1000 nits | | | | | | |
| 9a | 6 | 615 | 0.653 0.345 | 8.6 | 25.5 | 19.50 | 7892 | 333 | 55 |
| 9b | 9 | 616 | 0.654 0.343 | 8 | 26.5 | 20.80 | 8215 | 352 | 55 |
| 9c | 12 | 617 | 0.656 0.342 | 7.7 | 24.2 | 19.30 | 7992 | 330 | 60 |
| 9d | 3 | 612 | 0.647 0.349 | 6.3 | 29.4 | 21.1 | 9809 | n.m. | 106 |
| 9e | 3 | 612 | 0.642 0.352 | 6.3 | 14.6 | 10.3 | 6950 | n.m. | 102 |
| 9f | 9 | 618 | 0.659 0.339 | 5.6 | 25.6 | 21.1 | 7971 | n.m. | 34 |
| 9g | 9 | 618 | 0.659 0.339 | 6.3 | 25.6 | 21.1 | 7871 | n.m. | 25 |
| 9h | 9 | 618 | 0.659 0.338 | 5.5 | 24.5 | 20.4 | 7642 | n.m. | 33 |
| 9i | 3 | 612 | 0.646 0.351 | 4.8 | 34.6 | 24.5 | 11334 | n.m. | 45 |
| 9j | 3 | 612 | 0.646 0.351 | 5.4 | 33 | 23.5 | 10775 | n.m. | 41 |
| 9k | 3 | 612 | 0.646 0.351 | 5 | 25.2 | 18 | 9131 | n.m. | 38 |

Additional Devices with Compound 22

Using the general method as described above, the following devices were fabricated using compound 22 as the dopant emitter.

Devices with Compound 22

| Device | Device description |
|---|---|
| 22a | ITO/Compound A (100 Å)/NPD (400 Å)/BAlq: Compound 22(6%) (300 Å)/Alq3 (550 Å)/LiF/Al |
| 22b | ITO/Compound A (100 Å)/NPD (400 Å)/BAlq: Compound 22(9%) (300 Å)/Alq3 (550 Å)/LiF/Al |
| 22c | ITO/Compound A (100 Å)/NPD (400 Å)/BAlq: Compound 22(12%) (300 Å)/Alq3 (550 Å)/LiF/Al |
| 22d | ITO/Compound A (100 Å)/NPD (400 Å)/BAlq: Compound A (10%): Compound 22(3%) (300 Å)/Balq (100)/Alq3 (450 Å)/LiF/Al |

Performance of Devices with Compound 22

| Device | EML dopant % | λ max | CIE | V (V) | LE (cd/A) | EQE (%) | L₀ (cd/m²) | T₈₀% at 40 mA/cm² (hr) RT | 70° C. |
|---|---|---|---|---|---|---|---|---|---|
| | | | At 1000 nits | | | | | | |
| 22a | 6 | 635 | 0.693 0.304 | 10 | 10.8 | 18.3 | 3,500 | n.m. | 62 |
| 22b | 9 | 637 | 0.695 0.303 | 9.9 | 10.5 | 18.5 | 3,408 | n.m. | 73 |
| 22c | 12 | 637 | 0.693 0.304 | 9.5 | 10 | 17.7 | 3,277 | n.m. | 80 |
| 22d | 3 | 633 | 0.691 0.307 | 9.4 | 13.6 | 21.1 | 3,445 | n.m. | 116 |

What is claimed is:

1. An iridium compound having the formula:

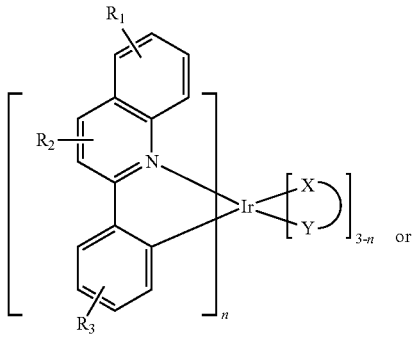

or

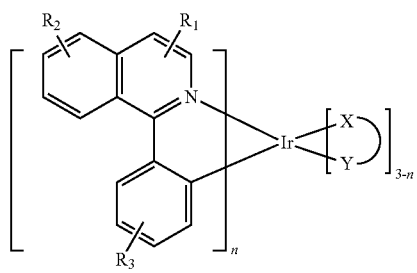

wherein n is 1, 2 or 3;

each of $R_1$, $R_2$, and $R_3$ is independently a hydrogen, or a mono-, di-, tri-, tetra-, or penta-substitution of alkyl or aryl;

at least one of $R_1$, $R_2$, and $R_3$ is a branched alkyl containing at least 4 carbon atoms, and wherein the branching occurs at a position further than the benzylic position; and X—Y is an ancillary ligand.

2. The compound of claim 1, wherein the branched alkyl is an isobutyl group.

3. The compound of claim 1, wherein X—Y is acac.

4. The compound of claim 1, selected from the group consisting of:

Compound 9

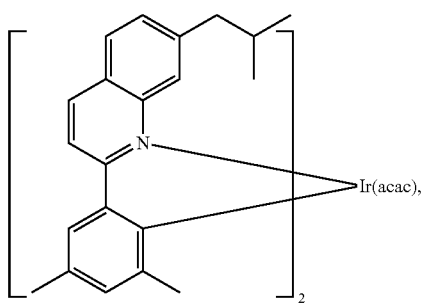

Compound 20

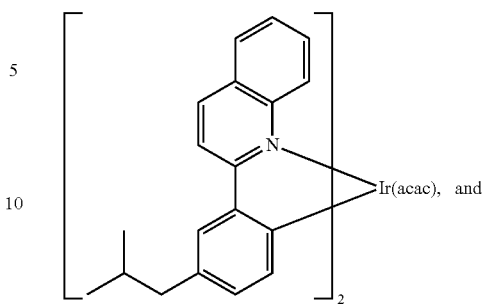

Compound 23

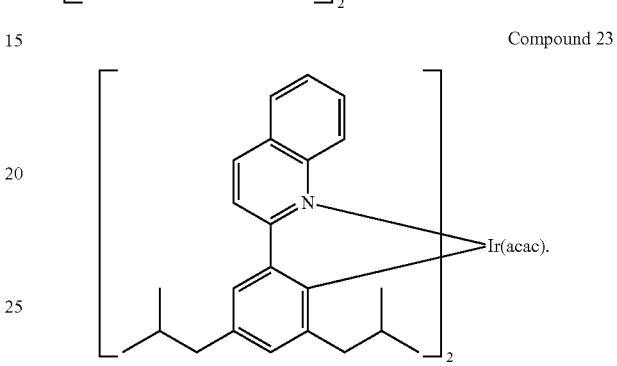

5. A compound including a ligand having the formula:

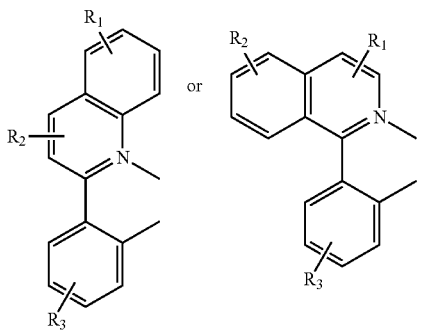

each of $R_1$, $R_2$, and $R_3$ is independently a hydrogen, or a mono-, di-, tri-, tetra-, or penta-substitution of alkyl or aryl;

at least one of $R_1$, $R_2$, and $R_3$ is a branched alkyl containing at least 4 carbon atoms, and wherein the branching occurs at a position further than the benzylic position.

6. The compound of claim 5, wherein the ligand is coordinated to a metal having an atomic number greater than 40.

7. The compound of claim 5, wherein the metal is Ir.

8. An organic light emitting device comprising:
an anode;
a cathode; and
an emissive organic layer, disposed between the anode and the cathode, the organic layer further comprising a compound having the formula:

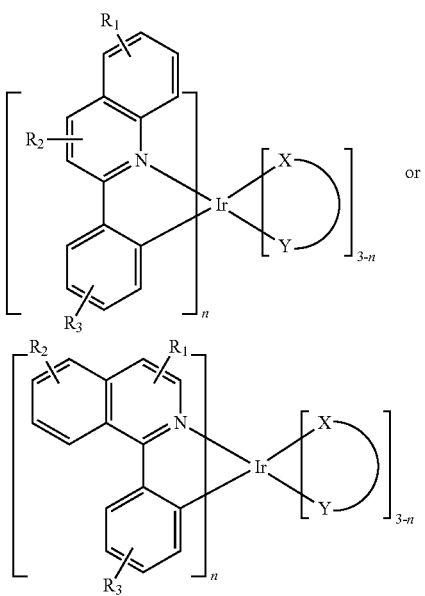

wherein n is 1, 2 or 3;
each of $R_1$, $R_2$, and $R_3$ is independently a hydrogen, or a mono-, di-, tri-, tetra-, or penta-substitution of alkyl or aryl;
at least one of $R_1$, $R_2$, and $R_3$ is a branched alkyl containing at least 4 carbon atoms, and wherein the branching occurs at a position further than the benzylic position; and
X—Y is an ancillary ligand.

9. The device of claim 8, wherein the organic emissive layer further comprises BAlq or Compound C

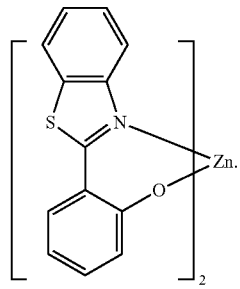

10. The device of claim 8, wherein the branched alkyl is an isobutyl group.

11. The device of claim 8, wherein X—Y is acac.

12. The device of claim 8, selected from the group consisting of:

Compound 9

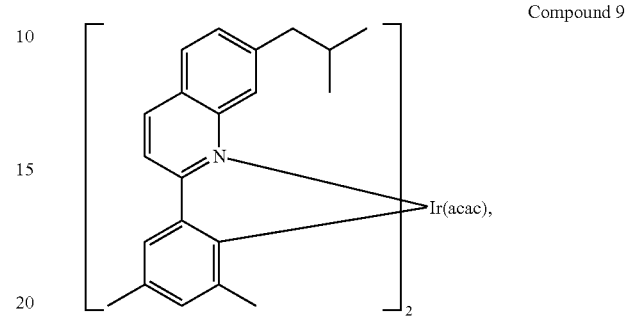

Compound 20

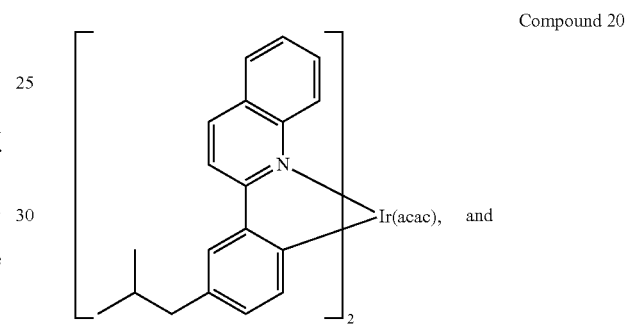
and

Compound 23

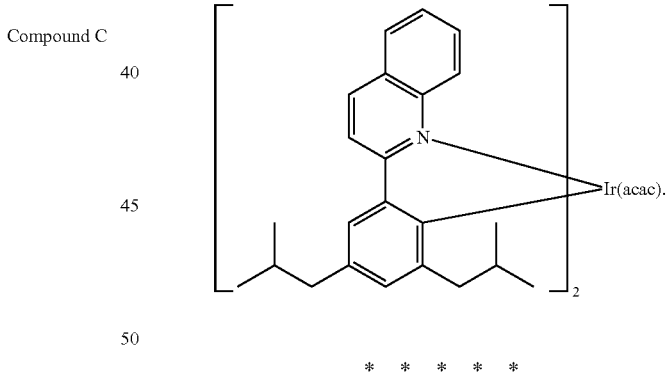

* * * * *